United States Patent
Stapper et al.

(10) Patent No.: US 7,335,671 B2
(45) Date of Patent: Feb. 26, 2008

(54) ARYLCYCLOALKYL-SUBSTITUTED ALKANOIC ACID DERIVATIVES, PROCESSES FOR THEIR PREPARATION AND THEIR USE AS PHARMACEUTICALS

(75) Inventors: Christian Stapper, Mainz (DE); Stefanie Keil, Hofheim (DE); Heiner Glombik, Hofheim (DE); Eugen Falk, Frankfurt (DE); Jochen Goerlitzer, Frankfurt am Main (DE); Dirk Gretzke, Frankfurt (DE); Hans-Ludwig Schaefer, Hochheim (DE); Wolfgang Wendler, Selters (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 362 days.

(21) Appl. No.: 10/789,017

(22) Filed: Feb. 27, 2004

(65) Prior Publication Data

US 2004/0209920 A1    Oct. 21, 2004

Related U.S. Application Data

(60) Provisional application No. 60/487,510, filed on Jul. 15, 2003.

(30) Foreign Application Priority Data

Feb. 27, 2003    (DE)    ............................ 103 08 355

(51) Int. Cl.
A61K 31/4439    (2006.01)
A61K 31/422    (2006.01)
C07D 413/02    (2006.01)

(52) U.S. Cl. .................. 514/340; 514/374; 548/215
(58) Field of Classification Search ................ 514/374, 514/340; 548/215
See application file for complete search history.

(56) References Cited

U.S. PATENT DOCUMENTS

| | | | |
|---|---|---|---|
| 5,130,770 A | 7/1992 | Blanc et al. | |
| 6,221,633 B1 | 4/2001 | Ertl et al. | |
| 6,221,897 B1 | 4/2001 | Frick et al. | |
| 6,245,744 B1 | 6/2001 | Frick et al. | |
| 6,277,831 B1 | 8/2001 | Frick et al. | |
| 6,342,512 B1 | 1/2002 | Kirsch et al. | |
| 6,506,778 B2 | 1/2003 | Defossa et al. | |
| 6,566,340 B2 | 5/2003 | Frick et al. | |
| 6,569,835 B2 | 5/2003 | Frick et al. | |
| 6,699,904 B2 | 3/2004 | Hayward et al. | |
| 6,897,198 B2 | 5/2005 | Frick et al. | |
| 6,908,926 B1 | 6/2005 | Dorwald et al. | |

FOREIGN PATENT DOCUMENTS

| WO | WO 94/18183 | 8/1994 |
|---|---|---|
| WO | WO 94/18184 | 8/1994 |
| WO | WO 96/38428 | 12/1996 |
| WO | WO 97/26265 | 7/1997 |
| WO | WO 97/41097 | 11/1997 |
| WO | WO 98/08871 | 3/1998 |
| WO | WO 98/19998 | 5/1998 |
| WO | WO 99/03861 | 1/1999 |
| WO | WO 99/15525 | 4/1999 |
| WO | WO 99/61431 | 12/1999 |
| WO | WO 99/62871 | 12/1999 |
| WO | WO 99/62872 | 12/1999 |
| WO | WO 99/67278 | 12/1999 |
| WO | WO 99/67279 | 12/1999 |
| WO | WO 00/40569 | 7/2000 |
| WO | WO 00/64876 | 11/2000 |
| WO | WO 00/64888 | 11/2000 |
| WO | WO 00/66585 | 11/2000 |
| WO | WO 00/71549 | 11/2000 |
| WO | WO 00/78312 A1 | 12/2000 |
| WO | WO 01/04146 A2 | 1/2001 |
| WO | WO 01/09111 A1 | 2/2001 |

(Continued)

OTHER PUBLICATIONS

Asakawa, A., et. al., Cocaine-Amphetamine-Regulated Transcript Influences Energy Metabolism Anxiety and Gastric Emptying in Mice, Hormone and Metabolic Reserch; vol. 33(9);2001; pp. 554-558.

(Continued)

*Primary Examiner*—Kamal A. Saeed
(74) *Attorney, Agent, or Firm*—Barbara E. Kurys

(57) ABSTRACT

Arylcycloalkyl-substituted alkanoic acid derivatives, processes for their preparation and their use as pharmaceuticals The invention relates to arylcycloalkyl-substituted alkanoic acid derivatives and to their physiologically acceptable salts and physiologically functional derivatives.

What is described are compounds of the formula I,

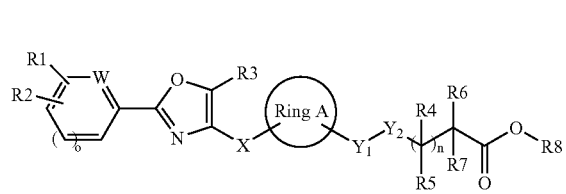

in which the radicals are as defined, and their physiologically acceptable salts and processes for their preparation. The compounds are suitable, for example, for the treatment and/or prevention of disorders of the fatty acid metabolism and glucose utilization disorders and also disorders in which insulin resistance is involved.

9 Claims, No Drawings

FOREIGN PATENT DOCUMENTS

| | | |
|---|---|---|
| WO | WO 01/21602 A1 | 3/2001 |
| WO | WO 01/40169 A1 | 6/2001 |
| WO | WO 01/40171 A1 | 6/2001 |
| WO | WO 01/72290 A2 | 10/2001 |
| WO | WO 01/81327 A1 | 11/2001 |
| WO | WO 01/83451 | 11/2001 |
| WO | WO 01/85695 A1 | 11/2001 |
| WO | WO 01/91752 A1 | 12/2001 |
| WO | WO 02/18355 | 3/2002 |
| WO | WO 02/38541 A1 | 5/2002 |
| WO | WO 02/46146 A1 | 6/2002 |
| WO | WO 02/50027 | 6/2002 |
| WO | WO 02/059098 | 8/2002 |
| WO | WO 02/096864 | 12/2002 |
| WO | WO 03/004458 A1 | 1/2003 |
| WO | WO 03/011819 | 2/2003 |
| WO | WO 03/020269 | 3/2003 |
| WO | WO 03/040174 A2 | 5/2003 |
| WO | WO 03/066581 A1 | 8/2003 |
| WO | WO 03/084922 | 10/2003 |
| WO | WO 03/084923 | 10/2003 |
| WO | WO 03/104188 | 12/2003 |
| WO | WO 2004/004665 | 1/2004 |

OTHER PUBLICATIONS

Berger, J., et. al., The Mechanisms of Action of PPARs, Annul. Rev. Med.; vol. 53; 2002; pp. 409-435.

Fruchart, J.C., et. al., PPARs, Metabolic Disease and Atherosclerosis, Pharmacological Research; vol. 44, No. 5; 2001' pp. 345-352.

Kersten, S., et al., Roles of PPARs in Health and Disease, Nature; vol. 405; May 25, 2000; pp. 421-424.

Kliewer, S.A., et. al., Peroxisome Proliferator-Activated Receptors: From Genes to Physiology, Recent Prog. Horm Res.; vol. 56; 2001; pp. 239-263.

Lee, D.W., et. al., Leptin agonists as a potential approach to the treatment of obesity, Drugs of the Future; vol. 26(9); 2001; pp. 873-881.

Motojima, K., et. al., Peroxisome Proliferator-Activated Receptor (PPAR): Structure, Mechanisms of Activation and Diverse Functions, Cell Structure and Function; vol. 18; 1993; pp. 267-277.

Okada, H., et. al., Synthesis and Antitumor Activities of Prodrugs of Benzoylphenylureas, Chem. Pharm. Bull.; vol. 42(1); 1994; pp. 57-61.

Pineda Torra, I., et. al., Peroxisome Proliferator-activated Receptors: from Transcriptional Control to Clinical Practice, Curr. Opin. Lipidol; vol. 12; 2001; pp. 245-254.

Pineda Torra, I., et. al., Peroxisome proliferator-activated receptor alpha in metabolic disease, inflammation, atherosclerosis and aging, Curr. Opin. Lipidol; vol. 10; 1999; pp. 151-159.

Vidal-Puig, A., et. al., Regulation of PPAR y Gene Expression by Nutrition and Obesity in Rodents, J. Clin. Invest.; vol. 97, No. 11, 1996; pp. 2553-2561.

Willson, T.M., et. al., The PPARs: From Orphan Receptors to Drug Discovery, Journal of Medicinal Chemistry; vol. 43, No. 4; 2000; pp. 527-550.

Zunft, H.J.F., et. al., Carob Pulp Preparation for Treatment of Hypercholesterolemia, Advances in Natural Therapy; vol. 18, No. 5; Sep.-Oct., 2001; pp. 230-236.

ARYLCYCLOALKYL-SUBSTITUTED ALKANOIC ACID DERIVATIVES, PROCESSES FOR THEIR PREPARATION AND THEIR USE AS PHARMACEUTICALS

This Application claims benefit under 35 U.S.C. § 119(e) of U.S. Provisional Application No. 60/487,510, filed Jul. 15, 2003, which claims priority under 35 U.S.C. 119 GERMANY 10308355.3 filed Feb. 27, 2003.

The invention relates to arylcycloalkyl-substituted alkanoic acid derivatives and to their physiologically acceptable salts and physiologically functional derivatives.

Compounds of a similar structure have already been described in the prior art for the treatment of hyperlipidemia and diabetes (WO 2000/64876).

It was an object of the invention to provide compounds which permit a therapeutically exploitable modulation of the lipid and/or carbohydrate metabolism and are thus suitable for the prevention and/or treatment of disorders such as type 2 diabetes and atherosclerosis and their multifarious sequelae.

Surprisingly, a number of compounds which modulate the activity of PPAR receptors have been found. The compounds are particularly suitable for activating PPARalpha and PPARgamma, where the extent of the relative activation may vary, depending on the compounds.

The invention thus relates to compounds of the formula I

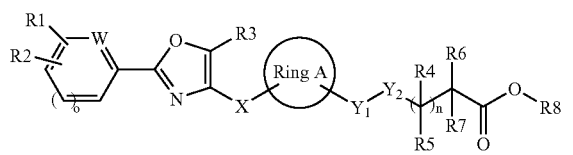

I wherein:

Ring A is (C3-C8)-cycloalkanediyl or (C3-C8)-cycloalkenediyl, wherein one or more carbon atoms of said (C3-C8)-cycloalkanediyl and (C3-C8)-cycloalkenediyl groups are optionally replaced by oxygen atoms;

R1, R2 are each independently H, F, Cl, Br, $CF_3$, $OCF_3$, (C1-C6)-alkyl, O-(C1-C6)-alkyl, $SCF_3$, $SF_5$, $OCF_2$-$CHF_2$, (C6-C10)-aryl, (C6-C10)-aryloxy, OH or $NO_2$; or R1 and R2, taken together with the atoms of the phenyl, pyridine, 1-H-pyrrole, thiophene or furan rings to which they are attached, form a fused, partially saturated or unsaturated, bicyclic (C6-C10)-aryl or (C5-C11)-heteroaryl group;

R3 is H, (C1-C6)-alkyl, (C3-C8)-cycloalkyl, (C1-C3)-alkyl-(C3-C8)-cycloalkyl, phenyl, (C1-C3)-alkyl-phenyl, (C5-C6)-heteroaryl, (C1-C3)-alkyl-(C5-C6)-heteroaryl or (C1-C3)-alkyl which is fully or partially substituted by F;

W is CH or N, if o =1;

W is O, S or NR9, if o=0;

X is (C1-C6)-alkanediyl, wherein one or more carbon atoms of said (C1-C6)-alkanediyl group are optionally replaced by oxygen atoms;

Y1 is O;

Y2 is CR12R13, SO or $SO_2$;

n is 0, 1 or 2;

R4 is H, F or (C1-C6)-alkyl;

R5 is H, F or (C1-C6)-alkyl;

R6 is H or (C1-C6)-alkyl; or is F if n is not 0;

R7 is H, (C1-C6)-alkyl, (C2-C6)-alkenyl, (C2-C6)-alkynyl, O-(C1-C6)-alkyl, O-(C2-C6)-alkenyl, O-(C2-C6)-alkynyl, (C3-C8)-cycloalkyl, phenyl, (C5-C11)-heteroaryl, O-(C3-C8)-cycloalkyl or O-phenyl, wherein said (C1-C6)-alkyl, (C2-C6)-alkenyl, (C2-C6)-alkynyl, O-(C1-C6)-alkyl, O-(C2-C6)-alkenyl, O-(C2-C6)-alkynyl, O-(C3-C8)-cycloalkyl and O-phenyl groups are optionally substituted by OH, NR10R11, O-(C1-C6)-alkyl, O-(C2-C6)-alkenyl, O-(C2-C6)-alkynyl, O-(C3-C8)-cycloalkyl, O-phenyl or O-(C5-C11)-heteroaryl, and said (C3-C8)-cycloalkyl, phenyl and (C5-C11)-heteroaryl groups are optionally substituted by OH, NR10R11, O-(C1-C6)-alkyl, O-(C2-C6)-alkenyl, O-(C2-C6)-alkynyl, O-(C3-C8)-cycloalkyl, O-phenyl, O-(C5-C11)-heteroaryl or (C1-C6)-alkyl, wherein said (C1-C6)-alkyl substituent is optionally substituted by F (fully or partially) or O-(C1-C6)-alkyl, wherein said O-(C1-C6)-alkyl substituent is optionally substituted by F (fully or partially), Cl, Br, I, OH, NR10R11, CO-(C1-C6)-alkyl, CO-(C6-C10)-aryl, CO-(C1-C6)-alkyl-(C6-C10)-aryl, CO-(C5-C11)-heteroaryl, C(O)-O-(C1-C6)-alkyl, C(O)—O-(C1-C6)-alkyl-(C6-C10)-aryl, C(O)—O-(C6-C10)-aryl, C(O)—O-(C5-C11)-heteroaryl, $SO_2$-(C1-C6)-alkyl, $SO_2$-(C1-C6)-alkyl-(C6-C10)-aryl, $SO_2$-(C1-C6)-alkyl-$SO_2$-(C1-C6)-alkyl, $SO_2$-(C6-C10)-aryl, $SO_2$-(C5-C11)-heteroaryl; or R6 and R7, together with the carbon atom to which they are attached, form a (C3-C8)-cycloalkyl group;

R8 is H or (C1-C6)-alkyl;

R9 is H or (C1-C6)-alkyl which is optionally substituted by phenyl;

R10 is H or (C1-C6)-alkyl which is optionally substituted by phenyl;

R11 is H or (C1-C6)-alkyl which is optionally substituted by phenyl;

R12 is H or (C1-C6)-alkyl;

R13 is H or (C1-C6)-alkyl;

and pharmaceutically acceptable salts thereof.

Preference is given to compounds of the formula I wherein:

Ring A is ($C_3$-$C_8$)-cycloalkanediyl or ($C_3$-$C_8$)-cycloalkenediyl, wherein one or more of the carbon atoms in said ($C_3$-$C_8$)-cycloalkanediyl or ($C_3$-$C_8$)-cycloalkenediyl groups are optionally replaced by oxygen atoms;

X is (C1-C6)-alkanediyl, wherein the C1 or C2 carbon atom (with respect to Ring A) in said (C1-C6)-alkanediyl group is optionally replaced by an oxygen atom;

and pharmaceutically acceptable salts thereof.

Particular preference is given to compounds of the formula I in which one or more radicals are as defined below:

Ring A is cyclohexane-1,3-diyl;

R1 is F, Br, $CF_3$, $OCF_3$, (C1-C6)-alkyl, O-(C1-C6)-alkyl or phenyl;

R1 is located in a position meta- or para- to the carbon atom of the phenyl ring that is attached to the oxazol ring;

R2 is hydrogen; or

R1 and R2, taken together with the phenyl ring to which they are attached, form naphthyl;

R3 is H, (C1-C6)-alkyl, (C3-C8)-cycloalkyl, (C1-C3)-alkyl-(C5-C6)-cycloalkyl, phenyl or (C1-C3)-alkyl-phenyl;
W is CH, if o=1;
X is $CH_2$—O or $CH_2$—O—$CH_2$;
n is 0;
R6 is H or (C1-C6)-alkyl;
R7 is H, (C1-C6)-alkyl, (C2-C6)-alkenyl, (C2-C6)-alkynyl, O-(C1-C6)-alkyl, O-(C2-C6)-alkenyl, O-(C2-C6)-alkynyl, (C3-C8)-cycloalkyl, phenyl, O-(C3-C8)-cycloalkyl, O-phenyl, (C5-C11)-heteroaryl,
  wherein said (C1-C6)-alkyl, (C2-C6)-alkenyl, (C2-C6)-alkynyl, O-(C1-C6)-alkyl, O-(C2-C6)-alkenyl, O-(C2-C6)-alkynyl, O-(C3-C8)-cycloalkyl, and O-phenyl groups are optionally substituted by OH, NR10R11, O-(C1-C6)-alkyl, O-(C2-C6)-alkenyl, O-(C2-C6)-alkynyl, O-(C3-C8)-cycloalkyl, O-phenyl or O-(C5-C11)-heteroaryl, and
  said (C3-C8)-cycloalkyl, phenyl and (C5-C11)-heteroaryl groups are optionally substituted by OH, NR10R11, O-(C1-C6)-alkyl, O-(C2-C6)-alkenyl, O-(C2-C6)-alkynyl, O-(C3-C8)-cycloalkyl, O-phenyl or O-(C5-C11)-heteroaryl or (Cl-C6)-alkyl,
    wherein said (C1-C6)-alkyl substituent is optionally substituted by F (fully or partially) or O-(C1-C6)-alkyl,
      wherein said O-(C1-C6)-alkyl substituent is optionally substituted by F (fully or partially), Cl, Br, I, OH, NR10R11; or
R6 and R7, taken together with the carbon atom to which they are attached, form (C3-C6)-cycloalkyl, in particular cyclopentyl;
R10 and R11 are each independently H or (C1-C6)-alkyl;
R12 and R13 are hydrogen.

Particular preference is furthermore given to the compounds of the formula I in which
R7 is H, (C1-C6)-alkyl, (C2-C6)-alkenyl, (C2-C6)-alkynyl, O-(C1-C6)-alkyl, O-(C2-C6)-alkenyl, O-(C2-C6)-alkynyl, (C3-C8)-cycloalkyl, phenyl or (C5-C 11)-heteroaryl,
  wherein said (C1-C6)-alkyl, (C2-C6)-alkenyl, (C2-C6)-alkynyl, O-(C1-C6)-alkyl, O-(C2-C6)-alkenyl, O-(C2-C6)-alkynyl and (C3-C8)-cycloalkyl groups are optionally substituted by NR10R11, O-(C1-C6)-alkyl, O-(C2-C6)-alkenyl, O-(C2-C6)-alkynyl, O-(C3-C8)-cycloalkyl, O-phenyl or O-(C5-C11)-heteroaryl,
  and said phenyl and (C5-C11)-heteroaryl groups are optionally substituted by NR10R11, O-(C1-C6)-alkyl, O-(C2-C6)-alkenyl, O-(C2-C6)-alkynyl, O-(C3-C8)-cycloalkyl, O-phenyl, O-(C5-C11)-heteroaryl or (C1-C6)-alkyl,
    wherein said (Cl-C6)-alkyl substituent is optionally substituted by F (fully or partially) or O-(C1-C6)-alkyl,
      wherein said O-(C1-C6)-alkyl substituent is optionally substituted by F (fully or partially), Cl or NR10R11;

and pharmaceutically acceptable salts thereof.

Very particular preference is given to the compounds of the formula I
wherein
  Ring A is cis-cyclohexane-1,3-diyl;
  R1, R2 are each independently H, F, CF3, (C1-C6)-alkyl, O-(C1-C6)-alkyl or phenyl, or
  R1 and R2, taken together with the phenyl ring to which they are attached, form naphthyl;
  R3 is (C1-C6)-alkyl;
  W is CH, if o=1;
  X is (CH2)O or CH2-O—CH2;
  Y1 is 0;
  Y2 is CH2;
  n is 0 or 1;
  R4 is H;
  R5 is H;
  R6 is H;
  R7 is H, (C1-C6)-alkyl, O-(C1-C6)-alkyl, (C1-C6)-alkyl-O-(C1-C6)-alkyl, O-(C2-C6)-alkenyl, O-(C2-C6)-alkynyl or CH2NR10R11,
    wherein said (C1-C6)-alkyl, O-(C1-C6)-alkyl and O-(C2-C6)-alkenyl groups are optionally substituted by phenyl or (C5-C6)-heteroaryl,
      wherein said phenyl and (C5-C6)-heteroaryl substituents are optionally substituted by (C1-C6)-alkyl, O-(C1-C6)-alkyl or CF3; or
  R6 and R7, together with the carbon atom to which they are attached, form (C3-C6)-cycloalkyl;
  R8 is H;
  R10 is (C1-C6)-alkyl;
  R11 is (C1-C6)-alkyl which is substituted by phenyl;

and pharmaceutically acceptable salts thereof.

The alkyl radicals in the substituents R1, R2, R3, R4, R5, R6, R7, R8, R9, R10, R11, R12 and R13 may be either straight-chain or branched.

Aryl means an aromatic carbocyclic mono- or bicyclic ring system which comprises 6 to 10 atoms in the ring or rings.

Heteroaryl is a mono- or bicyclic aromatic ring system having 4 to 11 ring members, in which at least one atom in the ring system is a heteroatom from the series N, O and S.

The compounds of the formula I comprise at least two centers of asymmetry and may comprise more in addition. The compounds of the formula I may therefore exist in the form of their racemates, racemic mixtures, pure enantiomers, diastereomers and mixtures of diastereomers. The present invention encompasses all these isomeric forms of the compounds of the formula I. These isomeric forms can be obtained by known methods even if not specifically described in some cases.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts), alkaline earth metal salts (such as magnesium and calcium salts), and salts of trometamol (2-amino-2-hydroxymethyl-1,3-propanediol), diethanolamine, lysine or ethylenediamine.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

As used herein, the following definitions apply:

"Patient" means a warm blooded animal, such as for example rat, mice, dogs, cats, guinea pigs, and primates such as humans.

"Treat" or "treating" means to alleviate symptoms, eliminate the causation of the symptoms either on a temporary or permanent basis, or to prevent or slow the appearance of symptoms of the named disorder or condition.

"Therapeutically effective amount" means a quantity of the compound which is effective in treating the named disorder or condition.

"Pharmaceutically acceptable carrier" is a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

The term "physiologically functional derivative" used herein refers to any physiologically tolerated derivative of a compound of the formula I of the invention, for example an ester, which on administration to a mammal such as, for example, a human is able to form (directly or indirectly) a compound of the formula I or an active metabolite thereof.

Physiologically functional derivatives also include prodrugs of the compounds of the invention, as described, for example, in H. Okada et al., Chem. Pharm. Bull. 1994, 42, 57-61. Such prodrugs can be metabolized in vivo to a compound of the invention. These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I" hereinafter refer to compound(s) of the formula I as described above, and their salts, solvates and physiologically functional derivatives as described herein.

Use

This invention relates further to the use of compounds of the formula I and their pharmaceutical compositions as PPAR ligands. The PPAR ligands of the invention are suitable as modulators of PPAR activity.

Peroxisome proliferator-activated receptors (PPAR) are transcription factors which can be activated by ligands and belong to the class of nuclear hormone receptors. There are three PPAR isoforms, PPARalpha, PPARgamma and PPARdelta, which are encoded by different genes (Peroxisome proliferator-activated receptor (PPAR): structure, mechanisms of activation and diverse functions: Motojima K, Cell Struct Funct. 1993 Oct; 18(5): 267-77).

Two variants of PPARgamma exist, PPARgamma$_1$ and gamma$_2$, which are the result of alternative use of promoters and differential mRNA splicing (Vidal-Puig et al. J. Clin. Invest., 97:2553-2561, 1996). Different PPARs have different tissue distribution and modulate different physiological functions. The PPARs play a key role in various aspects of the regulation of a large number of genes, the products of which genes are directly or indirectly crucially involved in lipid and carbohydrate metabolism. Thus, for example, PPARalpha receptors play an important part in the regulation of fatty acid catabolism or lipoprotein metabolism in the liver, while PPARgamma is crucially involved for example in regulating adipose cell differentiation. In addition, however, PPARs are also involved in the regulation of many other physiological processes, including those which are not directly connected with carbohydrate or lipid metabolism. The activity of different PPARs can be modulated by various fatty acids, fatty acid derivatives and synthetic compounds to varying extents. For relevant reviews about functions, physiological effect and pathophysiology, see: Joel Berger et al., Annu. Rev. Med. 2002, 53, 409-435; Timothy Wilson et al. J. Med. Chem., 2000, Vol. 43, No. 4, 527-550; Steven Kliewer et al., Recent Prog Horm Res. 2001; 56: 239-63.

The present invention relates to compounds of the formula I suitable for modulating the activity of PPARs, especially the activity of PPARalpha and PPARgamma. Depending on the modulation profile, the compounds of the formula I are suitable for the treatment, control and prophylaxis of the indications described hereinafter, and for a number of other pharmaceutical applications connected thereto (see, for example, Joel Berger et al., Annu. Rev. Med. 2002, 53, 409-435; Timothy Wilson et al. J. Med. Chem., 2000, Vol. 43, No. 4, 527-550; Steven Kliewer et al., Recent Prog Horm Res. 2001; 56: 239-63; Jean-Charles Fruchart, Bart Staels and Patrick Duriez: PPARS, Metabolic Disease and Arteriosclerosis, Pharmacological Research, Vol. 44, No. 5, 345-52; 2001; Sander Kersten, Beatrice Desvergne & Walter Wahli: Roles of PPARs in health and disease, NATURE, VOL 405, 25 MAY 2000; 421-4; Ines Pineda Torra, Giulia Chinetti, Caroline Duval, Jean-Charles Fruchart and Bart Staels: Peroxisome proliferator-activated receptors: from transcriptional control to clinical practice, Curr Opin Lipidol 12: 2001, 245-254).

Compounds of this type are particularly suitable for the treatment and/or prevention of 1. disorders of fatty acid metabolism and glucose utilization disorders disorders in which insulin resistance is involved 2. Diabetes mellitus, especially type 2 diabetes, including the prevention of the sequelae associated therewith.

Particular aspects in this connection are hyperglycemia, improvement in insulin resistance, improvement in glucose tolerance, protection of the pancreatic β cells prevention of macro- and microvascular disorders 3. Dyslipidemias and their sequelae such as, for example, atherosclerosis, coronary heart disease, cerebrovascular disorders etc, especially those (but not restricted thereto) which are characterized by one or more of the following factors:

high plasma triglyceride concentrations, high postprandial plasma triglyceride concentrations, low HDL cholesterol concentrations low ApoA lipoprotein concentrations high LDL cholesterol concentrations small dense LDL cholesterol particles high ApoB lipoprotein concentrations 4. Various other conditions which may be associated with the metabolic syndrome, such as:

obesity (excess weight), including central obesity thromboses, hypercoagulable and prothrombotic states (arterial and venous)

high blood pressure heart failure such as, for example (but not restricted thereto), following myocardial infarction, hypertensive heart disease or cardiomyopathy 5. Other disorders or conditions in which inflammatory reactions or cell differentiation may for example be involved are:
atherosclerosis such as, for example (but not restricted thereto), coronary sclerosis including angina pectoris or myocardial infarction, stroke
vascular restenosis or reocclusion
chronic inflammatory bowel diseases such as, for example, Crohn's disease and ulcerative colitis
pancreatitis
other inflammatory states
retinopathy
adipose cell tumors
lipomatous carcinomas such as, for example, liposarcomas
solid tumors and neoplasms such as, for example (but not restricted thereto), carcinomas of the gastrointestinal tract, of the liver, of the biliary tract and of the pancreas, endocrine tumors, carcinomas of the lungs, of the kidneys and the urinary tract, of the genital tract, prostate carcinomas etc
acute and chronic myeloproliferative disorders and lymphomas
angiogenesis
neurodegenerative disorders
Alzheimer's disease
multiple sclerosis
Parkinson's disease
erythemato-squamous dermatoses such as, for example, psoriasis
acne vulgaris
other skin disorders and dermatological conditions which are modulated by PPAR
eczemas and neurodermitis
dermatitis such as, for example, seborrheic dermatitis or photodermatitis
keratitis and keratoses such as, for example, seborrheic keratoses, senile keratoses, actinic keratosis, photo-induced keratoses or keratosis follicularis
keloids and keloid prophylaxis
warts, including condylomata or condylomata acuminata
human papilloma viral (HPV) infections such as, for example, venereal papillomata, viral warts such as, for example, molluscum contagiosum, leukoplakia
papular dermatoses such as, for example, Lichen planus
skin cancer such as, for example, basal-cell carcinomas, melanomas or cutaneous T-cell lymphomas
localized benign epidermal tumors such as, for example, keratoderma, epidermal naevi
chilblains
high blood pressure
syndrome X
polycystic ovary syndrome (PCOS)
asthma
osteoarthritis
lupus erythematosus (LE) or inflammatory rheumatic disorders such as, for example, rheumatoid arthritis
vasculitis
wasting (cachexia)
gout
ischemia/reperfusion syndrome
acute respiratory distress syndrome (ARDS)

Formulations

The amount of a compound of formula I necessary to achieve the desired biological effect depends on a number of factors, for example the specific compound chosen, the intended use, the mode of administration and the clinical condition of the patient. The daily dose is generally in the range from 0.001 mg to 100 mg (typically from 0.01 mg to 50 mg) per day and per kilogram of bodyweight, for example 0.1-10 mg/kg/day. An intravenous dose may be, for example, in the range from 0.001 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampules for injections may contain, for example, from 1 mg to 100 mg, and single-dose formulations which can be administered orally, such as, for example, capsules or tablets, may contain, for example, from 0.05 to 1000 mg, typically from 0.5 to 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical preparations for oral administration may be in the form of separate units such as, for example, capsules, cachets, suckable tablets or tablets, each of which contain a defined amount of the compound of formula I; as powders or granules, as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surface-active/dispersing agent(s) in a suitable machine. Molded tablets can be produced by molding the compound, which is in powder form and is moistened with an inert liquid diluent, in a suitable machine.

Pharmaceutical compositions which are suitable for per-oral (sublingual) administration comprise suckable tablets which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula 1, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of the formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single plasters which are suitable for long-term close contact with the patient's epidermis. Such plasters suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

The compounds of the formula I are distinguished by favorable effects on metabolic disorders. They beneficially influence lipid and sugar metabolism, in particular they lower the triglyceride level and are suitable for the prevention and treatment of type II diabetes and arteriosclerosis and the diverse sequalae thereof.

Combinations with Other Medicaments

The compounds of the invention can be administered alone or in combination with one or more further pharmacologically active substances which have, for example, favorable effects on metabolic disturbances or disorders frequently associated therewith. Examples of such medicaments are 1. medicaments which lower blood glucose, antidiabetics,
2. active ingredients for the treatment of dyslipidemias,
3. antiatherosclerotic medicaments,
4. antiobesity agents,
5. antiinflammatory active ingredients
6. active ingredients for the treatment of malignant tumors
7. antithrombotic active ingredients
8. active ingredients for the treatment of high blood pressure
9. active ingredients for the treatment of heart failure and
10. active ingredients for the treatment and/or prevention of complications caused by diabetes or associated with diabetes.

They can be combined with the compounds of the invention of the formula I in particular for a synergistic improvement in the effect. Administration of the active ingredient combination can take place either by separate administration of the active ingredients to the patient or in the form of combination products in which a plurality of active ingredients are present in one pharmaceutical preparation.

Examples which may be mentioned are:

Antidiabetics

Suitable antidiabetics are disclosed for example in the Rote Liste 2001, chapter 12 or in the USP Dictionary of USAN and International Drug Names, US Pharmacopeia, Rockville 2001. Antidiabetics include all insulins and insulin derivatives such as, for example, Lantus® (see www-.lantus.com) or Apidra®, and other fast-acting insulins (see U.S. Pat. No. 6,221,633), GLP-1 receptor modulators as described in WO 01/04146 or else, for example, those disclosed in WO 98/08871 of Novo Nordisk A/S.

The orally effective hypoglycemic active ingredients include, preferably, sulfonylureas, biguanides, meglitinides, oxadiazolidinediones', thiazolidinediones, glucosidase inhibitors, glucagon antagonists, GLP-1 agonists, DPP-IV inhibitors, potassium channel openers such as, for example, those disclosed in WO 97/26265 and WO 99/03861, insulin sensitizers, inhibitors of liver enzymes involved in the stimulation of gluconeogenesis and/or glycogenolysis, modulators of glucose uptake, compounds which alter lipid metabolism and lead to a change in the blood lipid composition, compounds which reduce food intake, PPAR and PXR modulators and active ingredients which act on the ATP-dependent potassium channel of the beta cells.

In one embodiment of the invention, the compounds of the formula I are administered in combination with insulin.

In one embodiment of the invention, the compounds of the formula I are administered in combination with substances which influence hepatic glucose production such as, for example, glycogen phosphorylase inhibitors (see: WO 01/94300, WO 02/096864, WO 03/084923, WO 03/084922, WO 03/104188)

In one embodiment, the compounds of the formula I are administered in combination with a sulfonylurea such as, for example, tolbutamide, glibenclamide, glipizide or glimepiride.

In one embodiment, the compounds of the formula I are administered in combination with an active ingredient which acts on the ATP-dependent potassium channel of the beta cells, such as, for example, tolbutamide, glibenclamide, glipizide, glimepiride or repaglinide.

In one embodiment, the compounds of the formula I are administered in combination with a biguanide such as, for example, metformin.

In a further embodiment, the compounds of the formula I are administered in combination with a meglitinide such as, for example, repaglinide.

In one embodiment, the compounds of the formula I are administered in combination with a thiazolidinedione such as, for example, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy ]phenyl]methyl]-2,4-thiazolidinedione.

In one embodiment, the compounds of the formula I are administered in combination with a DPPIV inhibitor as described, for example, in WO98/19998, WO 99/61431, WO 99/67278, WO 99/67279, WO01/72290, WO 02/38541, WO03/040174, in particular P 93/01 (1-cyclopentyl-3-methyl-1-oxo-2-pentanammonium chloride), P-31/98, LAF237 (1-[2-[3-hydroxyadamant-1-ylamino)acetyl]pyrrolidine-2-(S)-carbonitrile), TS021 ((2S, 4S)-4-fluoro-1-[[(2-hydroxy-1,1-dimethylethyl)amino]-acetyl]pyrrolidine-2-carbonitrile monobenzenesulfonate).

In one embodiment of the invention, the compounds of the formula I are administered in combination with a PPAR-gamma agonist such as, for example, rosiglitazone, pioglitazone.

In one embodiment, the compounds of the formula I are administered in combination with compounds with an inhibitory effect on SGLT-1 and/or 2, as disclosed directly or indirectly for example in PCT/EP03/06841, PCT/EP03/13454 and PCT/EP03/13455.

In one embodiment, the compounds of the formula I are administered in combination with an a-glucosidase inhibitor such as, for example, miglitol or acarbose.

In one embodiment, the compounds of the formula I are administered in combination with more than one of the aforementioned compounds, e.g. in combination with a sulfonylurea and mefformin, a sulfonylurea and acarbose, repaglinide and mefformin, insulin and a sulfonylurea, insulin and mefformin, insulin and troglitazone, insulin and lovastatin, etc.

Lipid Modulators

In one embodiment of the invention, the compounds of the formula I are administered in combination with an HMGCOA reductase inhibitor such as lovastatin, fluvastatin, pravastatin, simvastatin, ivastatin, itavastatin, atorvastatin, rosuvastatin.

In one embodiment of the invention, the compounds of the formula I are administered in combination with a bile acid reabsorption inhibitor (see, for example, U.S. Pat. No. 6,245,744, U.S. Pat. No. 6,221,897, U.S. Pat. No. 6,277,831, EP 0683 773, EP 0683 774).

In one embodiment of the invention, the compounds of the formula I are administered in combination with a polymeric bile acid adsorbent such as, for example, cholestyramine, colesevelam.

In one embodiment of the invention, the compounds of the formula I are administered in combination with a cholesterol absorption inhibitor as described for example in WO 0250027, or ezetimibe, tiqueside, pamaqueside.

In one embodiment of the invention, the compounds of the formula I are administered in combination with an LDL receptor inducer (see, for example, U.S. Pat. No. 6,342,512).

In one embodiment, the compounds of the formula I are administered in combination with bulking agents, preferably insoluble bulking agents (see, for example, carob/Caromax® (Zunft H J; et al., Carob pulp preparation for treatment of hypercholesterolemia, ADVANCES IN THERAPY (2001 September-October), 18(5), 230-6. ) Caromax is a carob-containing product from Nutrinova, Nutrition Specialties & Food Ingredients GmbH, Industriepark Hoechst, 65926 Frankfurt/Main)). Combination with Caromax® is possible in one preparation or by separate administration of compounds of the formula I and Caromax®. Caromax® can in this connection also be administered in the form of food products such as, for example, in bakery products or muesli bars.

In one embodiment of the invention, the compounds of the formula I are administered in combination with a PPA-Ralpha agonist.

In one embodiment of the invention, the compounds of the formula I are administered in combination with a mixed PPAR alpha/gamma agonist such as, for example, AZ242 (Tesaglitazar, (S)-3-(4-[2-(4-methanesulfonyloxyphenyl)ethoxy]phenyl)-2-ethoxypropionic acid), BMS 298585 (N-[(4-methoxyphenoxy)carbonyl]-N-[[4-[2-(5-methyl-2-phenyl-4-oxazolyl)ethoxy]phenyl]methyl]glycine) or as described in WO 99/62872, WO 99/62871, WO 01/40171, WO 01/40169, WO96/38428, WO 01/81327, WO 01/21602, WO 03/020269, WO 00/64888 or WO 00/64876.

In one embodiment of the invention, the compounds of the formula I are administered in combination with a fibrate such as, for example, fenofibrate, gemfibrozil, clofibrate, bezafibrate.

In one embodiment of the invention, the compounds of the formula I are administered in combination with nicotinic acid or niacin.

In one embodiment of the invention, the compounds of the formula I are administered in combination with a CETP inhibitor, e.g. CP-529, 414 (torcetrapib).

In one embodiment of the invention, the compounds of the formula I are administered in combination with an ACAT inhibitor.

In one embodiment of the invention, the compounds of the formula I are administered in combination with an MTP inhibitor such as, for example, implitapide.

In one embodiment of the invention, the compounds of the formula I are administered in combination with an antioxidant.

In one embodiment of the invention, the compounds of the formula I are administered in combination with a lipoprotein lipase inhibitor.

In one embodiment of the invention, the compounds of the formula I are administered in combination with an ATP citrate lyase inhibitor.

In one embodiment of the invention, the compounds of the formula I are administered in combination with a squalene synthetase inhibitor.

In one embodiment of the invention, the compounds of the formula I are administered in combination with a lipoprotein(a) antagonist.

Antiobesity agents

In one embodiment of the invention, the compounds of the formula I are administered in combination with a lipase inhibitor such as, for example, orlistat.

In one embodiment, the further active ingredient is fenfluramine or dexfenfluramine.

In another embodiment, the further active ingredient is sibutramine.

In a further embodiment, the compounds of the formula I are administered in combination with CART modulators (see "Cocaine-amphetamine-regulated transcript influences energy metabolism, anxiety and gastric emptying in mice" Asakawa, A, et al., M.: Hormone and Metabolic Research (2001), 33(9), 554-558), NPY antagonists, e.g. naphthalene-1-sulfonic acid {4-[(4-aminoquinazolin-2-ylamino)methyl]-cyclohexylmethyl }amide hydrochloride (CGP 71683A)), MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1 -(4-chlorophenyl)-2-oxoethyl]-amide; (WO 01/91752)), orexin antagonists (e.g. 1-(2-methylbenzoxazol-6-yl)-3-[1,5]naphthyridin-4-ylurea hydrochloride (SB-334867-A)), H3 agonists (3-cyclohexyl-1-(4,4-dimethyl-1,4,6,7-tetrahydroimidazo[4,5-c]pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl ]dipropylamine (WO 00/66585)), CRF BP antagonists (e.g. urocortin), urocortin agonists, β3 agonists (e.g. 1-(4-chloro-3-methanesulfonylmethylphenyl)-2-[2-(2,3-dimethyl-1H-indol-6-yloxy)ethylamino ]-ethanol hydrochloride (WO 01/83451)), MSH (melanocyte-stimulating hormone) agonists, CCK-A agonists (e.g. {2-[4-(4-chloro-2,5-dimethoxyphenyl)-5-(2-cyclohexylethyl)thiazol-2-ylcarbamoyl]-5,7-dimethylindol-1-yl }acetic acid trifluoroacetic acid salt (WO 99/15525)), serotonin reuptake inhibitors (e.g. dexfenfluramine), mixed serotoninergic and noradrenergic compounds (e.g. WO 00/71549), 5HT agonists e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethylcarbamoyl)-3,4-dihydro-1H-isoquinoline-2-carboxylic acid tertiary butyl ester (WO 01/85695)), TRH agonists (see, for example, EP 0 462 884), uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881), DA agonists (bromocriptine, Doprexin), lipase/amylase inhibitors (e.g. WO 00/40569), PPAR modulators (e.g. WO 00/78312), RXR modulators or TR-β agonists.

In one embodiment of the invention, the further active ingredient is leptin.

In one embodiment, the further active ingredient is dexamphetamine, amphetamine, mazindole or phentermine.

In one embodiment, the compounds of the formula I are administered in combination with medicaments having effects on the coronary circulation and the vascular system, such as, for example, ACE inhibitors (e.g. ramipril), medicaments which act on the angiotensin-renine system, calcium antagonists, beta blockers etc.

In one embodiment, the compounds of the formula I are administered in combination with medicaments having an antiinflammatory effect.

In one embodiment, the compounds of the formula I are administered in combination with medicaments which are employed for cancer therapy and cancer prevention.

It will be appreciated that every suitable combination of the compounds of the invention with one or more of the aforementioned compounds and optionally one or more other pharmacologically active substances is regarded as falling within the protection conferred by the present invention.

The activity of the compounds was tested as follows:

Determination of EC50 Values of PPAR agonists in the Cellular PPARalpha Assay

Principle

The potency of substances which bind to human PPARA and activate in an agonistic manner is analyzed using a stably transfected HEK cell line (HEK =human embryo kidney) which is referred to here as PPARalpha reporter cell line. It contains two genetic elements, a luciferase reporter element (pδM-GAL4-Luc-Zeo) and a PPARalpha fusion protein (GR-GAL4-humanPPARα-LBD) which mediates expression of the luciferase reporter element depending on a PPARalpha ligand. The stably and constitutively expressed fusion protein GR-GAL4-humanPPARalpha-LBD binds in the cell nucleus of the PPARalpha reporter cell line via the GAL4 protein portion to the GAL4 DNA binding motifs 5'-upstream of the luciferase reporter element which is integrated in the genome of the cell line. There is only little expression of the luciferase reporter gene without addition of a PPARalpha ligand if fatty acid-depleted fetal calf serum (cs-FCS) is used in the assay. PPARα ligands bind and activate the PPARα fusion protein and thereby bring about expression of the luciferase reporter gene. The luciferase which is formed can be detected by means of chemiluminescence via an appropriate substrate.

Construction of the Cell Line

The PPARalpha reporter cell line was prepared in 2 stages. Firstly, the luciferase reporter element was constructed and stably transfected into HEK cells. For this purpose, five binding sites of the yeast transcription factor GAL4 (each 5'-CGGAGTACTGTCCTCCGAG-3') (SEQ ID No. 1) were cloned in 5'-upstream of a 68 bp-long minimal MMTV promoter (Genbank Accession # V01 175). The minimal MMTV promoter section contains a CCAAT box and a TATA element in order to enable efficient transcription by RNA polymerase 11. The cloning and sequencing of the GAL4-MMTV construct took place in analogy to the description of Sambrook J. et. al. (Molecular cloning, Cold Spring Harbor Laboratory Press, 1989). Then the complete Photinus pyralis gene (Genbank Accession # M15077) was cloned in 3'-downstream of the GAL4-MMTV element. After sequencing, the luceriferase reporter element consisting of five GAL4 binding sites, MMTV promoter and luciferase gene was recloned into a plasmid which confers zeocin resistance in order to obtain the plasmid pδM-GAL4-Luc-Zeo. This vector was transfected into HEK cells in accordance with the statements in Ausubel, F. M. et al. (Current protocols in molecular biology, Vol. 1-3, John Wiley & Sons, Inc., 1995). Then zeocin-containing medium (0.5 mg/ml) was used to select a suitable stable cell clone which showed very low basal expression of the luceriferase gene.

In a second step, the PPARalpha fusion protein (GR-GAL4-humanPPARalpha-LBD was introduced into the stable cell clone described. For this purpose, initially the cDNA coding for the N-terminal 76 amino acids of the glucocorticoid receptor (Genbank Accession # P04150) was linked to the cDNA section coding for amino acids 1-147 of the yeast transcription factor GAL4 (Genbank Accession # P04386). The cDNA of the ligand-binding domain of the human PPARalpha receptor (amino acids S167-Y468; Genbank Accession # S74349) was cloned in at the 3'-end of this GR-GAL4 construct. The fusion construct prepared in this way (GR-GAL4-humanPPARalpha-LBD) was recloned into the plasmid pcDNA3 (from Invitrogen) in order to enable constitutive expression therein by the cytomegalovirus promoter. This plasmid was linearized with a restriction endonuclease and stably transfected into the previously described cell clone containing the luciferase reporter element. The finished PPARalpha reporter cell line which contains a luciferase reporter element and constitutively expresses the PPARalpha fusion protein (GR-GAL4-human PPARalpha-LBD) was isolated by selection with zeocin (0.5 mg/ml) and G418 (0.5 mg/ml).

Assay Procedure

The activity of PPARalpha agonists is determined in a 3-day assay which is described below:

Day 1

The PPARα-reporter cell line is cultivated to 80% confluence in DMEM (#41965-039, Invitrogen) which is mixed with the following additions: 10% cs-FCS (fetal calf serum; #SH-30068.03, Hyclone), 0.5 mg/ml zeocin (#R250-01, Invitrogen), 0.5 mg/ml G418 (#10131-027, Invitrogen), 1% penicillin-streptomycin solution (#15140-122, Invitrogen) and 2 mM L-glutamine (#25030-024, Invitrogen). The cultivation takes place in standard cell culture bottles (# 353112, Becton Dickinson) in a cell culture incubator at 37° C. in the presence of 5% $CO_2$. The 80% -confluent cells are washed once with 15 ml of PBS (#14190-094, Invitrogen), treated with 3 ml of trypsin solution (#25300-054, Invitrogen) at 37° C. for 2 min, taken up in 5 ml of the DMEM described and counted in a cell counter. After dilution to 500.000 cells/ml, 35,000 cells are seeded in each well of a 96 well microtiter plate with a clear plastic base (#3610, Corning Costar). The plates are incubated in the cell culture incubator at 37° C. and 5% $CO_2$ for 24 h.

Day 2

PPARalpha agonists to be tested are dissolved in DMSO in a concentration of 10 mM. This stock solution is diluted in DMEM (#41965-039, Invitrogen) which is mixed with 5% cs-FCS (#SH-30068.03, Hyclone), 2 mM L-glutamine (#25030-024, Invitrogen) and the previously described antibiotics (zeocin, G418, penicillin and streptomycin).

Test substances are tested in 11 different concentrations in the range from 10 μM to 100 pM. More potent compounds are tested in concentration ranges from 1 μM to 10 pM or between 100 nM and 1 pM.

The medium of the PPARalpha reporter cell line seeded on day 1 is completely removed by aspiration, and the test substances diluted in medium are immediately added to the cells. The dilution and addition of the substances is carried out by a robot (Beckman FX). The final volume of the test substances diluted in medium is 100 μl per well of a 96 well microtiter plate. The DMSO concentration in the assay is less than 0.1% v/v in order to avoid cytotoxic effects of the solvent.

Each plate was charged with a standard PPARalpha agonist, which was likewise diluted in 11 different concentrations, in order to demonstrate the functioning of the assay in each individual plate. The assay plates are incubated in an incubator at 37° C. and 5% $CO_2$ for 24 h.

Day 3

The PPARα reporter cells treated with the test substances are removed from the incubator, and the medium is aspirated off. The cells are lyzed by pipetting 50 μl of Bright Glo reagent (from Promega) into each well of a 96 well microtiter plate. After incubation at room temperature in the dark for 10 minutes, the microtiter plates are measured in the luminometer (Trilux from Wallac). The measuring time for each well of a microtiter plate is 1 sec.

Evaluation

The raw data from the luminometer are transferred into a Microsoft Excel file.

Dose-effect plots and EC50 values of PPAR agonists are calculated using the XL.Fit program as specified by the manufacturer (IDBS).

The PPARalpha EC50 values for the compounds of Examples 1 to 91 in this assay are in the range from 0.6 nM to >10 μM.

The results for the activity of some compounds of the invention of the formula I are indicated in Table I below:

TABLE 1

| Example No. | EC50 PPARalpha [nM] |
| --- | --- |
| 1 | 41 |
| 5 | 69 |
| 8 | 24 |
| 18 | 1.5 |
| 22 | 43 |
| 25 | 6.2 |
| 35 | 84 |
| 36 | 14 |
| 47 | 0.8 |
| 52 | 22 |
| 60 | 26 |
| 81 | 0.6 |
| 91 | 78 |

It is evident from Table I that the compounds of the invention of the formula I activate the PPARalpha receptor and thus bring about for example in analogy to fibrates in clinical use a lowering of triglycerides in the body (see, for example, J.-Ch. Fruchard et al.: PPARS, Metabolic Disease and Atherosclerosis, Pharmacological Research, Vol. 44, No. 5, 345-52, 2001; S. Kersten et al.: Roles of PPARs in health and disease, NATURE, VOL 405, 25 MAY 2000, 421-4; I. Pineda et al.: Peroxisome proliferator-activated receptors: from transcriptional control to clinical practice, Curr Opin Lipidol 12: 2001, 245-254).

Determination of EC50 Values of PPAR Agonists in the Cellular PPARgamma Assay

Principle

A transient transfection system is employed to determine the cellular PPARgamma activity of PPAR agonists. It is based on the use of a luciferase reporter plasmid (pGL3basic-5xGAL4-TK) and of a PPARgamma expression plasmid (pcDNA3-GAL4-humanPPARgammaLBD). Both plasmids are transiently transfected into human embryonic kidney cells (HEK cells). There is then expression in these cells of the fusion protein GAL4-humanPPARgammaLBD which binds to the GAL4 binding sites of the reporter plasmid. In the presence of a PPARgamma-active ligand, the activated fusion protein GAL4-humanPPARgammaLBD induces expression of the luciferase reporter gene, which can be detected in the form of a chemiluminescence signal after addition of a luciferase substrate. As a difference from the stably transfected PPARalpha reporter cell line, in the cellular PPARγ assay the two components (luciferase reporter plasmid and PPARgamma expression plasmid) are transiently transfected into HEK cells because stable and permanent expression of the PPARgamma fusion protein is cytotoxic.

Construction of the Plasmids

The luciferase reporter plasmid pGL3basic-5xGAL4-TK is based on the vector pGL3basic from Promega. The reporter plasmid is prepared by cloning five binding sites of the yeast transcription factor GAL4 (each binding site with the sequence 5'-CTCGGAGGACAGTACTCCG-3') (SEQ ID No. 2), together with a 160 bp-long thymidine kinase promoter section (Genbank Accession # AF027128) 5'-upstream into pGL3basic. 3'-downstream of the thymidine kinase promoter is the complete luciferase gene from Photinus pyralis (Genbank Accession # M15077) which is already a constituent of the plasmid pGL3basic used. The cloning and sequencing of the reporter plasmid pGL3basic- 5xGAL4-TK took place in analogy to the description in Sambrook J. et. al. (Molecular cloning, Cold Spring Harbor Laboratory Press, 1989).

The PPARgamma expression plasmid pcDNA3-GAL4-humanPPARγLBD was prepared by first cloning the cDNA coding for amino acids 1-147 of the yeast transcription factor GAL4 (Genbank Accession # P04386) into the plasmid pcDNA3 (from Invitrogen) 3'-downstream of the cytomegalovirus promoter. Subsequently, the cDNA of the ligand-binding domain (LBD) of the human PPARγ receptor (amino acids 1152-Y475; Accession # g1480099) 3'-downstream of the GAL4 DNA binding domain. Cloning and sequencing of the PPARgamma expression plasmid pcDNA3-GAL4-humanPPARgammaLBD again took place in analogy to the description in Sambrook J. et. al. (Molecular cloning, Cold Spring Harbor Laboratory Press, 1989). Besides the luciferase reporter plasmid pGL3basic-5× GAL4-TK and the PPARγ expression plasmid pcDNA3-GAL4-humanPPARgammaLBD, also used for the cellular PPARgamma assay are the reference plasmid PRL-CMV (from Promega) and the plasmid pBluescript SK(+) from Stratagene. All four plasmids were prepared using a plasmid preparation kit from Qiagen, which ensured a plasmid quality with a minimal endotoxin content, before transfection into HEK cells.

Assay Procedure

The activity of PPARgamma agonists is determined in a 4-day assay which is described below. Before the transfection, HEK cells are cultivated in DMEM (#41965-039, Invitrogen) which is mixed with the following additions: 10% FCS (#16000-044, Invitrogen), 1% penicillin-streptomycin solution (#15140-122, Invitrogen) and 2 mM L-glutamine (#25030-024, Invitrogen).

Day 1

Firstly, solution A, a transfection mixture which contains all four plasmids previously described in addition to DMEM, is prepared. The following amounts are used to make up 3 ml of solution A for each 96 well microtiter plate for an assay: 2622 μl of antibiotic- and serum-free DMEM (# 41965-039, Invitrogen), 100 μl of reference plasmid PRL-CMV (1 ng/μl), 100 μl of luciferase reporter plasmid pGL3basic-5xGAL4-TK (10 ng/pl), 100 μl of PPARγ expression plasmid pcDNA3-GAL4-humanPPARγLBD (100 ng/μl) and 78 μl of plasmid pBluescript SK(+) (500 ng/μl). Then 2 ml of solution B are prepared by mixing 1.9 ml of DMEM (# 41965-039, Invitrogen) with 100 μl of PolyFect transfection reagent (from Qiagen) for each 96 well microtiter plate. Subsequently, 3 ml of solution A are mixed with 2 ml of solution B to give 5 ml of solution C, which is thoroughly mixed by multiple pipetting and incubated at room temperature for 10 min.

80%-confluent HEK cells from a cell culture bottle with a capacity of 175 cm$^2$ are washed once with 15 ml of PBS (#14190-094, Invitrogen) and treated with 3 ml of trypsin solution (#25300-054, Invitrogen) at 37° C. for 2 min. The cells are then taken up in 15 ml of DMEM (#41965-039, Invitrogen) which is mixed with 10% FCS (# 16000-044, Invitrogen), 1% penicillin-streptomycin solution (#15140-122, Invitrogen) and 2 mM L-glutamine (#25030-024, Invitrogen). After the cell suspension has been counted in a cell counter, the suspension is diluted to 250,000 cells/ml. 15 ml of this cell suspension are mixed with 5 ml of solution C for one microtiter plate. 200 μl of the suspension are seeded in each well of a 96 well microtiter plate with a clear plastic base (#3610, Corning Costar). The plates are incubated in a cell culture incubator at 37° C. and 5% $CO_2$ for 24 h.

Day 2

PPAR agonists to be tested are dissolved in DMSO in a concentration of 10 mM. This stock solution is diluted in DMEM (# 41965-039, Invitrogen) which is mixed with 2% Ultroser (#12039-012, Biosepra), 1% penicillin-streptomycin solution (#15140-122, Invitrogen) and 2 mM L-glutamine (#25030-024, Invitrogen). Test substances are tested in a total of 11 different concentrations in the range from 10 μM to 100 pM. More potent compounds are tested in concentration ranges from 1 μM to 10 pM.

The medium of the HEK cells transfected and seeded on day 1 is completely removed by aspiration, and the test substances diluted in medium are immediately added to the cells. The dilution and addition of the substances is carried out by a robot (Beckman FX). The final volume of the test substances diluted in medium is 100 μl per well of a 96 well microtiter plate. Each plate is charged with a standard PPARγ agonist, which is likewise diluted in 11 different concentrations, in order to demonstrate the functioning of the assay in each individual plate. The assay plates are incubated in an incubator at 37° C. and 5% $CO_2$.

Day 4

After removal of the medium by aspiration, 50 μl of Dual-Glo ™ reagent (Dual-Glo™ Luciferase Assay System; Promega) are added to each well in accordance with the manufacturer's instructions in order to lyze the cells and provide the substrate for the firefly luciferase (*Photinus pyralis*) formed in the cells. After incubation at room temperature in the dark for 10 minutes, the firefly luciferase-mediated chemiluminescence is measured in a measuring instrument (measuring time/well 1 sec; Trilux from Wallac). Then 50 μl of the Dual-Glo™ Stop & Glo reagent (Dual-Glo™ Luciferase Assay System; Promega) is added to each well in order to stop the activity of the firefly luciferase and provide the substrate for the Renilla luciferase expressed by the reference plasmid pRL-CMV. After incubation at room temperature in the dark for a further 10 minutes, a chemiluminescence mediated by the Renilla luciferase is again measured for 1 sec/well in the measuring instrument.

Evaluation

The crude data from the luminometer are transferred into a Microsoft Excel file. The firefly/Renilla luciferase activity ratio is determined for each measurement derived from one well of the microtiter plate. The dose-effect plots and EC50 values of PPAR agonists are calculated from the ratios by the XL.Fit program as specified by the manufacturer (IDBS).

PPARgamma EC50 values in the range from 6nM to >10 μM were measured for the PPAR agonists described in this application.

The citation of any reference herein should not be construed as an admission that such reference is available as "Prior Art" to the instant application.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

The examples below serve to illustrate the invention, but without limiting it.

TABLE II

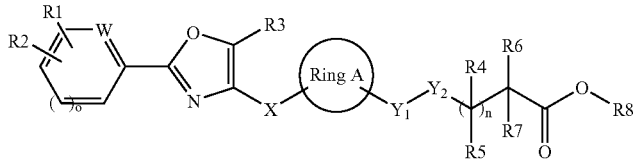

hereinbelow:
Ring A = cis-cyclohexane-1,3-diyl, W = CH if o = 1, R4 = R5 = R8 = H.

| Ex. | R1 | R2 | R3 | X | Y1 | Y2 | n | R6 | R7 | R9 | R10 |
|---|---|---|---|---|---|---|---|---|---|---|---|
| 1 | 4-F | H | Me | CH2O | O | CH2 | 1 | H | Et | — | — |
| 2 | 4-F | H | Me | CH2O | O | CH2 | 1 | H | n-Pr | — | — |
| 3 | 4-F | H | Me | CH2O | O | CH2 | 1 | H | H | — | — |
| 4 | 4-F | H | Me | CH2O | O | CH2 | 1 | H | Me | — | — |
| 5 | 3-Me | H | Me | CH2O | O | CH2 | 0 | | cyclopropyl | — | — |
| 6 | 3-Me | H | Me | CH2O | O | CH2 | 0 | H | CH2NR9R10 | Me | Bn |
| 7 | 3-Me | H | Me | CH2O | O | CH2 | 0 | H | CH2NR9R10 | Me | PhCH2CH2 |
| 8 | 3-Me | H | Me | CH2O | O | CH2 | 0 | H | MeOCH2 | — | — |
| 9 | 3-Me | H | Me | CH2O | O | CH2 | 0 | H | 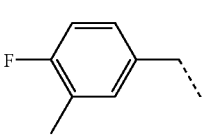 | — | — |
| 10 | 3-Me | H | Me | CH2O | O | CH2 | 0 | H | n-PrO | — | — |
| 11 | 3-Me | H | Me | CH2O | O | CH2 | 0 | H | 4-CF$_3$—(C6H4)—CH2O | — | — |
| 12 | 3-Me | H | Me | CH2O | O | CH2 | 0 | H | MeO | — | — |
| 13 | 3-Me | H | Me | CH2O | O | CH2 | 0 | H | 4-CF$_3$—(C6H4)—CH2O | — | — |
| 14 | 3-Me | H | Me | CH2O | O | CH2 | 0 | H | 3-CF$_3$—(C6H4)—CH2O | — | — |
| 15 | 3-Me | H | Me | CH2O | O | CH2 | 0 | H | 3-MeO—(C6H4)—CH2O | — | — |
| 16 | 3-Me | H | Me | CH2O | O | CH2 | 0 | H | 2-Me-4-Me-(C6H4)—CH2O | — | — |
| 17 | 3-Me | H | Me | CH2O | O | CH2 | 0 | H | 4-Me-(C6H4)—CH2O | — | — |
| 18 | 3-Me | H | Me | CH2O | O | CH2 | 0 | H | 4-$^t$Bu--(C6H4)—CH2O | — | — |
| 19 | 3-Me | H | Me | CH2O | O | CH2 | 0 | H | 2-CF$_3$—(C6H4)—CH2O | — | — |
| 20 | 3-Me | H | Me | CH2O | O | CH2 | 0 | H | 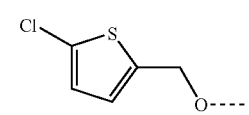 | — | — |
| 21 | 3-Me | H | Me | CH2O | O | CH2 | 0 | H | 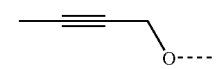 | — | — |
| 22 | 3-Me | H | Me | CH2O | O | CH2 | 0 | H | 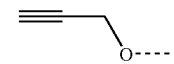 | — | — |
| 23 | 3-Me | H | Me | CH2O | O | CH2 | 0 | H |  | — | — |
| 24 | 3-Me | H | Me | CH2O | O | CH2 | 0 | H | 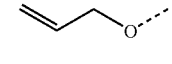 | — | — |
| 25 | 3-Me | H | Me | CH2O | O | CH2 | 0 | H | 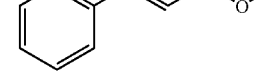 | — | — |
| 26 | 3-Me | H | Me | CH2O | O | CH2 | 0 | H | 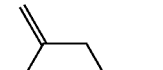 | — | — |
| 27 | 3-Me | H | Me | CH2O | O | CH2 | 0 | H | BnO | — | — |
| 28 | H | H | Me | CH2O | O | CH2 | 0 | H | MeO | — | — |
| 29 | 3-CF3 | H | Me | CH2O | O | CH2 | 0 | H | MeO | — | — |
| 30 | 3-OCF3 | H | Me | CH2O | O | CH2 | 0 | H | MeO | — | — |
| 31 | 4-CF3 | H | Me | CH2O | O | CH2 | 0 | H | MeO | — | — |
| 32 | 4-Me | H | Me | CH2O | O | CH2 | 0 | H | MeO | — | — |
| 33 | 2-Me | 6-Me | Me | CH2O | O | CH2 | 0 | H | MeO | — | — |

TABLE II-continued

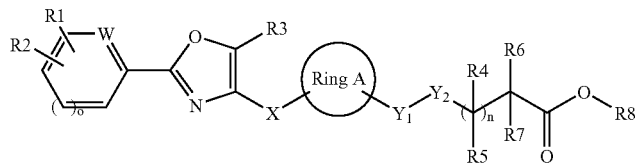

hereinbelow:
Ring A = cis-cyclohexane-1,3-diyl, W = CH if o = 1, R4 = R5 = R8 = H.

| Ex. | R1 | R2 | R3 | X | Y1 | Y2 | n | R6 | R7 | R9 | R10 |
|---|---|---|---|---|---|---|---|---|---|---|---|
| 34 | 2-CF3 | H | Me | CH2O | O | CH2 | 0 | H | MeO | — | — |
| 35 | 2-Naphthyl | | Me | CH2O | O | CH2 | 0 | H | MeO | — | — |
| 36 | 2-Me | 4-Me | Me | CH2O | O | CH2 | 0 | H | MeO | — | — |
| 37 | 4-Ph | H | Me | CH2O | O | CH2 | 0 | H | MeO | — | — |
| 38 | 3-OMe | H | Et | CH2O | O | CH2 | 0 | H | MeO | — | — |
| 39 | 4-Me | H | Et | CH2O | O | CH2 | 0 | H | MeO | — | — |
| 40 | 2-CF3 | H | Et | CH2O | O | CH2 | 0 | H | MeO | — | — |
| 41 | 2-Me | 6-Me | Et | CH2O | O | CH2 | 0 | H | MeO | — | — |
| 42 | H | H | Me | CH2O | O | CH2 | 0 | H | n-PrO | — | — |
| 43 | 3-Me | H | Me | CH2O | O | CH2 | 0 | H | n-PrO | — | — |
| 44 | 3-OCF3 | H | Me | CH2O | O | CH2 | 0 | H | n-PrO | — | — |
| 45 | 3-OMe | H | Me | CH2O | O | CH2 | 0 | H | n-PrO | — | — |
| 46 | 4-CF3 | H | Me | CH2O | O | CH2 | 0 | H | n-PrO | — | — |
| 47 | 4-Me | H | Me | CH2O | O | CH2 | 0 | H | n-PrO | — | — |
| 48 | 4-CF3 | H | Me | CH2O | O | CH2 | 0 | H | n-PrO | — | — |
| 49 | 4-i-Pr | H | Me | CH2O | O | CH2 | 0 | H | n-PrO | — | — |
| 50 | 2-CF3 | H | Me | CH2O | O | CH2 | 0 | H | n-PrO | — | — |
| 51 | 2-Naphthyl | | Me | CH2O | O | CH2 | 0 | H | n-PrO | — | — |
| 52 | 3-CF3 | H | Me | CH2O | O | CH2 | 0 | H | n-PrO | — | — |
| 53 | 3-OMe | H | Et | CH2O | O | CH2 | 0 | H | n-PrO | — | — |
| 54 | 4-Me | H | Et | CH2O | O | CH2 | 0 | H | n-PrO | — | — |
| 55 | 2-CF3 | H | Et | CH2O | O | CH2 | 0 | H | n-PrO | — | — |
| 56 | 2-Me | 6-Me | Et | CH2O | O | CH2 | 0 | H | n-PrO | — | — |
| 57 | 3-CF3 | H | Me | CH2O | O | CH2 | 0 | H | EtO | — | — |
| 58 | 3-OCF3 | H | Me | CH2O | O | CH2 | 0 | H | EtO | — | — |
| 59 | 4-CF3 | H | Me | CH2O | O | CH2 | 0 | H | EtO | — | — |
| 60 | 4-OCF3 | H | Me | CH2O | O | CH2 | 0 | H | EtO | — | — |
| 61 | 4-i-Pr | H | Me | CH2O | O | CH2 | 0 | H | EtO | — | — |
| 62 | 2-CF3 | H | Me | CH2O | O | CH2 | 0 | H | EtO | — | — |
| 63 | 2-Me | 4-Me | Me | CH2O | O | CH2 | 0 | H | EtO | — | — |
| 64 | 4-Ph | H | Me | CH2O | O | CH2 | 0 | H | EtO | — | — |
| 65 | 4-Me | H | Et | CH2O | O | CH2 | 0 | H | EtO | — | — |
| 66 | 4-i-Pr | H | Et | CH2O | O | CH2 | 0 | H | EtO | — | — |
| 67 | 2-CF3 | H | Et | CH2O | O | CH2 | 0 | H | EtO | — | — |
| 68 | 2-Me | 6-Me | Et | CH2O | O | CH2 | 0 | H | EtO | — | — |
| 69 | 4-i-Pr | H | Et | CH2O | O | CH2 | 0 | H | n-PrO | — | — |
| 70 | H | H | Me | CH2O | O | CH2 | 0 | H | EtO | — | — |
| 71 | 3-Me | H | Me | CH2O | O | CH2 | 0 | H | EtO | — | — |
| 72 | 3-OMe | H | Me | CH2O | O | CH2 | 0 | H | EtO | — | — |
| 73 | 4-Me | H | Me | CH2O | O | CH2 | 0 | H | EtO | — | — |
| 74 | 2-Naphthyl | | Me | CH2O | O | CH2 | 0 | H | EtO | — | — |
| 75 | 3-OMe | H | Et | CH2O | O | CH2 | 0 | H | EtO | — | — |
| 76 | 3-Me | H | Me | CH2O | O | CH2 | 0 | H | 4-CF3—(C6H4)—CH2O | — | — |
| 77 | 3-CF3 | H | Me | CH2O | O | CH2 | 0 | H | 4-CF3—(C6H4)—CH2O | — | — |
| 78 | 3-OCF3 | H | Me | CH2O | O | CH2 | 0 | H | 4-CF3—(C6H4)—CH2O | — | — |
| 79 | 4-i-Pr | H | Me | CH2O | O | CH2 | 0 | H | 4-CF3—(C6H4)—CH2O | — | — |
| 80 | 2-Naphthyl | | Me | CH2O | O | CH2 | 0 | H | 4-CF3—(C6H4)—CH2O | — | — |
| 81 | 4-Me | H | Me | CH2O | O | CH2 | 0 | H | 4-CF3—(C6H4)—CH2O | — | — |
| 82 | 4-OCF3 | H | Me | CH2O | O | CH2 | 0 | H | 4-CF3—(C6H4)—CH2O | — | — |
| 83 | 4-CF3 | H | Me | CH2O | O | CH2 | 0 | H | 4-CF3—(C6H4)—CH2O | — | — |
| 84 | 3-OMe | H | Me | CH2O | O | CH2 | 0 | H | 4-CF3—(C6H4)—CH2O | — | — |
| 85 | 3-CF3 | H | Me | CH2O | O | CH2 | 0 | H | i-BuO | — | — |
| 86 | 3-OMe | H | Me | CH2O | O | CH2 | 0 | H | i-BuO | — | — |
| 87 | 4-Me | H | Me | CH2O | O | CH2 | 0 | H | i-BuO | — | — |
| 88 | 4-i-Pr | H | Me | CH2O | O | CH2 | 0 | H | i-BuO | — | — |
| 89 | 3-Me | H | Me | CH2OCH2 | O | CH2 | 0 | H | 4-CF3—(C6H4)—CH2O | — | — |
| 90 | 3-Me | H | Me | CH2OCH2 | O | CH2 | 0 | H | 4-CF3—(C6H4)—CH2O | — | — |
| 91 | 3-Me | H | Me | CH2O | O | CH2 | 1 | H | m-CF3—(C6H4)—CH2 | — | — |

Broken line indicates the point of attachment.

The compounds of the formula I according to the invention can be obtained according to the reaction schemes below:

Process A:

This process is used for synthesizing the building block A-A in which R1, R2, W and R3 are as defined above.

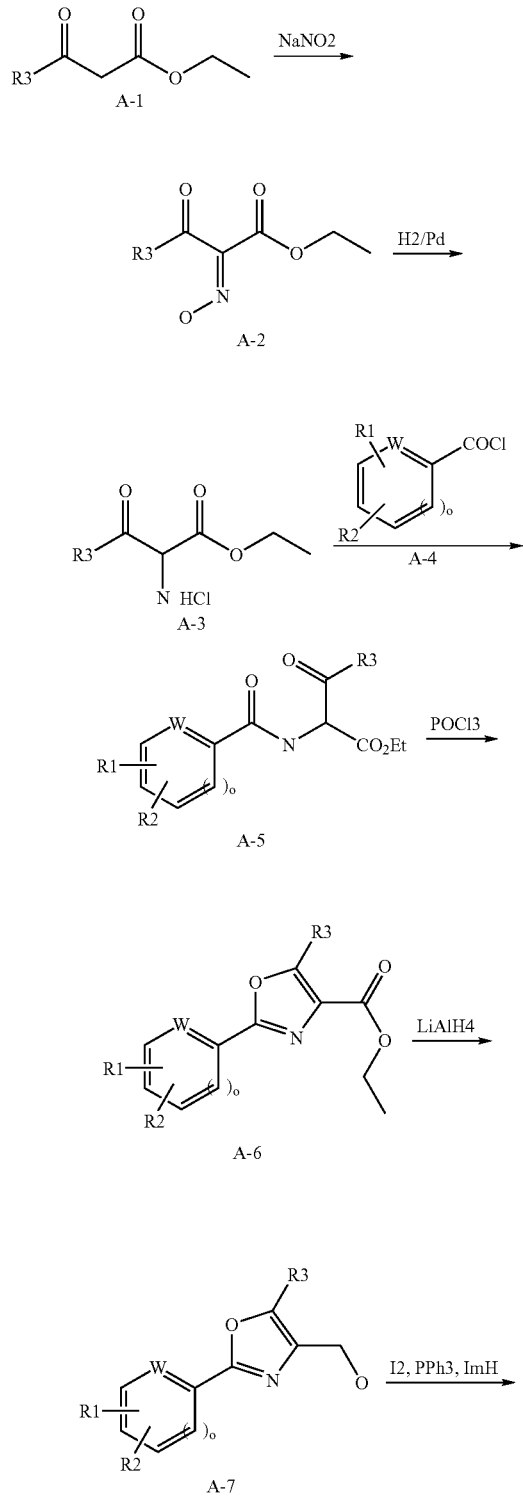

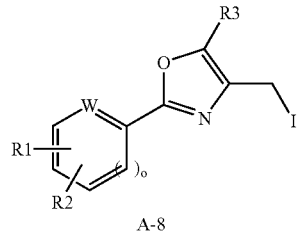

Using sodium nitrite and hydrochloric acid, ester A-1, in which R3 is as defined above is converted into oxime A-2 which is reduced to amine A-3 by hydrogenation with hydrogen over palladium/carbon.

Using acid chlorides of the formula A4 in which R1, W and R2 are as defined above and base (for example triethylamine), compound A-3 is converted into compound A-5.

By heating in phosphoryl chloride, compound A-5 is converted into compound A-6.

Using lithium aluminum hydride in diethyl ether, ester A-6 is reduced to alcohol A-7. This is converted into iodide A-8 using iodine, imidazole (ImH) and triphenylphosphine.

Process B:

This process is used for synthesizing the building block A-8 in which R1, R2, W and R3 are as defined above.

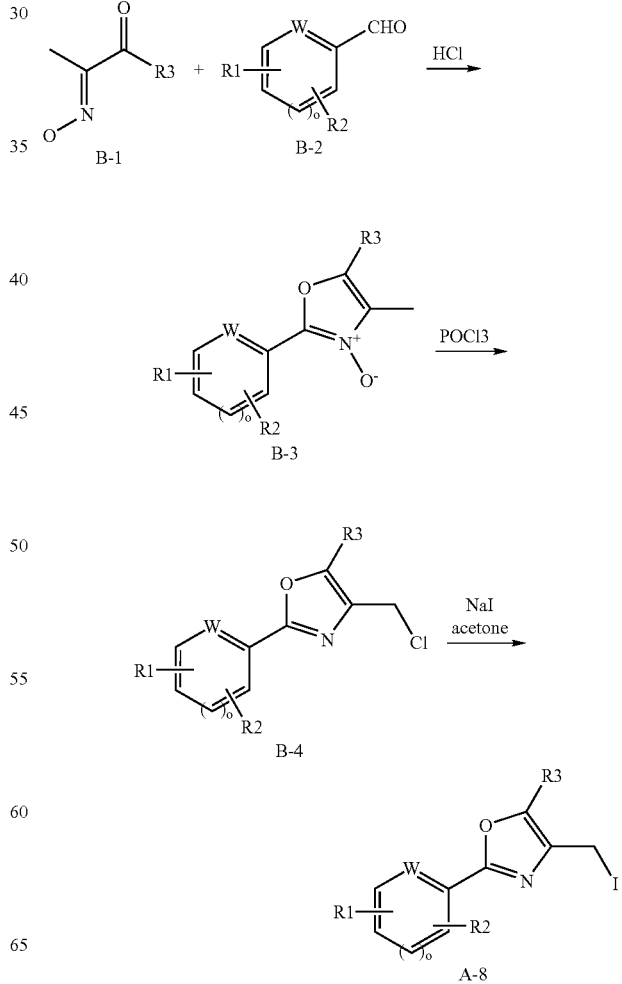

In ethanol and using hydrogen chloride, compound B-1 is reacted with aldehyde B-2 in which R1, R2, W and R3 are as defined above, to give compound B-3. Compound B-3 is heated to the boil in phosphoryl chloride, giving compound B-4. This is heated to the boil with sodium iodide in acetone. This gives compound A-8.
Process C:
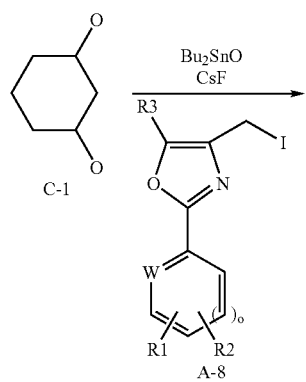
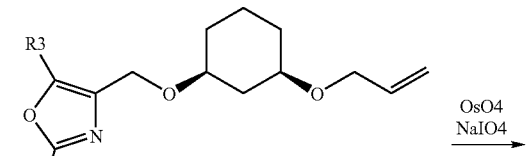
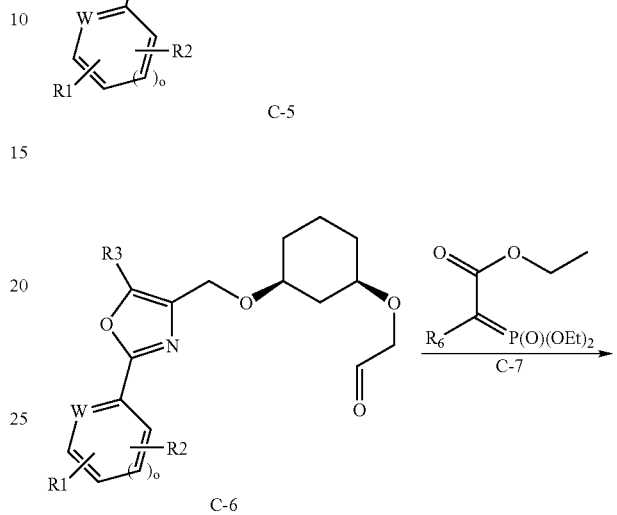
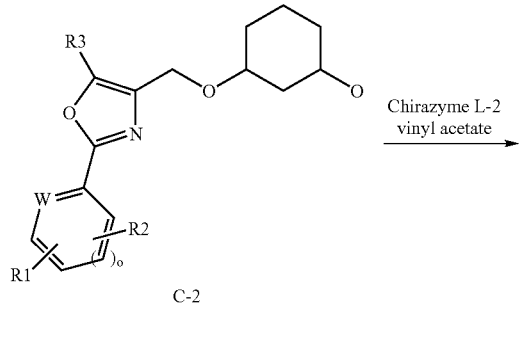
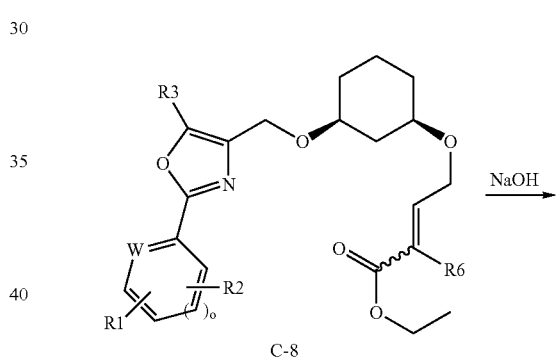
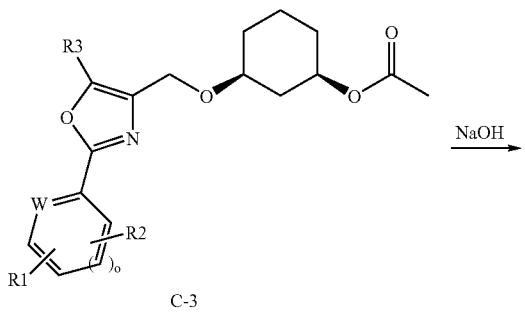
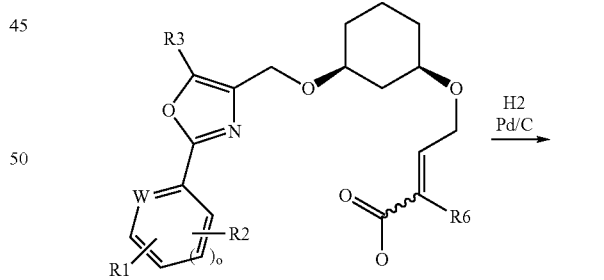
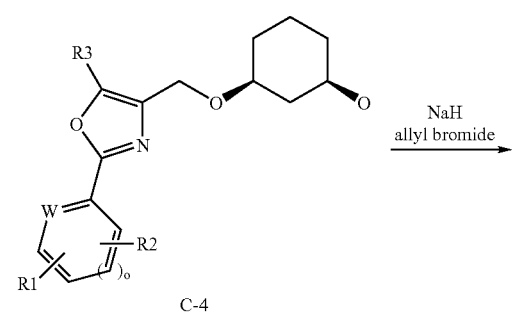

Compound C-1 is boiled with dibutyltin oxide in toluene under reflux on a water separator. Following addition of dimethylformamide, cesium fluoride and compound A-8 (see process A), the suspension is stirred at room temperature. This gives compound C-2. This is converted with Chirazyme L-2 in vinyl acetate into the enantiomerically enriched acetate C-3. Acetate C-3 is converted with sodium hydroxide in methanol into alcohol C4.

Compound C-4 is reacted with sodium hydride and allyl bromide in dimethylformamide at room temperature, to give compound C-5.

Compound C-5 is reacted with osmium tetroxide and sodium periodate in diethyl ether, to give compound C-6.

This is reacted in a Horner-Emmons-Wadsworth reaction with sodium hydride and compound C-7 to give compound C-8.

Compound C-8 is hydrolyzed to the free acid by stirring at room temperature with sodium hydroxide in methanol for a number of hours. The resulting compound C-9 is hydrogenated with hydrogen over palladium/carbon to compound C-10.

According to this process, it is possible to synthesize examples 1 to 4.

Process D:

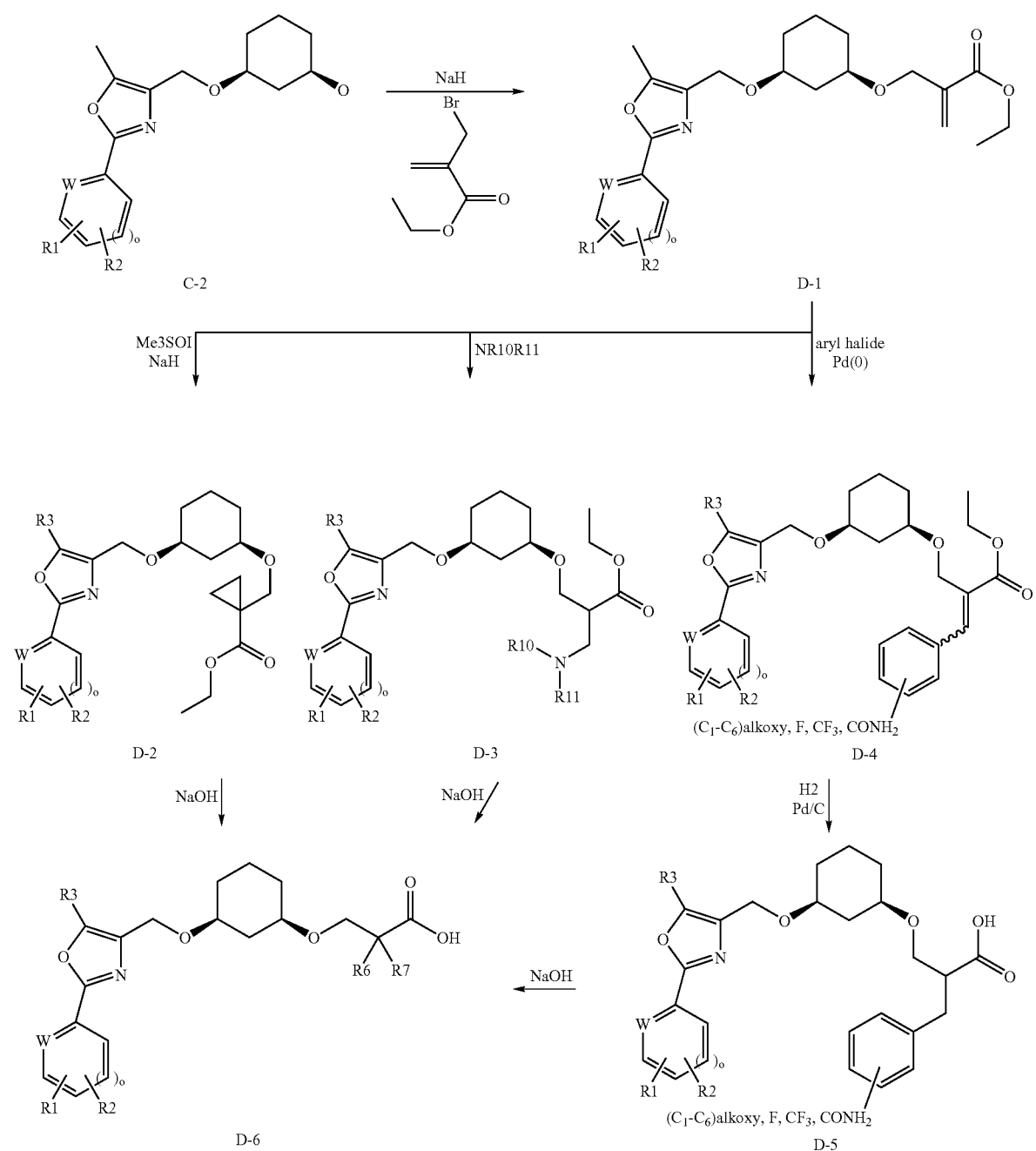

Compound C-2 is reacted with sodium hydride and ethyl 2-bromomethylacrylate in dimethylformamide at 0C, to give compound D-1.

Compound D-1 is then reacted either with trimethylsulfonium iodide and sodium hydride in dimethyl sulfoxide, to give compound D-2, or with a secondary amine NR10R11, where R10 and R11 are as defined above, to give compound D-3, or with an aryl halide and a palladium(O) catalyst in a Heck reaction, to give compound D-4. Compound D-4 is then hydrogenated with hydrogen over palladium on carbon, to give compound D-5.

Compounds D-2, D-3 and D-5 are converted with sodium hydroxide into compounds of the general formula D-6, where R6 and R7 are as defined above. According to this process, it is possible to synthesize examples 5 to 9.

Process E:

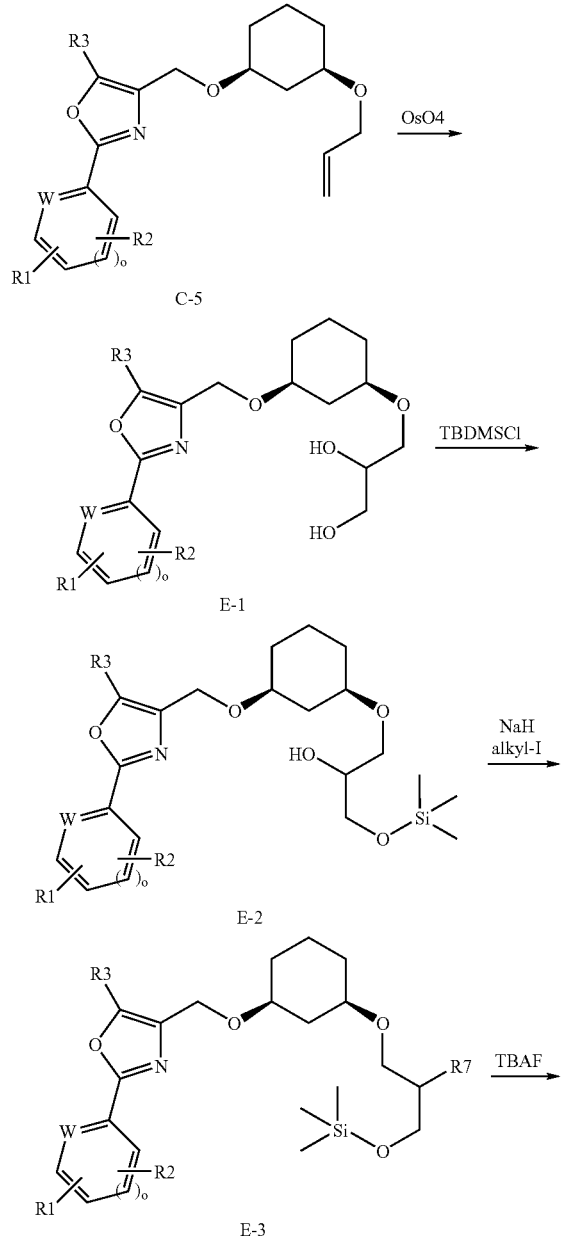

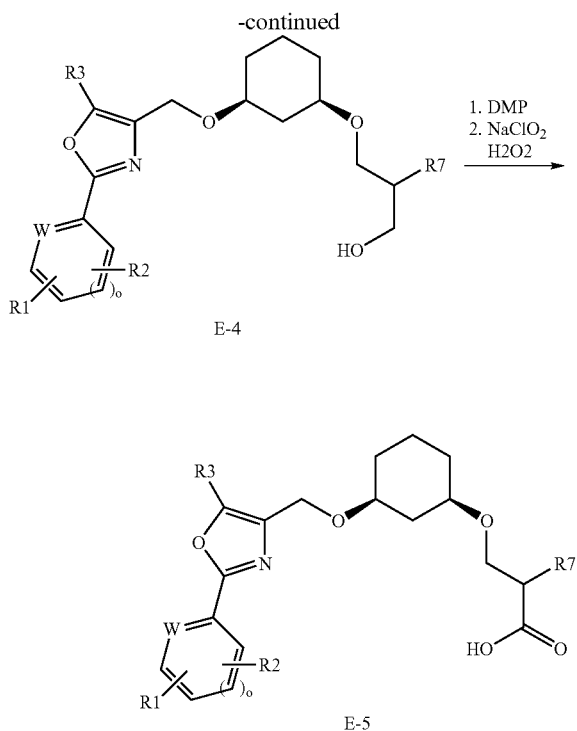

Compound C-5 is dihydroxylated with osmium tetroxide, 1,5-diazabicyclo[2.2.2]-octane (DABCO) and N-methylmorpholine N-oxide, to give compound E-1. The primary hydroxyl group is then protected as trialkylsilyl ether E-2 by stirring compound E-1 with a trialkylchlorosilane (for example tert-butyldimethylsilyl chloride) and imidazole as base in dimethylformamide at room temperature. Compound E-2 is then reacted with a strong base (for example sodium hydride or potassium tert-butoxide) and an alkyl halide to give compound E-3 in which R7 is as defined above. The silyl protective group is removed using tetrabutylammonium fluoride in tetrahydrofuran, to give compound E-4.

Compound E-4 is stirred with Dess-Martin periodinane (DMP) in dichloromethane at room temperature for a number of hours, worked up and then reacted with sodium chlorite and hydrogen peroxide in acetonitrile, to give compound E-5. Alternatively, E-5 can be synthesized by direct oxidation of E-4 using a chromium(VI) compound (for example CrO3 in sulfuric acid).

According to this process, it is possible to synthesize examples 10 to 27.

Process F:

This process is used for an alternative preparation of intermediates E-3 (see process E)

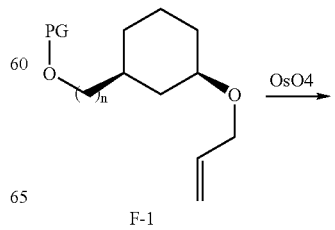

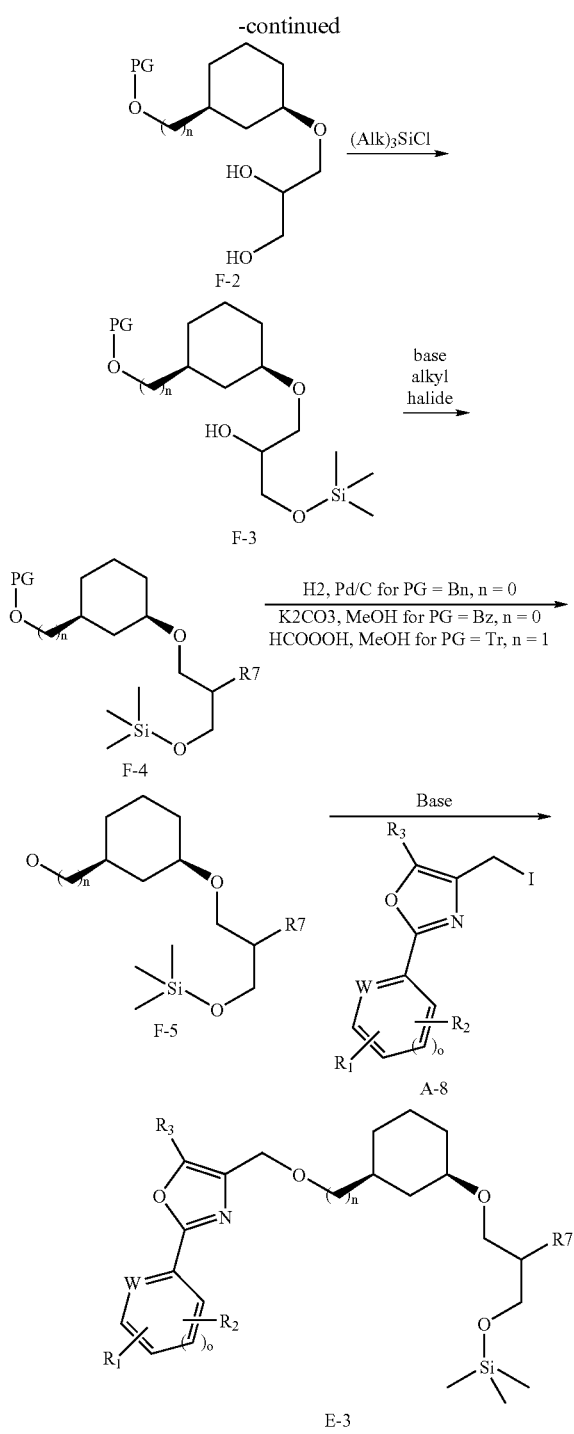

Compound F-3 is then reacted with a strong base (for example sodium hydride or potassium tert-butoxide) and an alkyl halide, to give compound F-4, where R7 is as defined above. The benzyl protective group is removed hydrogenolytically using hydrogen over Pd (10% on carbon), the benzoyl protective group is removed using potassium carbonate in methanol and the trityl group is removed using formic acid in methanol, to give compound F-5.

Using alkyl iodide A-8 in the presence of a strong base (for example sodium hydride or potassium tert-butoxide) in an inert solvent (for example MTBE, chlorobenzene), compound E-5 is converted into compound E-3 in which R1, R2, R3, R7 and W are as defined above.

The subsequent conversions of E-3 into E-5 are then carried out as described under process E.

According to this process, it is possible to synthesize examples 28 to 90.

Process G:

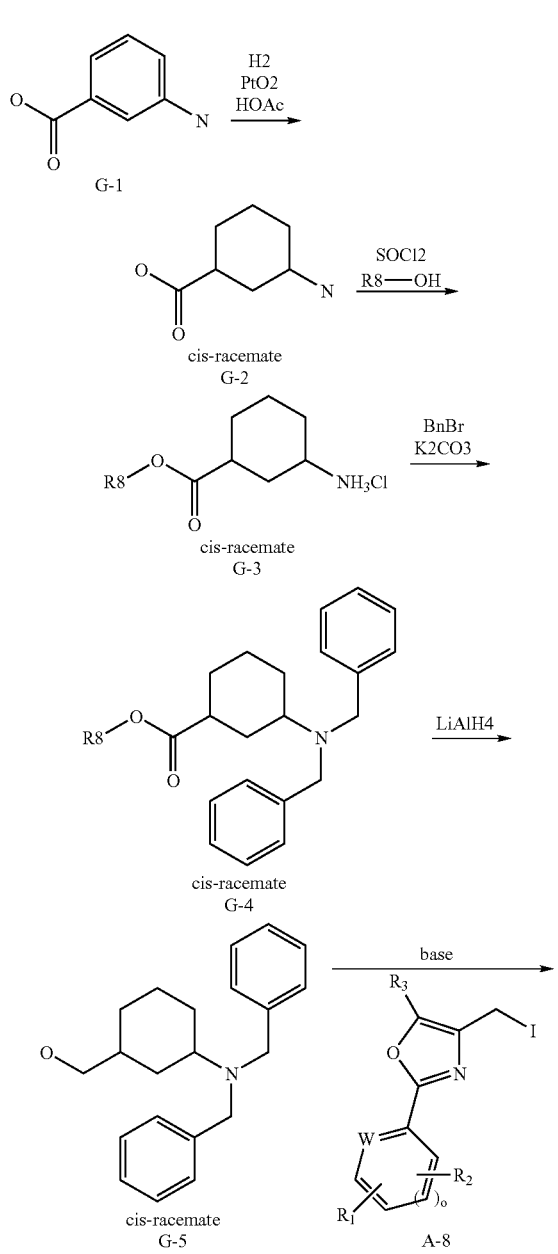

The racemic or enantiomerically pure compound F-1 in which PG has the meaning indicated in the scheme is dihydroxylated with osmium tetroxide, 1,5-diazabicyclo-[2.2.2]octane (DABCO) and N-methylmorpholine N-oxide, to give compound F-2.

The primary hydroxyl group is then protected as trialkylsilyl ether F-3 by stirring compound F-2 with a trialkylchlorosilane (for example tert-butyldimethylsilyl chloride) and imidazole as base in dimethylformamide at room temperature.

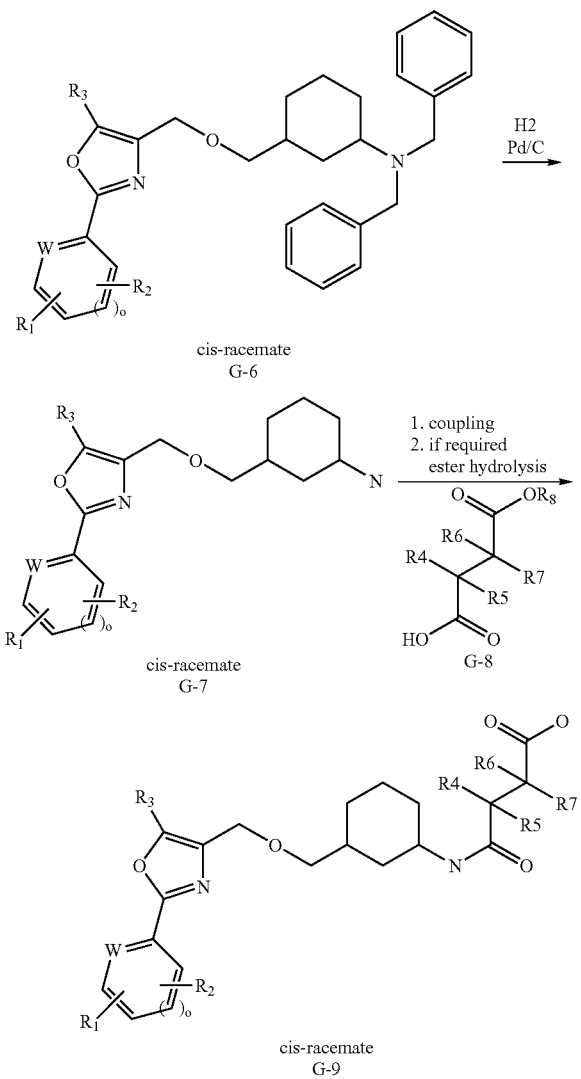

cis-racemate
G-6 cis-racemate
G-7

1. coupling
2. if required ester hydrolysis cis-racemate
G-9

Compound G-1 (3-aminobenzoic acid) is hydrogenated in acetic acid using hydrogen over platinum dioxide under elevated pressure, to give compound G-2.

Using thionyl chloride in an alcohol R8OH in which R8 is as defined above (except for R8=H), this compound is converted to an ester, to give compound G-3. Compound G-3 is then reacted with benzyl bromide and potassium carbonate, to give dibenzylamine G-4. Reduction of G4 with LiAlH4 gives alcohol G-5.

Using an alkyl iodide A-8, compound G-5 is converted into compound G-6 in which R1, R2, W and R3 are as defined above. Using hydrogen over palladium, compound G-6 is hydrogenated to compound G-7 in which R1, R2, W and R3 are as defined above.

Compound G-7 is coupled with carboxylic acid derivatives G-8 in which R4, R5, R6 and R7 are as defined above. If dicarboxylic acid monoesters G-8 are used, the coupling is followed by an ester hydrolysis (using, for example, LiOH in THF/methanol/water for R8=methyl or ethyl). This gives compound G-9 in which R1, R2, W, R3, R4, R5, R6 and R 7 are as defined above.

According to this process, it is possible to synthesize examples 28 to 90.

The abbreviations used denote:

| | |
|---|---|
| Ac | acetyl |
| Bn | benzyl |
| $^i$Bu | isobutyl |
| $^t$Bu | tert-butyl |
| BuLi | n-butyllithium |
| Bz | benzoyl |
| Cy | cyclohexyl |
| TLC | thin-layer chromatography |
| DCI | direct chemical ionization (in MS) |
| DCM | dichloromethane |
| DMAP | 4-N,N-dimethylaminopyridine |
| DMF | N,N-dimethylformamide |
| DMSO | dimethyl sulfoxide |
| EE | ethyl acetate |
| EDC | N'-(3-dimethylaminopropyl)-N-ethylcarbodiimide × HCl |
| EI | electron impact ionization (in MS) |
| eq | equivalent |
| ESI | electron spray ionization (in MS) |
| Et | ethyl |
| sat. | saturated |
| h | hour |
| HATU | O-(7-azabenzotriazol-1-yl)-N,N,N',N'-tetramethyluronium hexafluorophosphate |
| HOBt | 1-hydroxy-1H-benzotriazole × H$_2$O |
| HPLC | high pressure, high performance liquid chromatography |
| LC-MS | liquid chromatography-coupled mass spectroscopy |
| Me | methyl |
| MS | mass spectroscopy |
| MsCl | methanesulfonyl chloride |
| NMR | nuclear magnetic resonance spectroscopy |
| Pd/C | palladium on carbon |
| $^i$Pr | isopropyl |
| $^n$Pr | n-propyl |
| R$_f$ | retention time (in TLC) |
| RT | room temperature |
| TBAF | tetrabutylammonium fluoride |
| TBAI | tetrabutylammonium iodide |
| TBDPSCl | tert-butyldiphenylsilyl chloride |
| TBDMSCl | tert-butyldimethylsilyl chloride |
| THF | tetrahydrofuran |
| Tr | trityl |

It is possible to prepare other compounds by the processes mentioned above.

Building block synthesis according to process A:

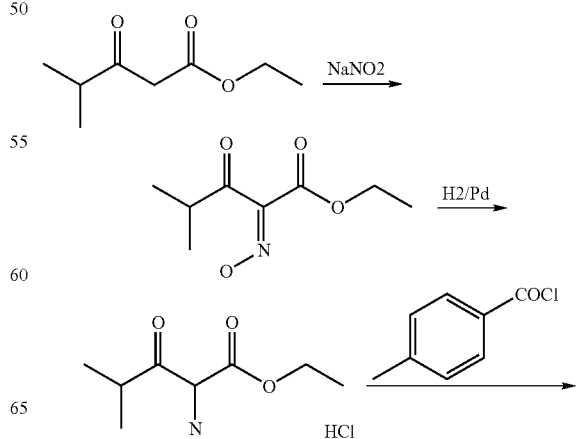

-continued

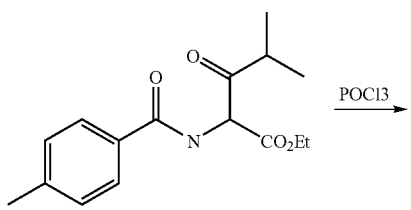

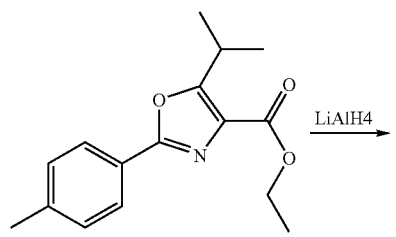

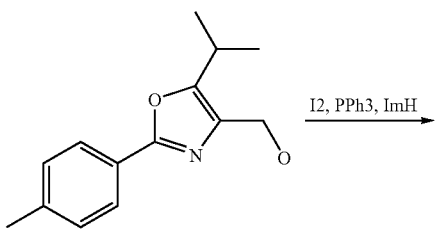

Ethyl 2-hydroxyimino-4-methyl-3-oxopentanoate

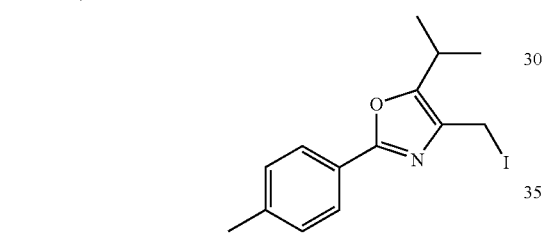

42.4 g of ethyl 4-methyl-3-oxopentanoate are dissolved in 100 ml of glacial acetic acid, and 21 g of sodium nitrite, dissolved in 100 ml of water, are added at 5° C. Over a period of one hour, the mixture is allowed to warm to room temperature, 100 ml of water are added and the mixture is stirred at room temperature for another hour. The mixture is extracted three times with in each case 150 ml of methyl tert-butyl ether, 200 ml of water are added to the combined organic phases and the mixture is neutralized by addition of solid NaHCO3. The organic phase is removed, washed with saturated NaCl solution and dried over MgSO4, and the solvent is removed under reduced pressure. This gives 46 g of ethyl 2-hydroxy-imino-4-methyl-3-oxopentanoate as an oil. C8H13NO4 (187.20), MS (ESI) =188 (M+H+).

Ethyl 2-amino-4-methyl-3-oxopentanoate hydrochloride

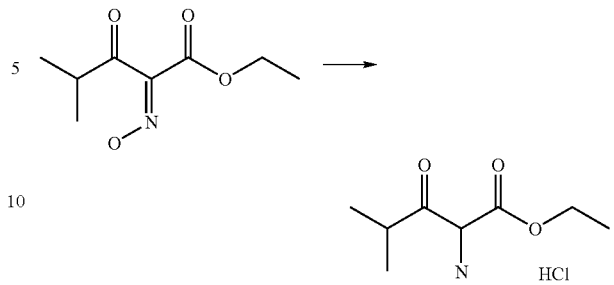

10 g of HCl are introduced into 200 ml of ethanol. 46 g of ethyl 2-hydroxyimino4-methyl-3-oxopentanoate are dissolved in this mixture, 5 g of Pd (10% on carbon) are added and the mixture is stirred under an atmosphere of hydrogen (5 bar) for 8 hours. The reaction mixture is filtered through Celite and the solvent is removed under reduced pressure. This gives 45 g of ethyl 2-amino-4-methyl-3-oxopentanoate hydrochloride as a white solid. C8H15NO3*HCl (209.5), MS(ESI)=188 (M+H+).

Ethyl 4-methyl-2-(4-methylbenzoylamino)-3-oxopentanoate

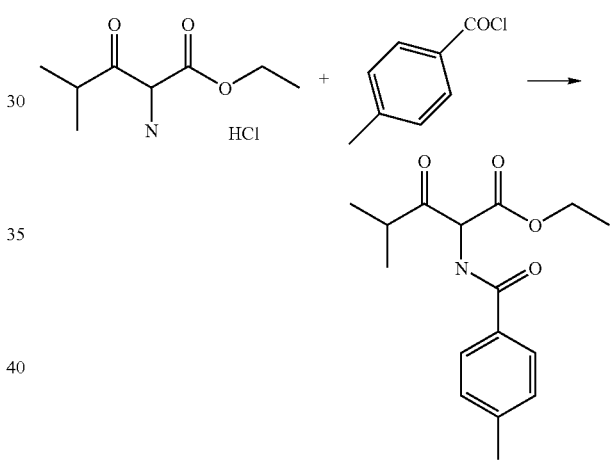

10 g of ethyl 2-amino-4-methyl-3-oxopentanoate hydrochloride and 7.4 g of 4-methylbenzoyl chloride are dissolved in 250 ml of dichloromethane, and 13.3 ml of triethylamine are slowly added dropwise at 0° C. The mixture is stirred at room temperature for one hour and then washed with water, the organic phase is separated off and dried over MgSO4, and the solvent is then removed under reduced pressure. This gives 13 g of ethyl 4-methyl-2-(4-methylbenzoylamino)-3-oxopentanoate as an oil. C16H21NO4 (291.35), MS(ESI)=292 (M+H+).

Ethyl 5-isopropyl-2-p-tolyloxazole4-carboxylate

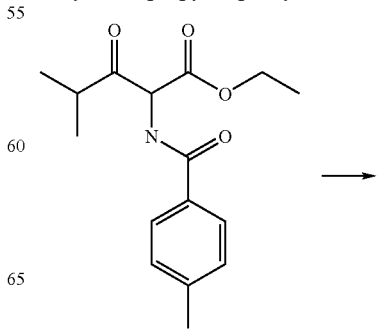

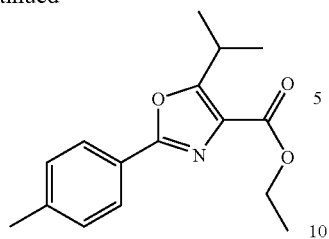

13 g of ethyl 4-methyl-2-(4-methylbenzoylamino)-3-oxopentanoate in 80 ml of phosphorus oxychloride are heated to the boil under reflux for 2 h. The phosphorus oxychloride is removed under reduced pressure and the resulting residue is dissolved in 200 ml of dichloromethane, washed three times with saturated NaHCO$_3$ solution and dried over MgSO4, and the solvent is then removed under reduced pressure. This gives 11 g of ethyl 5-isopropyl-2-p-tolyloxazole-4-carboxylate as a brownish solid. C16H19NO3 (273.33), MS(ESI) =292 (M+H$^+$), Rf(n-heptane:ethyl acetate)=2:1)=0.43.

(5-Isopropyl-2-p-tolyloxazol-4-yl)methanol

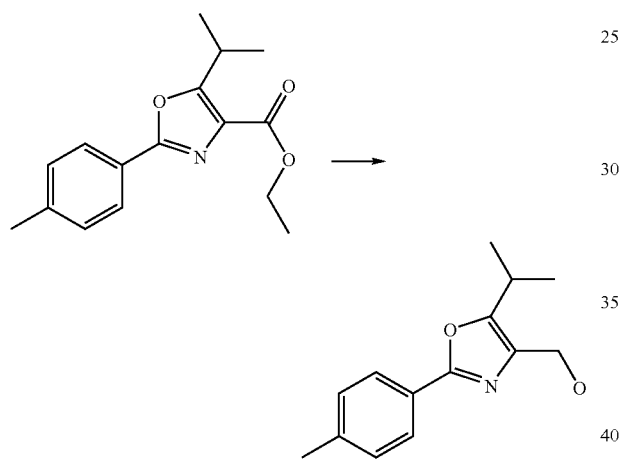

11 g of ethyl 5-isopropyl-2-p-tolyloxazole-4-carboxylate are dissolved in 100 ml of tetrahydrofuran, and 40 ml of a 1 molar solution of lithium aluminum hydride in tetrahydrofuran are added at 0C. After 30 min, 50 ml of 1 N HCl are added to the reaction mixture, and the mixture is extracted five times with ethyl acetate. The combined organic phases are dried over MgSO4, and the solvent is then removed under reduced pressure. The residue is purified on silica gel using the mobile phase n-heptane:ethyl acetate=6:1=>1:1. This gives 4.3 g of (5-isopropyl-2-p-tolyloxazol4-yl)methanol as a light-yellow solid.

C14H17NO2 (231.30), MS(ESI)=232 (M+H$^+$), Rf(n-heptane:ethyl acetate)=1:1)=0.17

4-Iodomethyl-5-isopropyl-2-p-tolyloxazole

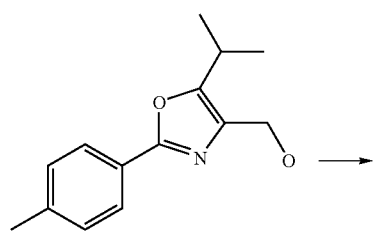

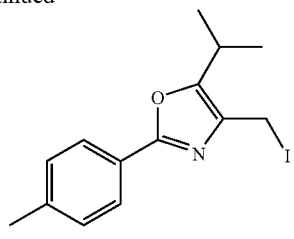

500 mg of (5-isopropyl-2-p-tolyloxazol-4-yl)methanol, together with 690 mg of triphenylphosphine and 600 mg of imidazole, are dissolved in 20 ml of toluene. 715 mg of iodine are added, and the mixture is stirred at room temperature for 1 hour. 10 ml of saturated sodium carbonate solution and 500 mg of iodine are then added. After 10 minutes, the organic phase is separated off, washed twice with saturated Na2S2O3 solution and dried over MgSO4, and the solvents are then removed under reduced pressure. The residue is purified on silica gel using the mobile phase n-heptane:ethyl acetate=10:1. This gives 400 mg of 4-iodomethyl-5-isopropyl-2-p-tolyloxazole as a white solid. C14H16INO (341.19), MS(ESI): 342 (M+H$^+$), Rf(n-heptane:ethyl acetate=1:1)=0.75.

Analogously to the building block synthesis according to process A, ethyl 2-amino-4-methyl-3-oxopentanoate hydrochloride and 3-methoxybenzoyl chloride gave 4-iodomethyl-2-(3-methoxyphenyl)-5-isopropyloxazole.

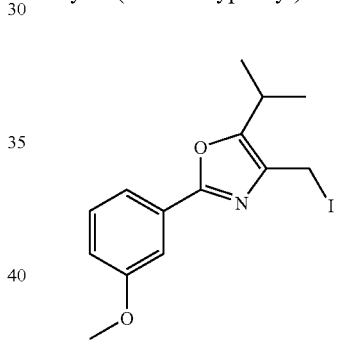

C14H16INO2 (357.19), MS(ESI): 358 (M+H$^+$), Rf(n-heptane:ethyl acetate=1:1)=0.60.

Analogously to the building block synthesis of 4-iodomethyl-5-isopropyl-2-p-tolyl-oxazole, ethyl 4,4,4-trifluoro-3-oxobutyrate and 3-methoxybenzoyl chloride gave 4-iodomethyl-2-(3-methoxyphenyl)-5-trifluoromethyloxazole.

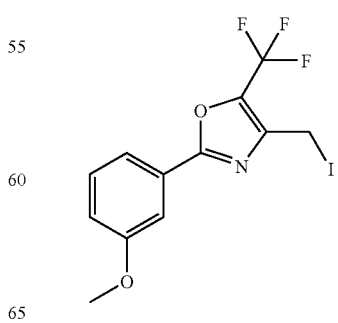

C12H9F31NO2 (383.11), MS(ESI): 384 (M+H$^+$).

Analogously to the building block synthesis of 4-iodomethyl-5-isopropyl-2-p-tolyl-oxazole, ethyl 4,4,4-trifluoro-3-oxobutyrate and 3-trifluoromethylbenzoyl chloride gave 4-iodomethyl-2-(3-trifluoromethylphenyl)-5-trifluoromethyloxazole.

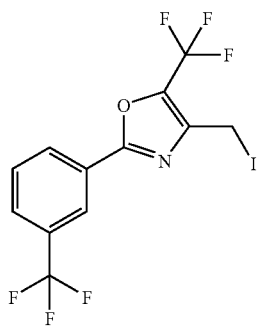

C12H6F6INO (421.08), MS(ESI): 422 (M+H⁺).

Analogously to the building block synthesis of 4-iodomethyl-5-isopropyl-2-p-tolyl-oxazole, ethyl 4,4,4-trifluoro-3-oxobutyrate and 4-methylbenzoyl chloride gave 4-iodomethyl-5-trifluoromethyl-2-p-tolyloxazole.

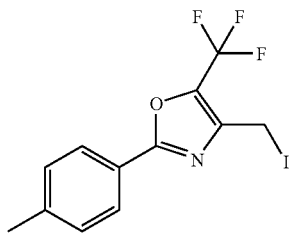

C12H9F3INO (367.11), MS(ESI): 368 (M+H⁺).

Building block synthesis according to process B:

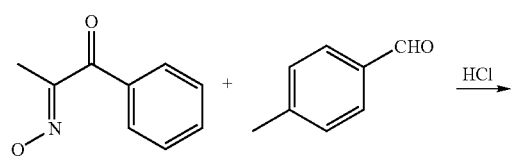

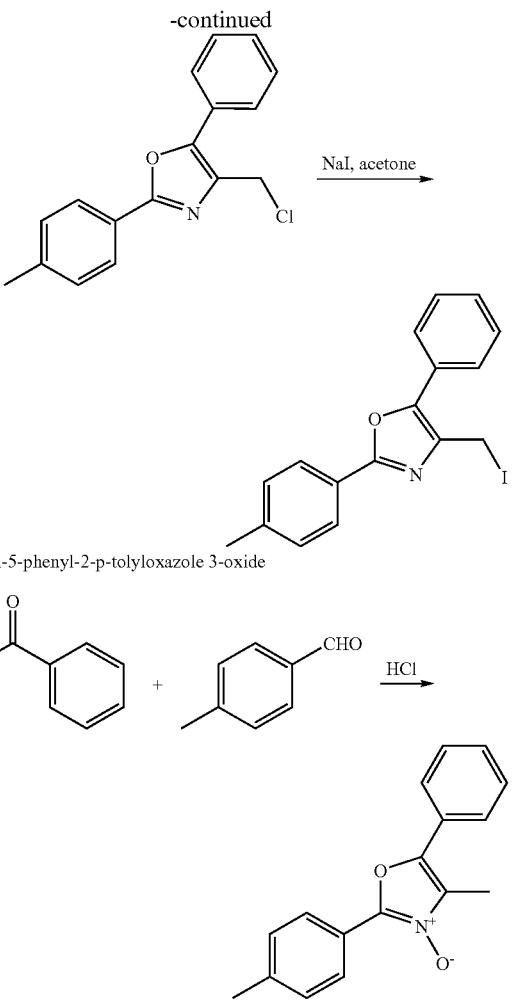

4-Methyl-5-phenyl-2-p-tolyloxazole 3-oxide 12.5 g of 1-phenyl-1,2-propanedione-2-oxime and 10 ml of p-tolualdehyde are added to 50 ml of glacial acetic acid, and HCl gas is introduced for 30 minutes, with ice-cooling. The product is precipitated as the hydrochloride by addition of methyl tert-butyl ether and filtered off with suction, and the precipitate is washed with methyl tert-butyl ether. The precipitate is suspended in water and the pH is made alkaline using ammonia. The mixture is extracted three times with in each case 200 ml of dichloromethane, the combined organic phases are dried over MgSO4 and the solvent is then removed under reduced pressure. This gives 6.4 g of 4-methyl-5-phenyl-2-p-tolyloxazole 3-oxide as a white solid. C17H15NO2 (265.31), MS(ESI)=266 (M+H⁺).

4-Chloromethyl-5-phenyl-2-p-tolyloxazole

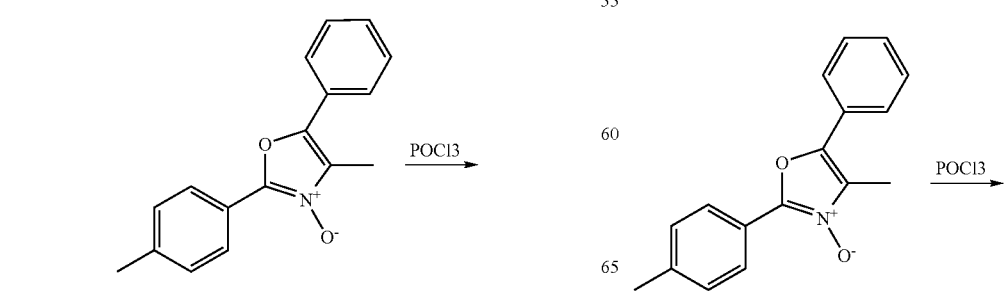

-continued

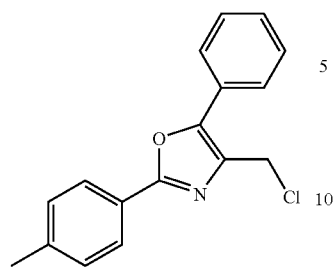

6.4 g of 4-methyl-5-phenyl-2-p-tolyloxazole 3-oxide are dissolved in 50 ml of chloroform, 2.4 ml of phosphorus oxychloride are added and the mixture is, under reflux, heated at the boil for 30 minutes. The reaction mixture is cooled to 0° C., the pH is made slightly alkaline using ammonia and the mixture is extracted three times with in each case 100 ml of ethyl acetate. The combined organic phases are washed with water and dried over MgSO4, and the solvent then removed under reduced pressure. This gives 5.4 g of 4-chloromethyl-5-phenyl-2-p-tolyloxazole as a yellow solid. C17H14ClNO (283.76), MS(ESI)=284 (M+H$^+$), Rf(n-heptane:ethyl acetate)=7:1)=0.41.

4-Iodomethyl-5-phenyl-2-p-tolyloxazole

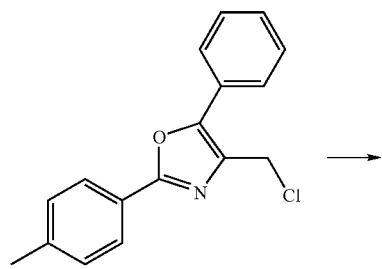

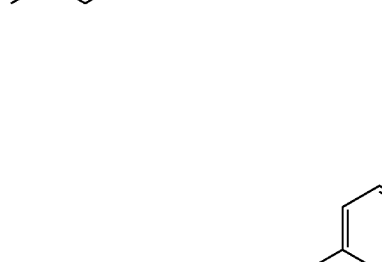

Together with 3 g of sodium iodide, 1.8 g of 4-chloromethyl-5-phenyl-2-p-tolyloxazole are, in 150 ml of acetone, heated at the boil under reflux for 2 hours. After cooling of the reaction mixture, 300 ml of methyl tert-butyl ether are added, the mixture is washed three times with saturated Na2S2O3 solution and dried over MgSO4, and the solvents are then removed under reduced pressure. This gives 2.7 g of 4-iodomethyl-5-phenyl-2-p-tolyloxazole as a light-yellow solid.

C17H14INO (375.21), MS(ESI): 376 (M+H$^+$).

Analogously to the building block synthesis of 4-iodomethyl-5-phenyl-2-p-tolyl-oxazole, 1-phenyl-1,2-propanedione-2-oxime and m-anisaldehyde gave 4-iodomethyl-2-(3-methoxyphenyl)-5-phenyloxazole.

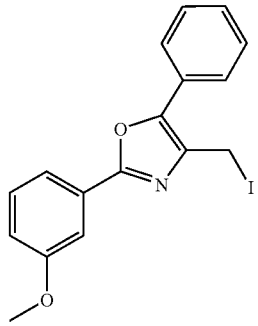

C17H14INO2 (391.21), MS(ESI): 392 (M+H$^+$).

Analogously to the building block synthesis of 4-iodomethyl-5-phenyl-2-p-tolyl-oxazole, 1-ethyl-1,2-propanedione-2-oxime and m-anisaldehyde gave 4-iodo-methyl-5-ethyl-2-(3-methoxyphenyl)oxazole.

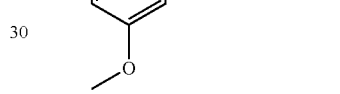

C13H14INO2 (343.17), MS(ESI): 344 (M+H$^+$).

Analogously to the building block synthesis of 4-iodomethyl-5-phenyl-2-p-tolyl-oxazole, 1-ethyl-1,2-propanedione-2-oxime and p-tolualdehyde gave 4-iodomethyl-5-ethyl-2-p-tolylazole.

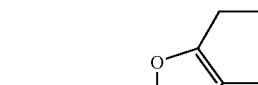

C13H14INO (327.17), MS(ESI): 328 (M+H$^+$).

Analogously to the building block synthesis of 4-iodomethyl-5-phenyl-2-p-tolyl-oxazole, 1-ethyl-1,2-propanedione-2-oxime and 2,6-dimethylbenzaldehyde gave 4-iodomethyl-5-ethyl-2-(2,6-dimethylphenyl)oxazole.

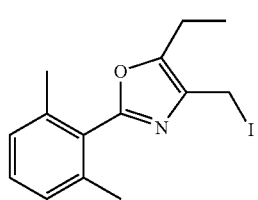

C14H16INO (341.19), MS(ESI): 342 (M+H$^+$).

Analogously to the building block synthesis of 4-iodomethyl-5-phenyl-2-p-tolyl-oxazole, 1-ethyl-1,2-propanedione-2-oxime and 2-trifluoromethylbenzaldehyde gave 4-iodomethyl-5-ethyl-2-(2-trifluoromethylphenyl)oxazole.

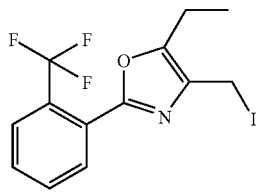

C13H11F3INO (381,14), MS(ESI): 382 (M+H⁺).

Analogously to the building block synthesis of 4-iodomethyl-5-phenyl-2-p-tolyl-oxazole, 1-cyclohexyl-1,2-propanedione-2-oxime and m-anisaldehyde gave 4-iodomethyl-5-cyclohexyl-2-(3-methoxyphenyl)oxazole.

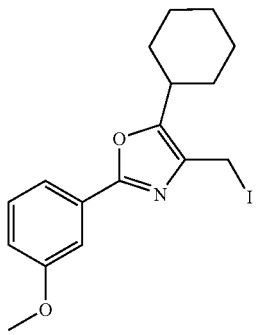

C17H20INO2 (397.26), MS(ESI): 398 (M+H⁺).

Analogously to the building block synthesis of 4-iodomethyl-5-phenyl-2-p-tolyl-oxazole, 1-cyclohexyl-1,2-propanedione-2-oxime and p-tolualdehyde gave 4-iodomethyl-5-cyclohexyl-2-p-tolyloxazole.

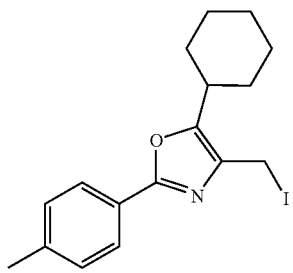

C17H20INO (381.26), MS(ESI): 382 (M+H⁺).

Analogously to the building block synthesis of 4-iodomethyl-5-phenyl-2-p-tolyl-oxazole, diacetylmonoxime and p-tolualdehyde gave 4-iodomethyl-5-methyl-2-p-tolyloxazole.

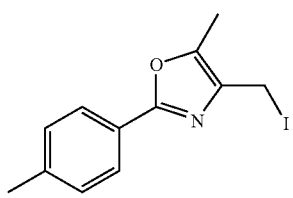

C12H12INO (313.14), MS(ESI): 314 (M+H⁺).

Analogously to the building block synthesis of 4-chloromethyl-5-phenyl-2-p-tolyl-oxazole, diacetylmonoxime and benzaldehyde gave 4-chloromethyl-5-methyl-2-phenyloxazole.

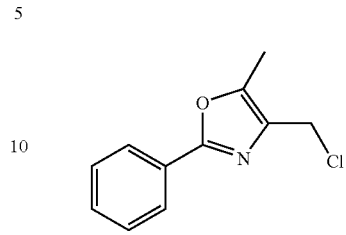

C11H10INO (207.66), MS(ESI): 208 (M+H⁺).

Analogously to the building block synthesis of 4-iodomethyl-5-phenyl-2-p-biphenyl-oxazole, diacetylmonoxime and p-biphenylcarbaldehyde gave 4-iodomethyl-5-methyl-2-p-biphenyloxazole.

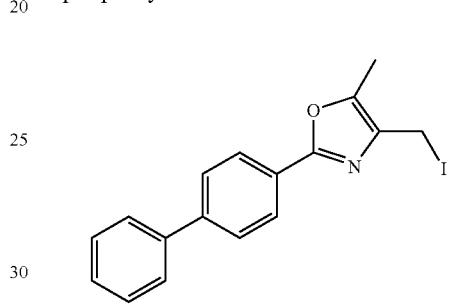

C12H12INO (375.21), MS(ESI): 376 (M+H⁺).

Analogously to the building block synthesis of 4-iodomethyl-5-phenyl-2-p-tolyl-oxazole, diacetylmonoxime and 2-naphthalenecarbaldehyde gave 4-iodomethyl-5-methyl-2-naphthyloxazole.

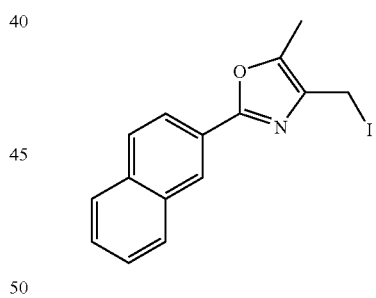

C12H12INO (349.17), MS(ESI): 350 (M+H⁺).

Analogously to the building block synthesis of 4-iodomethyl-5-phenyl-2-p-tolyl-oxazole, diacetylmonoxime and 2,4-dimethylbenzaldehyde gave 4-iodomethyl-5-methyl-2-(2,4-dimethylphenyl)oxazole.

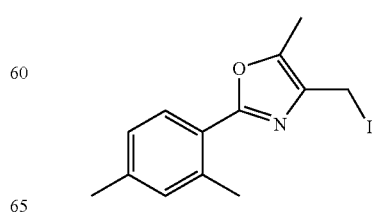

C13H14INO (327.17), MS(ESI): 328 (M+H⁺).

Analogously to the building block synthesis of 4-iodomethyl-5-phenyl-2-p-tolyl-oxazole, diacetylmonoxime and 2,6-dimethylbenzaldehyde gave 4-iodomethyl-5-methyl-2-(2,6-dimethylphenyl)oxazole.

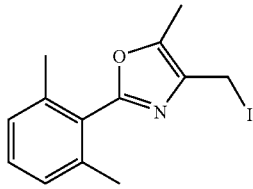

C13H14INO (327,17), MS(ESI): 328 (M+H+).

Analogously to the building block synthesis of 4-iodomethyl-5-phenyl-2-p-tolyl-oxazole, diacetylmonoxime and m-anisaldehyde gave 4-iodomethyl-2-(3-methoxy-phenyl)-5-methyloxazole.

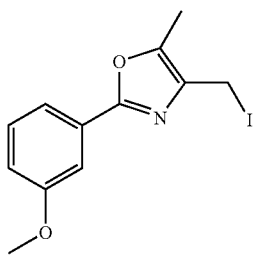

C12H12INO2 (329.14), MS(ESI): 330 (M+H+).

Analogously to the building block synthesis of 4-iodomethyl-5-phenyl-2-p-tolyl-oxazole, diacetylmonoxime and 3-trifluoromethylbenzaldehyde gave 4-iodomethyl-5-methyl-2-(3-trifluoromethylphenyl)oxazole.

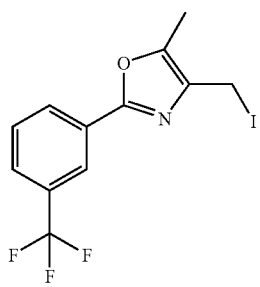

C12H9F3INO (367.11), MS(ESI): 368 (M+H+).

Analogously to the-building block synthesis of 4-iodomethyl-5-phenyl-2-p-tolyl-oxazole, diacetylmonoxime and 4-fluorobenzaldehyde gave 2-(4-fluorophenyl)-4-iodomethyl-5-methyloxazole.

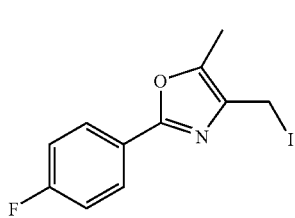

C11H9FINO (317.1 0), MS(ESI):318 (M+H+).

Analogously to the building block synthesis of 4-iodomethyl-5-phenyl-2-p-tolyl-oxazole, diacetylmonoxime and 4-methoxybenzaldehyde gave 4-iodomethyl-2-(4-methoxyphenyl)-5-methyloxazole.

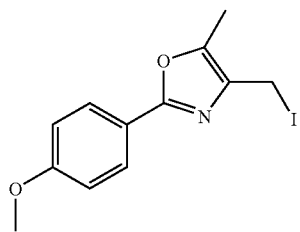

C12H12INO2 (329.14), MS(ESI):330 (M+H+).

Analogously to the building block synthesis of 4-iodomethyl-5-phenyl-2-p-tolyl-oxazole, diacetylmonoxime and 4-trifluoromethylbenzaldehyde gave 4-iodomethyl-5-methyl-2-(4-trifluoromethylphenyl)oxazole.

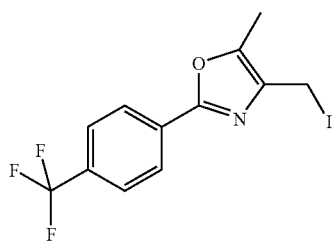

C12H9F3INO (367.11), MS(ESI):368 (M+H+).

Analogously to the building block synthesis of 4-iodomethyl-5-phenyl-2-p-tolyl-oxazole, diacetylmonoxime and 2-trifluoromethylbenzaldehyde gave 4-iodomethyl-5-methyl-2-(2-trifluoromethylphenyl)oxazole.

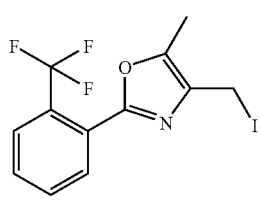

C12H9F3INO (367.11), MS(ESI):368 (M+H+).

Analogously to the building block synthesis of 4-iodomethyl-5-phenyl-2-p-tolyl-oxazole, diacetylmonoxime and m-tolualdehyde gave 4-iodomethyl-5-methyl-2-m-tolyloxazole.

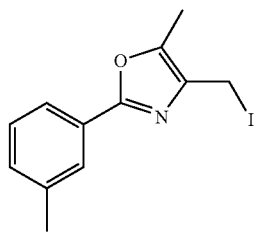

C12H12INO (313.14), MS(ESI):314 (M+H+).

Analogously to the building block synthesis of 4-iodomethyl-5-phenyl-2-p-tolyl-oxazole, diacetylmonoxime and 3-trifluoromethoxybenzaldehyde gave 4-iodo-methyl-5-methyl-2-(3-trifluoromethoxyphenyl)oxazole.

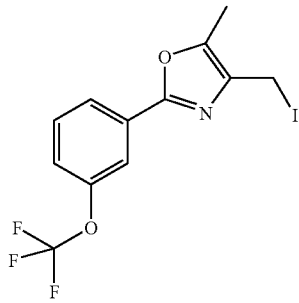

C12H9F3INO2 (383.11), MS(ESI):384 (M+H+).

Analogously to the building block synthesis of 4-iodomethyl-5-phenyl-2-p-tolyl-oxazole, diacetylmonoxime and 5-methylfuran-2-carbaldehyde gave 4-iodomethyl-5-methyl-2-(5-methylfuran-2-yl)oxazole.

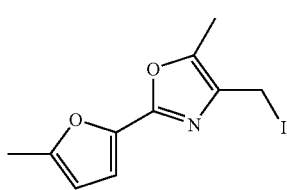

C10H10INO2 (303.11), MS(ESI):304 (M+H+).

Analogously to the building block synthesis of 4-iodomethyl-5-phenyl-2-p-tolyl-oxazole, diacetylmonoxime and thiophene-2-carbaldehyde gave 4-iodomethyl-5-methyl-2-thiophen-2-yloxazole.

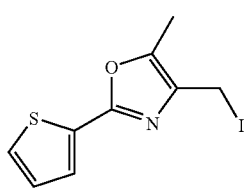

C9H8INOS (305.14), MS(ESI):306 (M+H+).

Analogously to the building block synthesis of 4-iodomethyl-5-phenyl-2-p-tolyl-oxazole, diacetylmonoxime and 4-isopropylbenzaldehyde gave 4-iodomethyl-2-(4-isopropylphenyl)-5-methyloxazole.

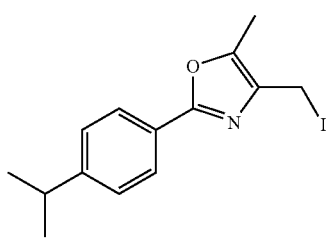

C14H16INO (341.19), MS(ESI):342 (M+H+).

EXAMPLE 1

2-Ethyl-4{(1R,3S)-3-[2-(4-fluorophenyl)-5-methyloxazol-4-ylmethoxy]-cyclohexyloxy}butanoic acid

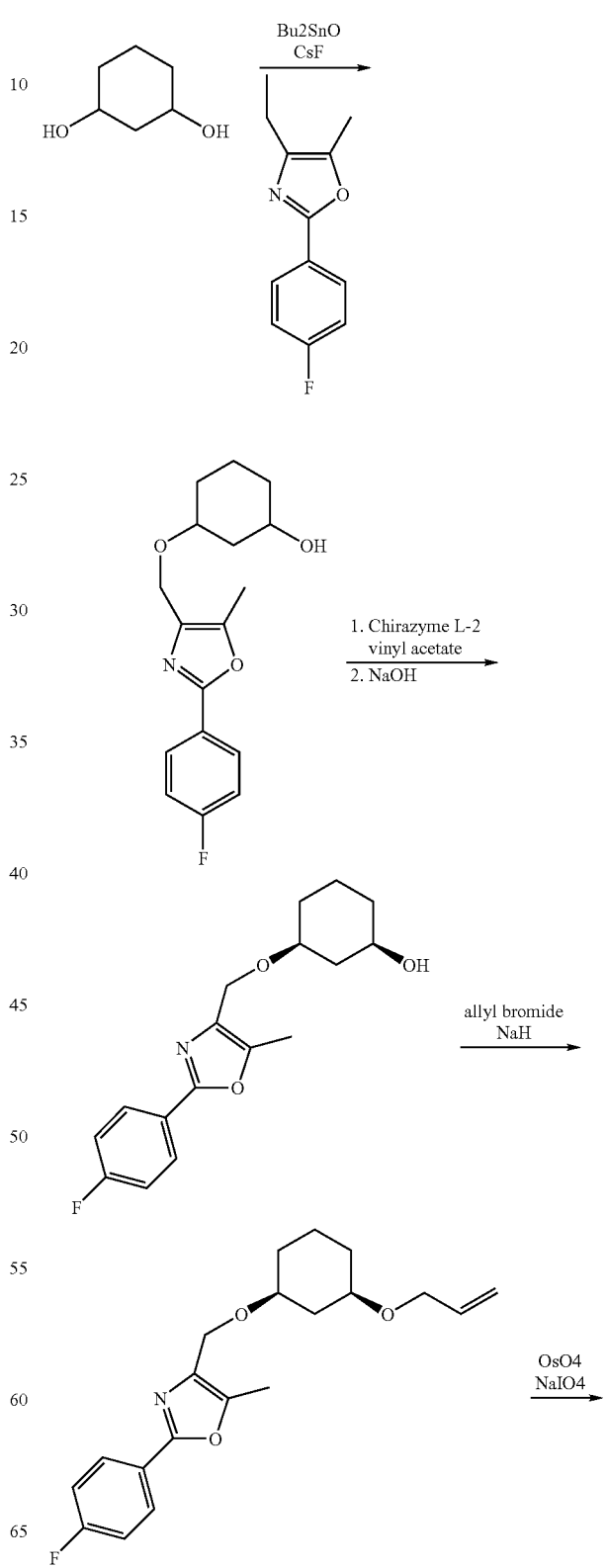

-continued

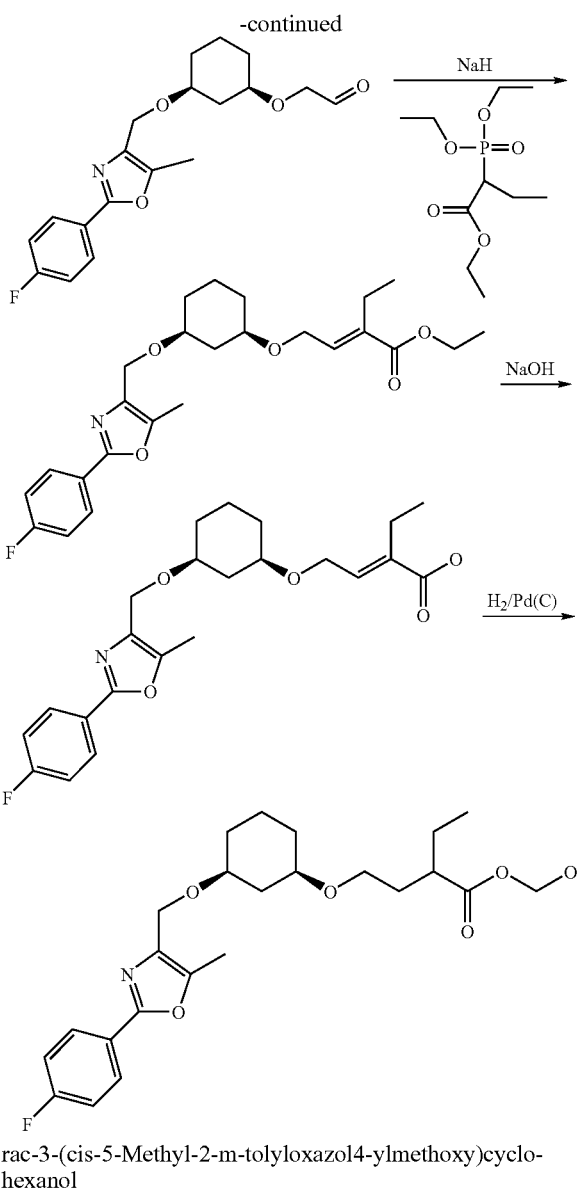

rac-3-(cis-5-Methyl-2-m-tolyloxazol4-ylmethoxy)cyclohexanol

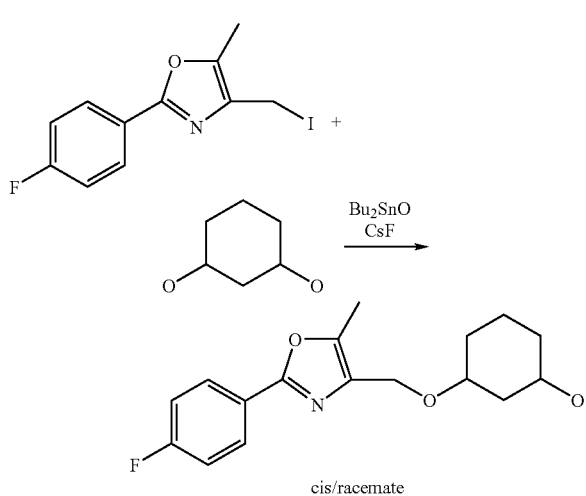

cis/racemate 21.7 g of 1,3-cyclohexanediol and 30.3 g of dibutyltin oxide are dissolved in 450 ml of toluene and, under reflux on a water separator, heated at the boil. During the reaction, the reaction volume is reduced to half the original volume. After 3 hours, the reaction mixture is cooled to room temperature and 300 ml of dimethylformamide, 29 g of 2-(4-fluorophenyl)-4-iodomethyl-5-methyloxazole and 23.5 g of cesium. fluoride are added. The mixture is stirred at room temperature for 18 hours. The reaction mixture is diluted by addition of ethyl acetate and washed with saturated sodium chloride solution. The organic phase is dried over magnesium sulfate, the solvent is removed under reduced pressure and the residue is purified by flash chromatography on silica gel (n-heptane/ethyl acetate =10:1→1:4). This gives 58 g of rac-3-[2-(4-fluorophenyl)-5-methyloxazol4-ylmethoxy]cyclohexanol as a yellowish solid which is recrystallized from n-heptane/ethyl acetate. C17H20FNO3 (305.35), MS(ESI): 306 (M+H+).

3-[2-(4-Fluorophenyl)-5-methyloxazol-4-ylmethoxy]cyclohexanol

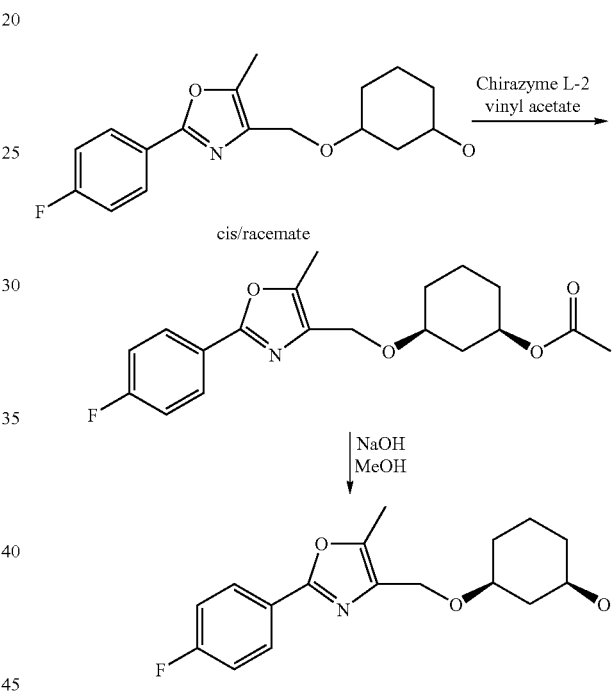

25 g of rac-3-[2-(4-fluorophenyl)-5-methyloxazol4-ylmethoxy]cyclohexanol are dissolved in 320 ml of vinyl acetate, and 1.3 g of Chirazyme L-2 Lyo (Boehringer Mannheim) are added. After about three hours of stirring at room temperature (checked by LC-MS for 40-45% conversion), the enzyme is filtered off and washed with ethyl acetate, and the solvent is removed under reduced pressure. The residue is purified by flash chromatography on silica gel (n-heptane/ethyl acetate=3:1). This gives 8 g of the acetate as a colorless oil. C19H22FNO4 (347.39), MS (ESI): 348 (M+H+). The acetate is taken up in 170 ml of methanol and, after addition of 27 ml of 2N NaOH, stirred at room temperature for one hour. Most of the solvent is removed under reduced pressure. After addition of in each case 150 ml of water and ethyl acetate, the organic phase is washed with sodium chloride solution. The organic phase is dried over magnesium sulfate and the solvent is removed under reduced pressure. This gives 6.7 g of 3-(1R,3S)-cis-3-[2-(4-fluorophenyl)-5-methyloxazol-4-ylmethoxy]cyclohexanol as a yellowish solid.

C17H20FNO3 (305.35), MS (ESI): 306 (M+H+).

4-(3-Allyloxycyclohexyloxymethyl)-2-(4-fluorophenyl)-5-methyloxazole

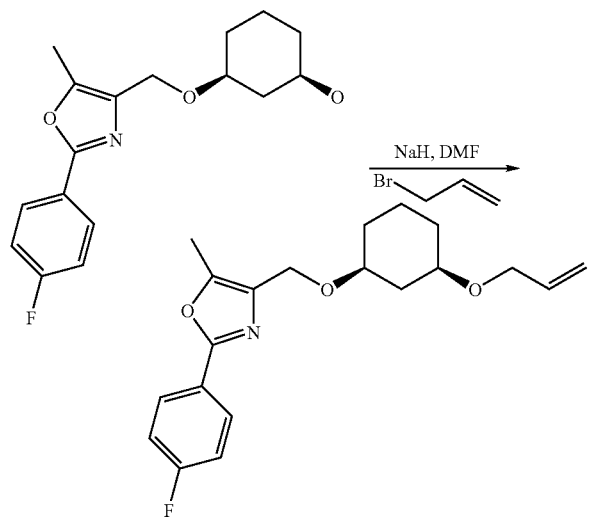

2 g of the 3-[2-(4-fluorophenyl)-5-methyloxazol-4-ylmethoxy)cyclohexanol are dissolved in 15 ml of dimethylformamide, and 0.3 g of sodium hydride is added.

After 30 minutes, 2.4 g of allyl bromide are added dropwise. The mixture is stirred at room temperature for 5 hours. 15 ml of 1 N HCl are then added to the reaction mixture, and the mixture is washed three times with 15 ml of ethyl acetate. The organic phase is dried over magnesium sulfate and the solvent is then removed under reduced pressure. The residue is purified by RP-HPLC. This gives 2.4 g of 4-(3-allyloxycyclohexyloxymethyl)-2-(4-fluorophenyl)-5-methyloxazole as a yellowish oil. C20H24FNO3 (345.42) MS(ESI): 346 (M+H+)

[3-[2-(4-Fluorophenyl)-5-methyloxazol-4-ylmethoxy]cyclohexyl]acetaldehyde

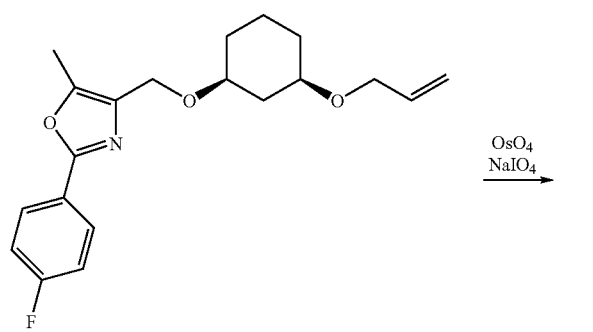

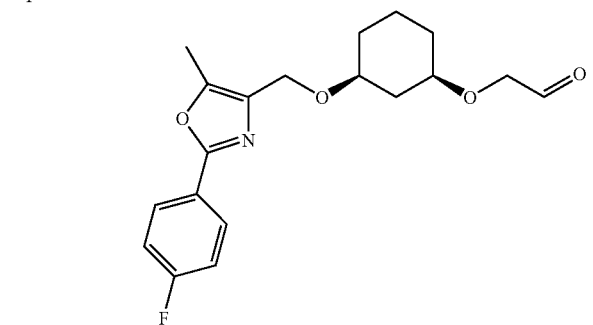

2.0 g of 4-(3-allyloxycyclohexyloxymethyl)-2-(4-fluorophenyl)-5-methyloxazole are dissolved in 50 ml of diethyl ether, and 3.8 g of sodium periodate, dissolved in 50 ml of water, are added. At 0° C., 1 ml of an osmium tetroxide solution (2.5% by weight in tert-butanol) is added, and the mixture is stirred vigorously at room temperature. After 8 h, 100 ml of methyl tert-butyl ether are added and the mixture is washed with a saturated sodium thiosulfate solution. The organic phase is dried over magnesium sulfate and the solvent is removed under reduced pressure. The residue is purified on silica gel (n-heptane:ethyl acetate=1:1→1:5). This gives 1.4 g of [3-[2-(4-fluorophenyl)-5-methyloxazol-4-ylmethoxy]cyclohexyl]-acetaldehyde as a yellow-brown oil. C20H25NO4 (343.42), MS(ESI): 344 (M+H+), R$_f$(n-heptane:ethyl acetate=1:1)=0.25.

Ethyl 2-ethyl4-{(1R,3S)-3-[2-(4-fluorophenyl)-5-methyloxazol-4-ylmethoxy]-cyclohexyloxy}but-2-enoate

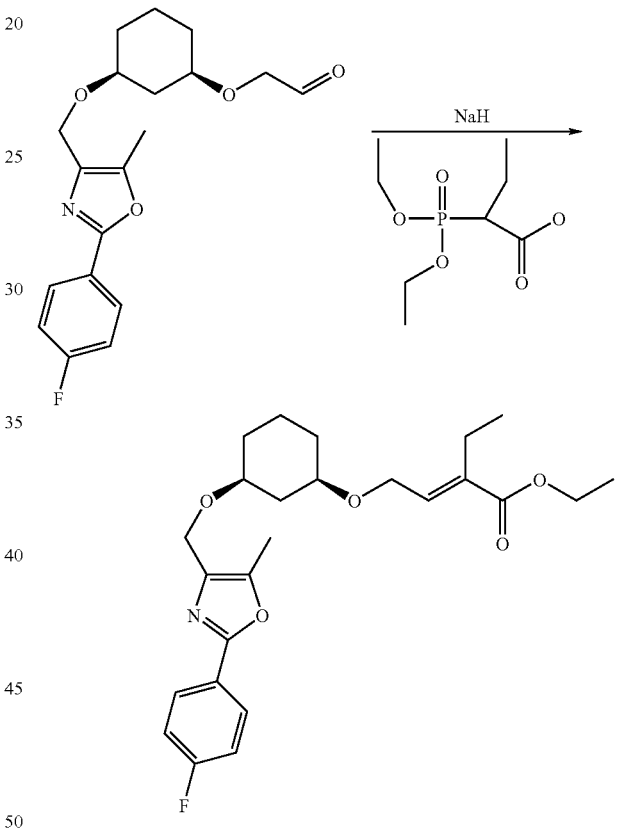

0.58 g of ethyl 2-(diethoxyphosphoryl)butanoate is dissolved in tetrahydrofuran (20 ml), and 0.06 g of sodium hydride is added at 0° C. The suspension is stirred at 0° C. for 30 min and at room temperature for 30 min and then cooled to −70° C. After addition of 0.4 g of 2-((1R,3S)-[3-(5-methyl-2-m-tolyloxazol4-ylmethoxy)cyclohexyloxy]acetaldehyde (dissolved in 5 ml of tetrahydrofuran), the mixture is stirred at −70° C. for 60 min and then at room temperature for 12 h. 10 ml of water are added, the mixture is extracted with ethyl acetate (3×10 ml) and the combined organic phases are washed with saturated sodium chloride solution (10 ml). The solvent is removed under reduced pressure and the residue is purified by HPLC. This gives 0.32 g of ethyl 2-ethyl-4-{(1R,3S)-3-[2-(4-fluorophenyl)-5-methyloxazol-4-ylmethoxy]cyclohexyloxy}but-2-enoate C25H32FNO5 (445.54) MS(ESI): 446 (M+H+)

2-Ethyl-4-{(1R,3S)-3-[2-(4-fluorophenyl)-5-methyloxazol-4-ylmethoxy]-cyclohexyloxy}but-2-enoic acid

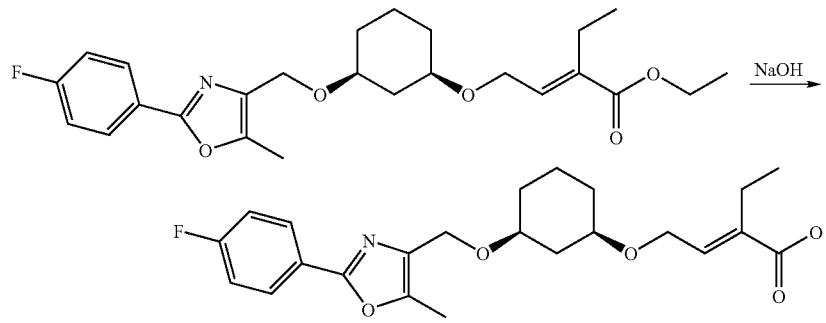

0.5 g of ethyl 2-ethyl-4-{(1R,3S)-3-[2-(4-fluorophenyl)-5-methyloxazol-4-ylmethoxy]cyclohexyloxy}but-2-enoate is dissolved in 5 ml of methanol, and 2.5 ml of a 1N aqueous sodium hydroxide solution are added. After 12 h of stirring at room temperature, the mixture is acidified with 3 ml of 1 N hydrochloric acid and the resulting precipitate is taken up in ethyl acetate. The solvent is removed under reduced pressure and the residue of the ester hydrolysis, 2-ethyl4-{(1R,3S)-3-[2-(4-fluorophenyl)-5-methyloxazol-4-ylmethoxy]cyclohexyloxy}but-2-enoic acid, is obtained as 0.45 g of a white solid. C23H28FNO$_5$ (417.48) MS(ESI): 418 (M+H$^+$)

2-Ethyl-4-{(1R,3S)-3-[2-(4-fluorophenyl)-5-methyloxazol-4-ylmethoxy]cyclohexyl-oxy}butanoic acid

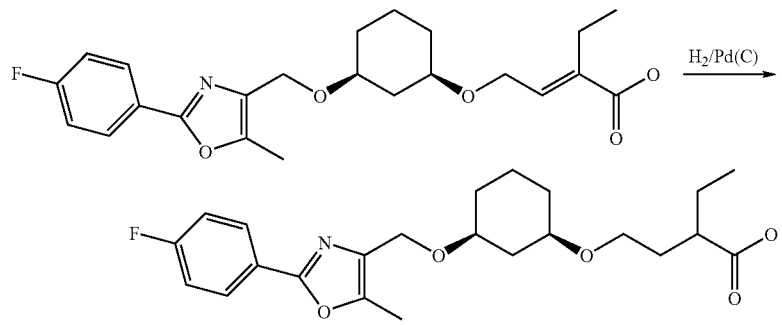

0.3 g of the 2-ethyl-4-{(1R,3S)-3-[2-(4 fluorophenyl)-5-methyloxazol-4-ylmethoxy]-cyclohexyloxy}but-2-enoic acid is dissolved in a solvent mixture of 2 ml of ethyl acetate and 1 ml of methanol, and 0.05 g of palladium (10% on carbon) is added.

The mixture is then hydrogenated at a hydrogen pressure of 1 bar for 3 h. After removal of the palladium by filtration, the solvent mixture is removed under reduced pressure and the residue is recrystallized from acetonitrile. This gives 0.25 g of 2-ethyl-4-{(1R,3S)-3-[2-(4-fluorophenyl)-5-methyloxazol-4-ylmethoxy ]-cyclohexyloxy}butanoic acid as a white solid. C$_{23}$H$_{30}$FNO$_5$ (419.49), MS(ESI): 420 (M+H$^+$)

EXAMPLE 2

Analogously to Example 1, 2-((1R,3S)-[3-(2-(4-fluorophenyl)-5-methyloxazol-4-yl-methoxy)cyclohexyloxy] acetaldehyde and ethyl 2-(d iethoxyphosphoryl)pentanoate give 2-propyl-4-[3-(4-fluorophenyl)-5-methyloxazol-4-yl-methoxy)cyclohexyloxy]-butanoic acid.

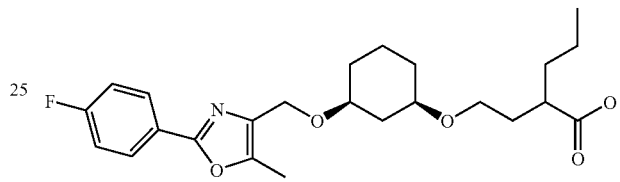

C$_{24}$H$_{32}$FNO$_5$ (433.52) MS(ESI): 434 (M+H$^+$)

EXAMPLE 3

Analogously to Example 1, 2-(1R,3S)-[3-(2-(4-fluorophenyl)-5-methyloxazol-4-yl-methoxy)cyclohexyloxy] acetaldehyde and ethyl 2-(diethoxyphosphoryl)acetate give 4-{3-[2-(4-fluorophenyl)-5-methyloxazol-4-ylmethoxy]cyclohexyloxy}butanoic acid

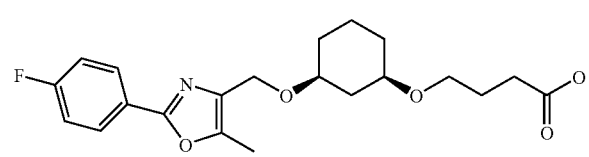

C$_{21}$H$_{26}$FNO$_5$ (391.44) MS(ESI): 392 (M+H$^+$)

EXAMPLE 4

Analogously to Example 1, 2-(1R,3S)-[3-(2-(4-fluorophenyl)-5-methyloxazol-4-yl-methoxy)cyclohexyloxy] acetaldehyde and ethyl 2-(diethoxyphosphoryl)propionate give 4-{3-[2-(4-fluorophenyl)-5-methyloxazol-4-yl-methoxy]cyclohexyloxy}-2-methyl-butanoic acid

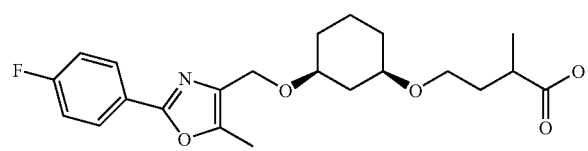

C22H28FNO5 (405.47) MS(ESI): 406 (M +H+)

EXAMPLE 5

Ethyl (1R,3S)-2-[3-(5-methyl-2-m-tolyloxazol-4-yl-methoxy)cyclohexyloxymethyl]-acrylate

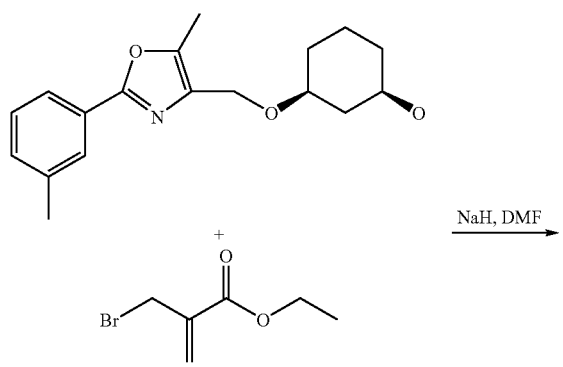

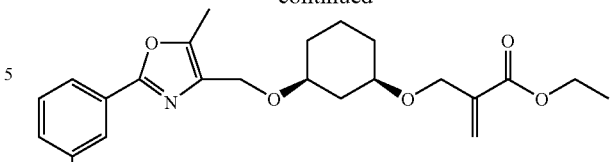

At room temperature, 200 mg of a 60% strength sodium hydride suspension are added to a solution of 754 mg of 3-(1R,3S)-cis-5-methyl-2-m-tolyloxazol-4-yl-methoxy) cyclohexanol in 10 ml of dimethylformamide/ 5 ml of tetrahydrofuran, and the mixture is stirred at room temperature for 20 min. At 0° C., 1 g of ethyl 2-bromo-methylacrylate is then added, and the mixture is stirred at this temperature for 2 h.

100 ml of ethyl acetate and 150 ml of sat. NaCl solution are added. The organic phase is dried over sodium sulfate, the solvent is removed under reduced pressure and the residue is purified by flash chromatography on silica gel (n-heptane/ethyl acetate=2:1). This gives 1.18 g of ethyl ((1R,3S)-2-[3-(5-methyl-2-m-tolyloxazol-4-ylmethoxy)cyclohexyloxymethyl]acrylate as a colorless oil. $C_{24}H_{31}NO_5$ (413.52), MS (ESI): 414 (M+H+).

Ethyl (1R,3S)-1-[3-(5-methyl-2-m-tolyloxazol-4-yl-methoxy)cyclohexyloxymethyl]-cyclopropanecarboxylate

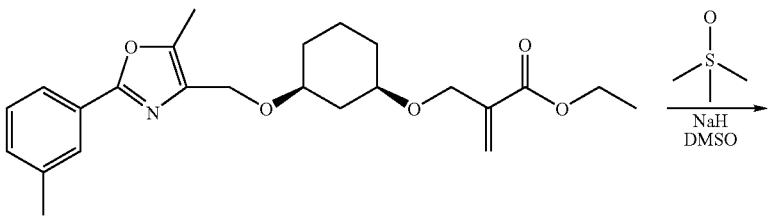

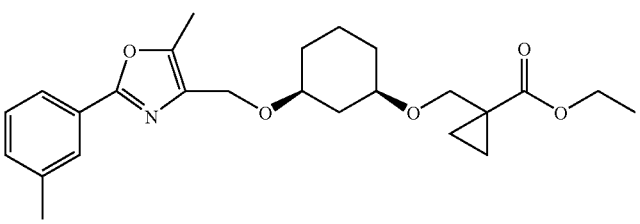

At room temperature, 12 mg of a 60 percent strength sodium hydride suspension are added to a suspension of 55 mg of trimethylsulfonium iodide in 2 ml of DMSO, and the mixture is stirred at room temperature for 20 min. At 10° C. 100 mg of ethyl (1R,3S)-2-[3-(5-methyl-2-m-tolyloxazol4-ylmethoxy)cyclohexyloxymethyl]acrylate, dissolved in 2 ml of DMSO, are then added, and the mixture is stirred at room temperature for 90 min. The mixture is poured into ice-water and extracted with methyl tert-butyl ether. The organic phase is dried over sodium sulfate, the solvent is removed under reduced pressure and the residue is purified by flash chromatography on silica gel (n-heptane/ethyl acetate=2:1). This gives ethyl (1R,3S)-1-[3-(5-methyl-2-m-tolyloxazol-4-yl-methoxy)cyclohexyloxymethyl]cyclo-propanecarboxylate as a colorless oil. $C_{25}H_{33}NO_5$ (427.55), MS (ESI): 428 (M+H+).-

(1R,3S)-1-[3-(5-methyl-2-m-tolyloxazol-4-ylmethoxy)cyclohexyloxymethyl]cyclo-propanecarboxylic acid

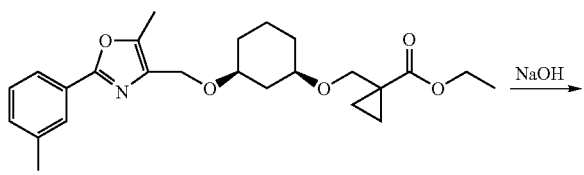

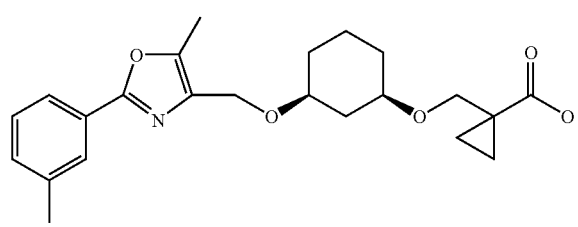

56 mg of ethyl (1R,3S)-1-[3-(5-methyl-2-m-tolyloxazol4-ylmethoxy)-cyclohexyloxymethyl]cyclopropanecarboxylate are dissolved in 3 ml of methanol, 0.5 ml of 5N NaOH is added and the mixture is stirred at room temperature for 18 h. The solvent is removed under reduced pressure and the residue is acidified with trifluoroacetic acid and purified by RP-HPLC. This gives (1R,3S)-1-[3-(5-methyl-2-m-tolyloxazol-4-ylmethoxy)cyclohexyloxymethyl]cyclopropanecarboxylic acid as a colorless oil. $C_{23}H_{29}NO_5$ (399.49), MS (ESI): 400 (M+H$^+$).

EXAMPLE 6

Ethyl 2R/S-(1R',3S')-2-[(methylphenethylamino)methyl]-3-[3-(5-methyl-2-m-tolyl-oxazol-4-ylmethoxy)cyclohexyloxy]propionate

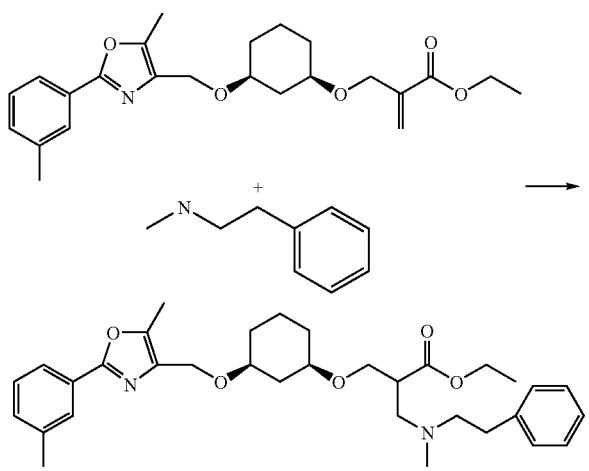

50 mg of ethyl (1R,3S)-2-[3-(5-methyl-2-m-tolyloxazol-4-ylmethoxy)cyclo-hexyloxymethyl]acrylate are dissolved in 5 ml of ethanol, 95 mg of N-methylhomo-benzylamine are added and the mixture is stirred at room temperature for 18 h.

The solvent is removed under reduced pressure and the residue is purified by flash chromatography on silica gel (n-heptane/ethyl acetate=1:1+3% NEt$_3$). This gives ethyl 2R/S-(1R',3S')-2-[(methylphenethylamino)methyl]-3-[3-(5-methyl-2-m-tolyloxazol-4-ylmethoxy)cyclohexyloxy]propionate as a colorless oil. $C_{33}H_{44}N_2O_5$ (548.73), MS (ESI): 549 (M+H$^+$).

((1R',3S')-2 R/S-[(Methylphenethylamino)methyl]-3-[3-(5-methyl-2-m-tolyloxazol-4-ylmethoxy)cyclohexyloxy]propionic acid

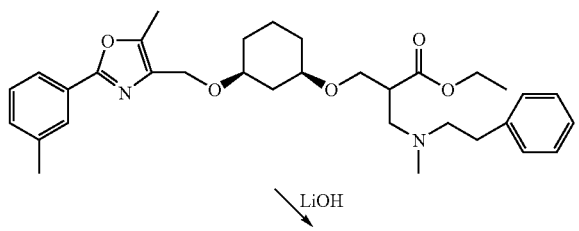

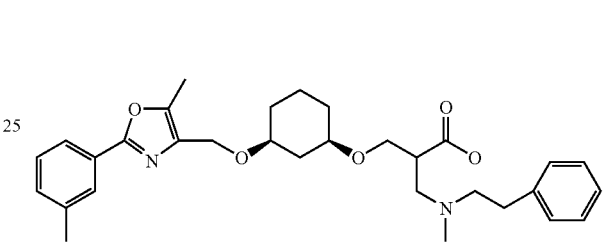

65 mg of ethyl 2R/S-((1R',3S')-2-[(methylphenethylamino)methyl]-3-[3-(5-methyl-2-m-tolyloxazol-4-ylmethoxy)cyclohexyloxy]propionate are dissolved in 3 ml of tetrahydrofuran/methanol 3:1, 0.6 ml of 1N LiOH is added and the mixture is stirred at room temperature for 6 h. The solvent is removed under reduced pressure and the residue is acidified with trifluoroacetic acid and purified by RP-HPLC. This gives 2R/S-((1R',3S') [(methylphenethylamino) methyl]-3-[3-(5-methyl-2-m-tolyl-oxazol-4-ylmethoxy)cyclohexyloxy]propionic acid as a colorless oil. $C_{31}H_{40}N_2O_5$ (520.67), MS (ESI): 521 (M+H$^+$).

EXAMPLE 7

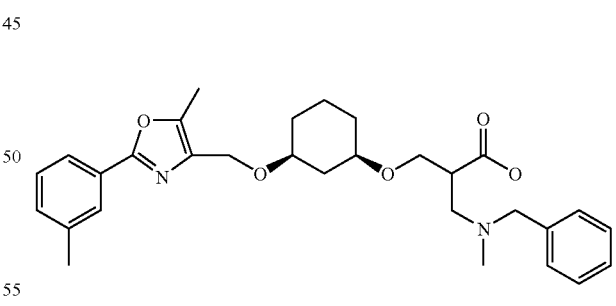

(1R',3S')-2R/S-[(Benzylmethylamino)methyl]-3-[3-(5-methyl-2-m-tolyloxazol-4-yl-methoxy)cyclohexyloxy]propionic acid Ethyl (1R,3S)-2-[3-(5-methyl-2-m-tolyloxazol-4-ylmethoxy)cyclohexyloxy-methyl]acrylate and N-methylbenzylamine give, analogously to Example 100, (1R',3S')-2R/S-[(benzylmethylamino)methyl]-3-[3-(5-methyl-2-m-tolyloxazol-4-yl-methoxy)cyclohexyloxy]propionic acid of molecular weight 506.65 ($C_{30}H_{38}N_2O_5$), MS(ESI): 507.20 (M+H$^+$).

EXAMPLE 8

(1R',3S')-2R/S-Methoxymethyl-3-[3-(5-methyl-2-m-tolyloxazol-4-ylmethoxy)cyclo-hexyloxy]propionic acid

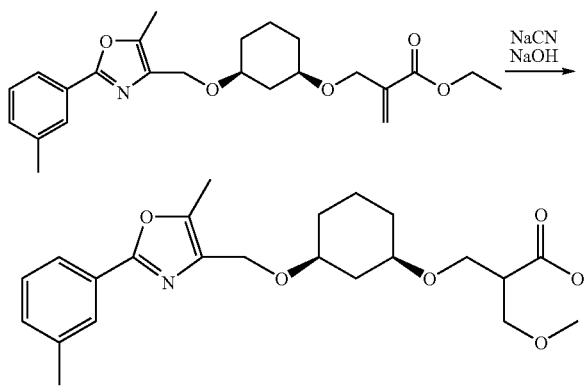

56 mg of ethyl (1R,3S)-2-[3-(5-methyl-2-m-tolyloxazol-4-ylmethoxy)cyclohexyloxy-methyl]acrylate are dissolved in 3 ml of methanol, 49 mg of sodium cyanide and 0.25 ml of 2N NaOH are added and the mixture is stirred at room temperature for 18 h. The solvent is removed under reduced pressure and the residue is acidified with trifluoroacetic acid and purified by RP-HPLC. This gives (1R',3S')-2R/S-methoxymethyl-3-[3-(5-methyl-2-m-tolyloxazol-4-ylmethoxy)cyclohexyloxy]-propionic acid as a colorless oil. $C_{23}H_{31}NO_6$ (417.51), MS (ESI): 418.15 (M+H$^+$).

EXAMPLE 9

Ethyl Z-(1R',3S')-3-(4-fluoro-3-methylphenyl)-2-[3-(5-methyl-2-m-tolyloxazol-4-yl-methoxy)cyclohexyloxymethyl]acrylate

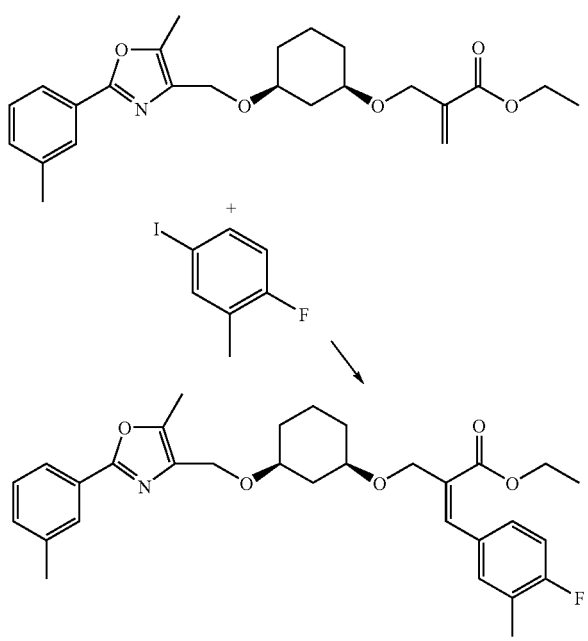

220 mg of tetrabutylammonium chloride and 332 mg of potassium carbonate are suspended in 4 ml of dimethylformamide and stirred intensively for 20 min. 400 mg of ethyl (1R,3S)-2-[3-(5-methyl-2-m-tolyloxazol-4-ylmethoxy)cyclohexyloxy-methyl]acrylate, 25 mg of triphenylphosphine and 212 mg of 4-fluoro-3-methyliodo-benzene are added, the mixture is degassed and vented with argon and 10 mg of palladium acetate and 0.2 mol of water are added. The mixture is heated at 60° C for 4 h. After cooling, 20 ml of ethyl acetate and 50 ml of sat. NaCl solution are added. The organic phase is dried over sodium sulfate, the solvent is removed under reduced pressure and the residue is purified by flash chromatography on silica gel (n-heptane/ethyl acetate=4:1). This gives ethyl Z-(1R',3S')-3-(4-fluoro-3-methylphenyl)-2-[3-(5-methyl-2-m-tolyloxazol-4-ylmethoxy)cyclohexyloxymethyl]-acrylate as a colorless oil. $C_{31}H_{38}FNO_5$ (523.65), MS (ESI): 524 (M+H$^+$).

Ethyl 2R/S-(4-fluoro-3-methylbenzyl)-(1R',3S')-3-[3-(5-methyl-2-m-tolyloxazol4-ylmethoxy)cyclohexyloxy]propionate

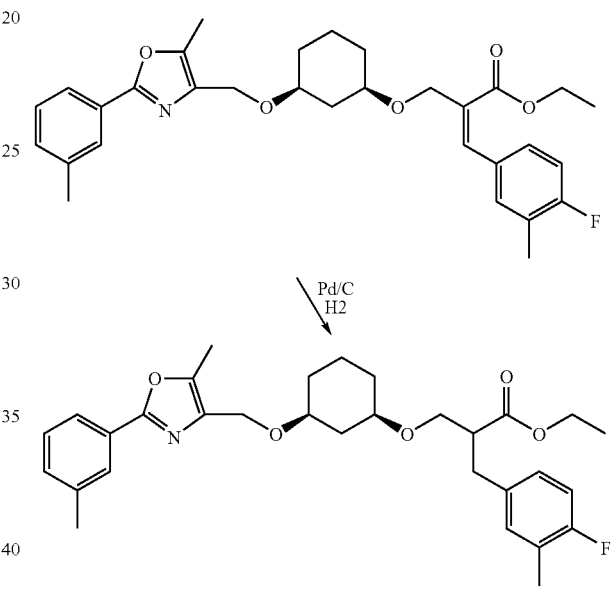

80 mg of ethyl Z-(1R',3S')-3-(4-fluoro-3-methylphenyl)-2-[3-(5-methyl-2-m-tolyl-oxazol-4-ylmethoxy)cyclohexyloxymethyl]acrylate are dissolved in 15 ml of ethyl acetate and, after addition of 30 mg of Pd/C 10%, stirred under 1 bar of H$_2$ for 24 h. The catalyst is filtered off and the solvent is evaporated. This gives ethyl 2R/S-(4-fluoro-3-methylbenzyl)-(1R',3S')-3-[3-(5-methyl-2-m-tolyloxazol-4-yl-methoxy)cyclohexyloxy]propionate as a colorless oil. $C_{31}H_{38}FNO_5$ (521.63), MS (ESI): 522 (M+H$^+$). $C_{31}H_{38}FNO_5$ (521.63), MS (ESI): 522 (M+H$^+$).

(2R/S)-(4-Fluoro-3-methylbenzyl)-(1R',3S')-3-[3-(5-methyl-2-m-tolyloxazol-4-yl-methoxy)cyclohexyloxy]propionic acid

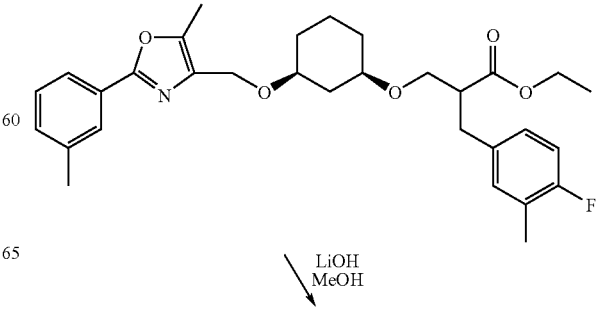

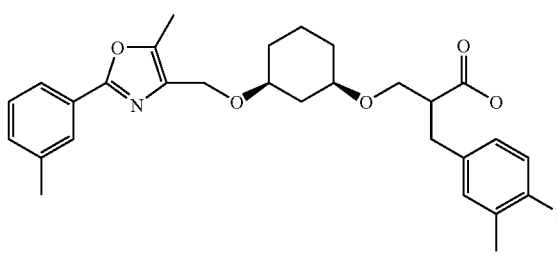

70 mg of ethyl 2R/S-(4-fluoro-3-methylbenzyl)-(1R',3S')-3-[3-(5-methyl-2-m-tolyl-oxazol-4-ylmethoxy)cyclohexyloxy]propionate are dissolved in 3 ml of tetrahydro-furan/methanol 3:1, 0.1 ml of 1 N LiOH are added and the mixture is stirred at, room temperature for 18 h. The solvent is removed under reduced pressure and the residue is acidified with trifluoroacetic acid and purified by RP-HPLC. This gives 2R/S-(4-fluoro-3-methylbenzyl)-(1R',3S')-3-[3-(5-methyl-2-m-tolyloxazol-4-yl-methoxy)cyclohexyloxy]propionic acid as a colorless oil. $C_{29}H_{34}FNO_5$ (495.60), MS (ESI): 496.20 (M+H$^+$).

EXAMPLE 10 rac-3-(cis-5-Methyl-2-m-tolyloxazol-4-ylmethoxy)cyclohexanol

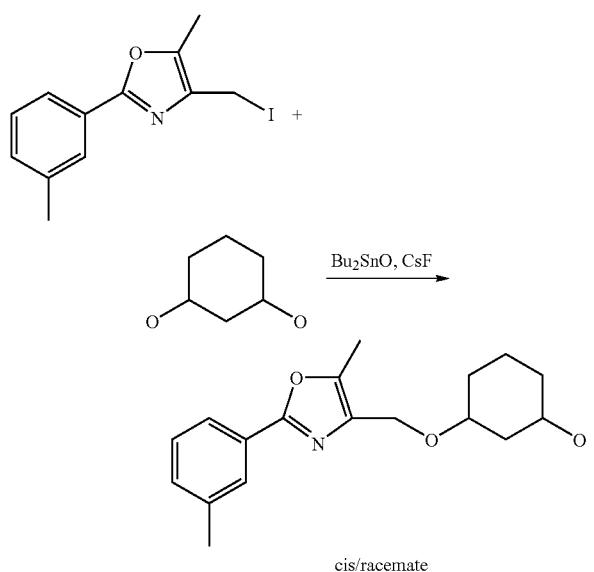

21.7 g of 1,3-cyclohexanediol and 30.3 g of dibutyltin oxide are dissolved in 450 ml of toluene and, under reflux on a water separator, heated at the boil. During the reaction, the reaction volume is reduced to half its original volume. After 3 hours, the reaction mixture is cooled to room temperature and 300 ml of dimethyl-formamide, 29 g of 4-iodomethyl-5-methyl-2-m-tolyloxazole 1 and 23.5 g of cesium fluoride are added. The mixture is stirred at room temperature for 18 hours. The reaction mixture is diluted by addition of ethyl acetate and washed with saturated NaCl solution. The organic phase is dried over magnesium sulfate, the solvent is. removed under reduced pressure and the residue is purified by flash chromatography on silica gel (n-heptane/ethyl acetate=10:1→1:4). This gives 58 g of rac-3-(cis-5-methyl-2-m-tolyloxazol-4-ylmethoxy)cyclohexanol as a yellowish solid which is recrystallized from n-heptane/ethyl acetate. $C_{18}H_{23}NO_3$ (301.39), MS (ESI): 302 (M+H$^+$).

3-((1R,3S)-cis-5-Methyl-2-m-tolyloxazol-4-ylmethoxy)cyclohexanol 4

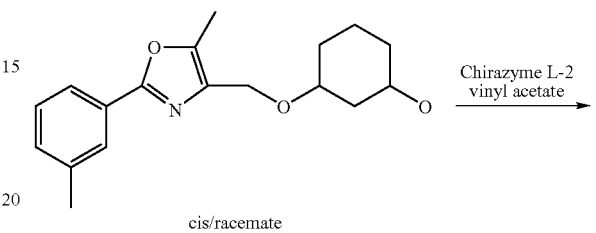

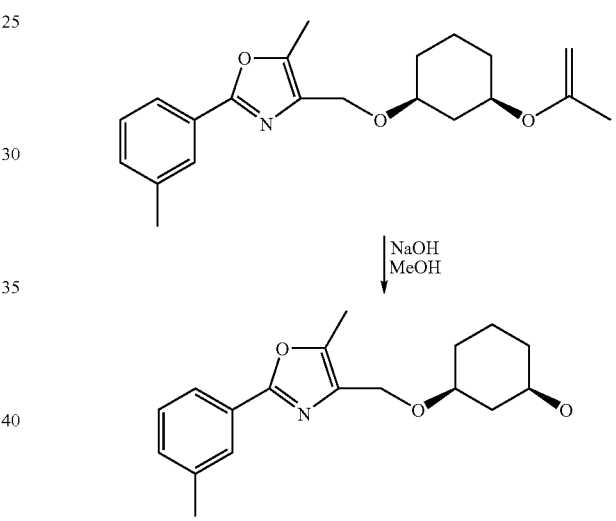

25 g of rac-3-(cis-5-methyl-2-m-tolyloxazol-4-ylmethoxy)cyclohexanol are dissolved in 320 ml of vinyl acetate, and 1.3 g of Chirazyme L-2 Lyo (Boehringer Mannheim) are added. The mixture is stirred at room temperature for about three hours (checked by LC-MS for 40-45% conversion) and the enzyme is then filtered off and washed with ethyl acetate, and the solvent is removed under reduced pressure. The residue is purified by flash chromatography on silica gel (n-heptane/ethyl acetate=3:1). This gives 8 g of acetate 3 as a colorless oil. $C_{20}H_{25}NO_4$ (343.43), MS (ESI): 344 (M+H+). The acetate is taken up in 170 ml of methanol and, after addition of 27 ml of 2N NaOH, stirred at room temperature for one hour. Most of the solvent is removed under reduced pressure. After addition of in each case 150 ml of water and ethyl acetate, the org. phase is washed with NaCl solution. The organic phase is dried over magnesium sulfate and the solvent is removed under reduced pressure. This gives 6.7 g of 3-((1R,3S)-cis-5-methyl-2-m-tolyloxazol-4-ylmethoxy)cyclohexanol as a yellowish solid. $C_{18}H_{23}NO_3$ (301.39), MS (ESI): 302 (M+H+).

4-((1R,3S)-3-Allyloxycyclohexyloxymethyl)-5-methyl-2-m-tolyloxazole 5

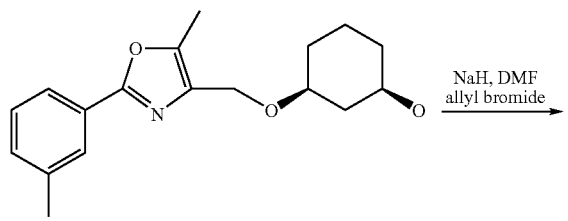

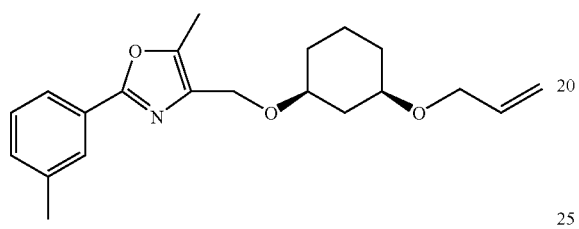

At room temperature, 470 g of a 60% strength suspension of sodium hydride are added to a solution of 2.2 g of 3-((1R,3S)-cis-5-methyl-2-m-tolyloxazol-4-yl-methoxy)cyclohexanol in 30 ml of dimethylformamide, and the mixture is stirred at room temperature for 20 minutes. 1.36 ml of allyl bromide are then added. The mixture is stirred at 40° C. until the conversion is complete; if required, further sodium hydride and allyl bromide are added. After complete conversion (checked by LC-MS), 100 ml of ethyl acetate and 150 ml of sat. NaCl solution are added. The organic phase is dried over magnesium sulfate, the solvents are removed under reduced pressure and the residue is purified by flash chromatography on silica gel (n-heptane/ethyl acetate=3:1). This gives 2.3 g of 4-((1R,3S)-3-allyl-oxycyclohexyloxymethyl)-5-methyl-2-m-tolyloxazole 5 as a colorless oil.

C21H27NO3 (341.45), MS (ESI): 342 (M+H+).

(1R',3S')-3-[3-(5-Methyl-2-m-tolyloxazol-4-ylmethoxy)cyclohexyloxy]propane-1,2-diol

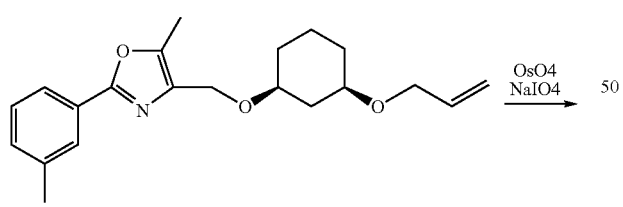

At 0° C., 225 mg of DABCO, 1.4 g of anhydrous N-methylmorpholine N-oxide and 350 pl of osmium tetroxide, 2.5% in tert-butanol, were added to 2.8 g of 4-((1R,3S)-3-allyloxycyclohexyloxymethyl)-5-methyl-2-m-tolyloxazole in 9 ml of acetone/water 10:1. After 24 h of stirring at room temperature, 2.4 g of sodium metabisulfite were added and, after 10 min, the mixture was diluted with 25 ml of CH2Cl2. The mixture was filtered and the solvent was removed under reduced pressure. The residue is purified by flash chromatography on silica gel (n-heptane/ethyl acetate=1:3). This gives 2.5 g of 2R-(1R',3S')-3-[3-(5-methyl-2-m-tolyl-oxazol-4-ylmethoxy)cyclohexyloxy]propane-1,2-diol as a colorless oil. $C_{21}H_{29}NO_5$ (375.47), MS (ESI): 376 (M+H+).

2S-(1S',3R')-1-(tert-Butyl dimethyl silanyloxy)-3-[3-(5-methyl-2-m-tolyloxazol-4-yl-methoxy)cyclohexyloxy]propan-2-ol

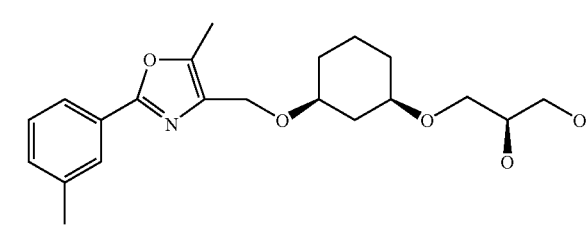

At 0° C., 500 mg of imidazole, 1.02 g of tert-butyldimethylsilyl chloride and 50 mg of tetrabutylammonium iodide are added to 2.5 g of 2R-(1. R',3S')-3-[3-(5-methyl-2-m-tolyloxazol-4-ylmethoxy)cyclohexyloxy]propane-1,2-diol in 30 ml of dichloro-methane. Over a period of 18 h, the mixture is allowed to warm to room temperature and then poured onto ice. The mixture is extracted with dichloromethane, the extract is dried over sodium sulfate and filtered and the solvent is removed under reduced pressure. The residue is purified by flash chromatography on silica gel (n-heptane/ethyl acetate=2:1→1:2). This gives 2S-(1S',3R')-1-(tert-butyl dimethyl silanyloxy)-3-[3-(5-methyl-2-m-tolyloxazol-4-ylmethoxy)cyclohexyl-oxy]propan-2-ol as a colorless oil. $C_{27}H_{43}NO_5Si$ (489.73), MS (ESI): 490 (M+H+).

2S'-(1S,3R)4-{3-[3-(tert-Butyl dimethyl silanyloxy)-2-prop-2-ynyloxypropoxy]cyclo-hexyloxymethyl}-5-methyl-2-m-tolyloxazole

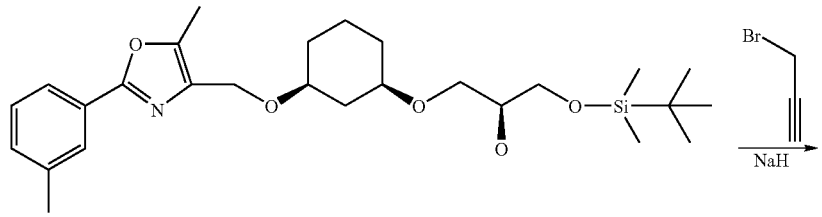

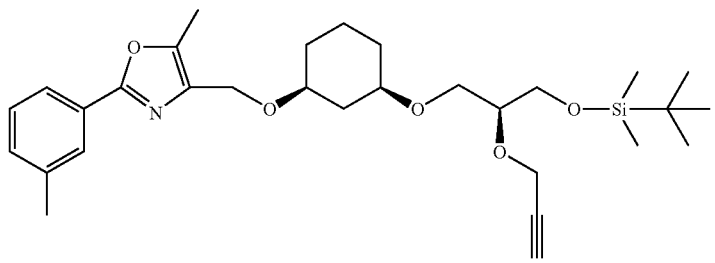

25 mg of a 60% strength sodium hydride suspension are added to 245 mg of 2S-(1S',3R')-1-(tert-butyl dimethyl silanyloxy)-3-[3-(5-methyl-2-m-tolyloxazol-4-yl-methoxy)cyclohexyloxy]propan-2-ol in 3 ml of dimethylformamide, and the mixture is stirred at room temperature for 20 min. 200 mg of propargyl bromide are then added, and the mixture is stirred at room temperature until the conversion is complete. The mixture is taken up in sat. NaCl solution/ethyl acetate, the organic phase is dried over sodium sulfate and filtered and the solvent is removed under reduced pressure. This gives 2S'-(1S,3R)-4-{3-[3-(tert-butyl dimethyl silanyloxy)-2-prop-2-ynyloxypropoxy]cyclohexyloxymethyl}-5-methyl-2-m-tolyloxazole as a colorless oil. $C_{30}H_{45}NO_5Si$ (527.78), MS (ESI): 528 (M+H$^+$).

(1R',3S')-2R-3-[3-(5-Methyl-2-m-tolyloxazol-4-ylmethoxy)cyclohexyloxy]-2-prop-2-ynyloxy-propan-1-ol

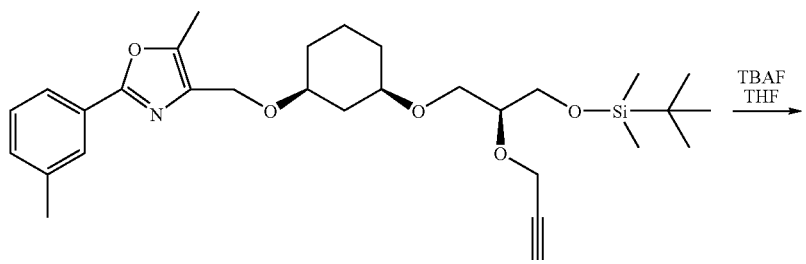

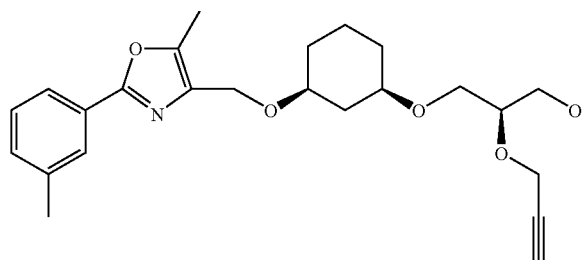

2 ml of tetrabutylammonium fluoride, 1M in tetrahydrofuran, are added to 200 mg of 2S'-(1S ,3R)4-{3-[3-(tert-butyl-dimethyl-silanyloxy)-2-prop-2-ynyloxypropoxy]-cyclohexyloxymethyl}-5-methyl-2-m-tolyloxazole in 2 ml of tetrahydrofuran, and the mixture is stirred at room temperature for 2 h. The mixture is taken up in sat. NaCl solution/ethyl acetate, the organic phase is dried over sodium sulfate and filtered and the solvent is removed under reduced pressure. This gives (1R',3S')-2R-3-[3-(5-methyl-2-m-tolyloxazol-4-ylmethoxy)cyclohexyloxy]-2-prop-2-ynyloxypropan-1-ol as a colorless oil. $C_{24}H_{31}NO_5$ (413.53), MS (ESI): 414 (M+H$^+$).

2 R-(1R',3S')-3-[3-(5-Methyl-2-m-tolyloxazol-4-yl methoxy)cyclohexyloxy]-2-propoxypropan-1-ol

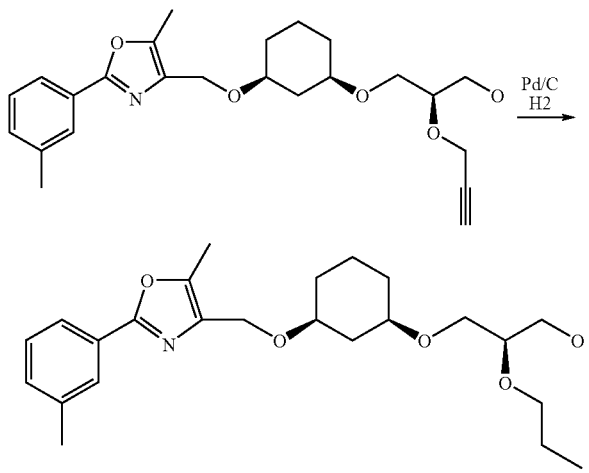

50 mg of Pd/C 10% are added to the crude product (1R',3S')-2R-3-[3-(5-methyl-2-m-tolyloxazol-4-ylmethoxy)cyclohexyloxy]-2-prop-2-ynyloxypropan-1-ol, dissolved in 20 ml of methanol, and the mixture is stirred under 1 bar of hydrogen for 3 h. The catalyst is filtered and the solvent is removed under reduced pressure. This gives 2R-(1R',3S')-3-[3-(5-methyl-2-m-tolyloxazol-4-ylmethoxy)cyclohexyloxy]-2-propoxypropan-1-ol as a colorless oil. The residue is purified by flash chromatography on silica gel (n-heptane/ethyl acetate =1:1). $C_{24}H_{35}NO_5$ (417.55), MS (ESI): 418 (M+H$^+$).

2R-(1R',3S')-2-(2-Propoxy)-3-[3-(5-methyl-2-m-tolyloxazol-4-ylmethoxy)-cyclohexyloxy]propionic acid

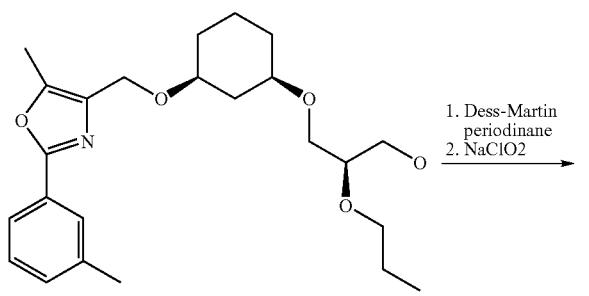

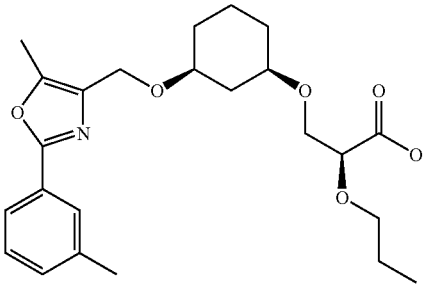

180 mg of Dess-Martin periodinane are added to 90 mg of 2R-(1R',3S')-2-propoxy-3-[3-(5-methyl-2-m-tolyloxazol-4-ylmethoxy)cyclohexyloxy]propan-1-ol in 1.5 ml of dichloromethane, and the mixture is stirred at room temperature for 2 h. 41 mg of $Na_2S_2O_3$ in 3 ml of a 5% strength $NaHCO_3$ solution are then added, and the mixture is stirred at room temperature for 10 min. The organic phase is separated off, dried over $MgSO_4$ and concentrated. The residue is taken up in 2 ml of acetonitrile, and 1.5 ml of a 0.65 M $NaH_2PO_4$ solution and 48 µl of 35% strength $H_2O_2$ solution are added. At 0° C., 30 mg of NaClO2 in 2 ml of water are added dropwise over a period of 1 h. The mixture is stirred at this temperature for 3 h. $Na_2SO_3$ solution, 10% HCl and 10 ml of $CH_2Cl_2$ are then added, the phases are separated and the organic phase is dried over $MgSO_4$ and concentrated.

Purification of the residue by HPLC gives 1.2 mg of 2R-(1R',3S')-2-(2-methyl-propoxy)-3-[3-(5-methyl-2-m-tolyloxazol-4-ylmethoxy)cyclohexyloxy]prop ionic acid.

EXAMPLE 11

2R-(1R',3S')-3-[3-(5-Methyl-2-m-tolyloxazol-4-ylmethoxy)cyclohexyloxy]-2-(4-trifluoromethylbenzyloxy)propanoic acid

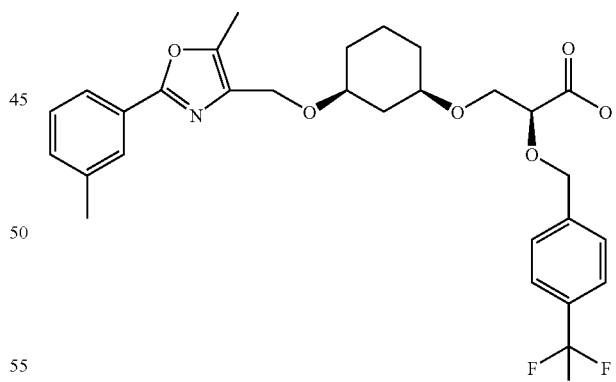

Analogously to Example 10, 2S-(1R',3S')-1-(tert-butyldimethylsilanyloxy)-3-[3-(5-methyl-2-m-tolyloxazol-4-ylmethoxy)cyclohexyloxy]propan-2-ol and 4-trifluoro-methylbenzyl bromide give 2R-(1R',3S')-3-[3-(5-methyl-2-m-tolyloxazol-4-yl-methoxy)cyclohexyloxy]-2-(4-trifluoromethylbenzyloxy)propionic acid.

EXAMPLE 12

3-[(1R,3S)-3-(5-Methyl-2-m-tolyloxazol4-ylmethoxy)cyclohexyloxy]-2-methoxypropionic acid

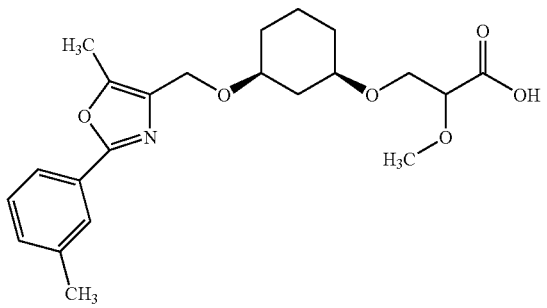

Analogously to Example 10, 1-(tert-butyldimethylsilanyloxy)-3-[(1R,3S)-3-(5-methyl-2-m-tolyloxazol-4-yl-methoxy)cyclohexyloxy]propan-2-ol and methyl iodide give 3-[(1R,3S)-3-(5-methyl-2-m-tolyloxazol-4-ylmethoxy)cyclohexyloxy]-2-methoxypropionic acid.

EXAMPLE 13

3-[(1R,3S)-3-(5-Methyl-2-m-tolyloxazol-4-ylmethoxy)cyclohexyloxy]-2-(4-trifluoro-methylbenzyloxy)propanoic acid

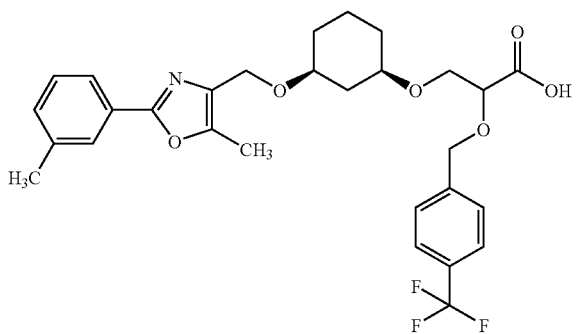

Analogously to Example 10, 1-(tert-butyidimethylsilanyloxy)-3-[(1R,3S)-3-(5-methyl-2-m-tolyloxazol-4-yl-methoxy)cyclohexyloxy]propan-2-ol and 4-trifluoro-methylbenzyl bromide give 3-[(1R,3S)-3-(5-methyl-2-m-tolyloxazol-4-ylmethoxy)-cyclohexyl 2-(4-trifluoromethylbenzyloxy)propanoic acid.

EXAMPLE 14

3-[(1R,3S)-3-(5-Methyl-2-m-tolyloxazol-4-ylmethoxy)cyclohexyloxy]-2-(3-trifluoro-methylbenzyloxy)propanoic acid

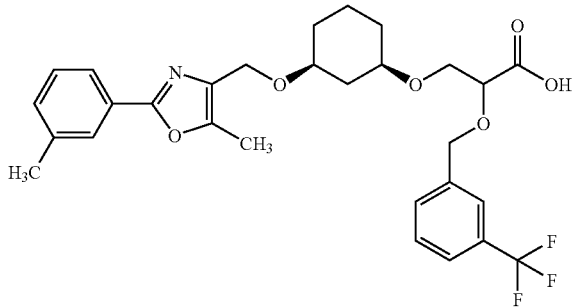

Analogously to Example 10, 1-(tert-butyldimethylsilanyloxy)-3-[(1R,3S)-3-(5-methyl-2-m-tolyloxazol-4-yl-methoxy)cyclohexyloxy]propan-2-ol and 3-trifluoro-methyl benzyl bromide give 3-[(1R,3S)-3-(5-methyl-2-m-tolyloxazol-4-ylmethoxy)-cyclohexyloxy]-2-(3-trifluoromethyl-benzyloxy)propanoic acid.

EXAMPLE 15

3-[(1R,3S)-3-(5-Methyl-2-m-tolyloxazol-4-ylmethoxy)cyclohexyloxy]-2-(3-methoxy-benzyloxy)propanoic acid

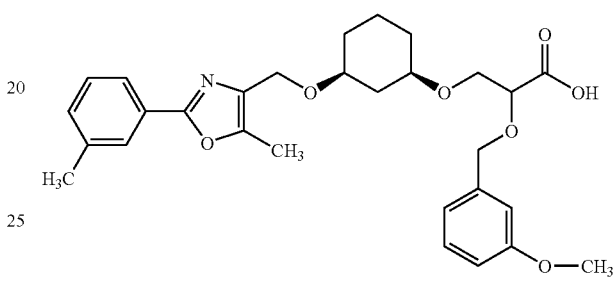

Analogously to Example 10, 1-(tert-butyldimethylsilanyloxy)-3-[(1R,3S)-3-(5-methyl-2-m-tolyloxazol-4-yl-methoxy)cyclohexyloxy]propan-2-ol and 3-methoxy-benzyl bromide give 3-[(1R,3S)-3-(5-methyl-2-m-tolyloxazol-4-yl-methoxy)cyclo-hexyloxy]-2-(3-methoxybenzyloxy)propanoic acid.

EXAMPLE 16

3-[(1R,3S)-3-(5-Methyl-2-m-tolyloxazol-4-ylmethoxy)cyclohexyloxy]-2-(2,5-dimethylbenzyloxy)propanoic acid

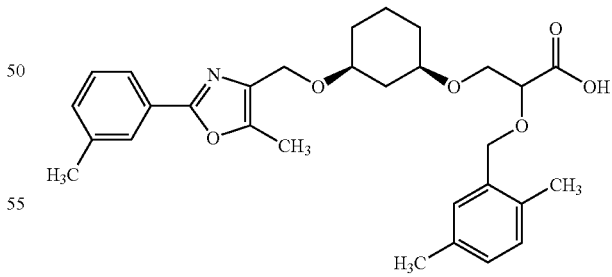

Analogously to Example 10, 1-(tert-butyldimethylsilanyloxy)-3-[(1R,3S)-3-(5-methyl-2-m-tolyloxazol-4-yl-methoxy)cyclohexyloxy]propan-2-ol and 2,5-dimethylbenzyl bromide give 3-[(1R,3S)-3-(5-methyl-2-m-tolyloxazol-4-yl-methoxy) cyclohexyloxy]-2-(2,5-dimethylbenzyloxy) propanoic acid.

EXAMPLE 17

3-[(1R,3S)-3-(5-Methyl-2-m-tolyloxazol-4-ylmethoxy)cyclohexyloxy]-2-(4-methyl-benzyloxy)propanoic acid

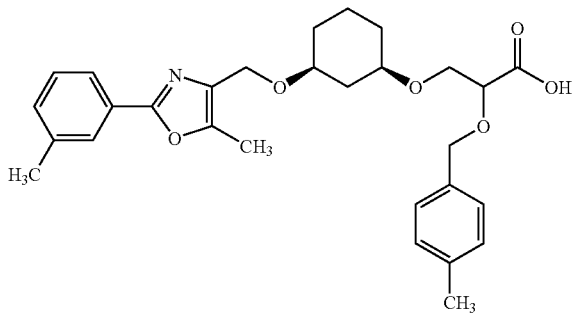

Analogously to Example 10, 1-(tert-butyldimethylsilanyloxy)-3-[(1R,3S)-3-(5-methyl-2-m-tolyloxazol-4-ylmethoxy)cyclohexyloxy]propan-2-ol and 4-methylbenzyl bromide give 3-[(1R,3S)-3-(5-methyl-2-m-tolyloxazol4-ylmethoxy)-cyclohexyloxy]-2-(4-methylbenzyloxy)propanoic acid.

EXAMPLE 18

3-[(1R,3S)-3-(5-Methyl-2-m-tolyloxazol-4-ylmethoxy)cyclohexyloxy]-2-(4-tert-butylbenzyloxy)propanoic acid

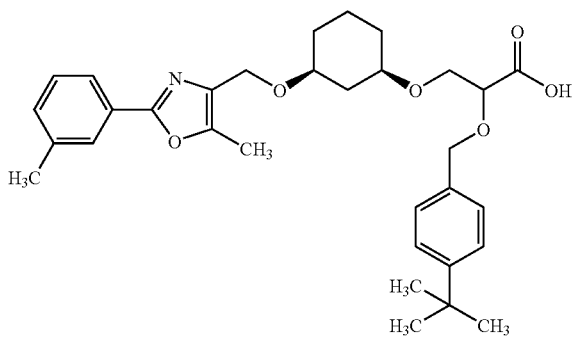

Analogously to Example 10, 1-(tert-butyldimethylsilanyloxy)-3-[(1R,3S)-3-(5-methyl-2-m-tolyloxazol-4-ylmethoxy)cyclohexyloxy]propan-2-ol and 4-tert-butylbenzyl bromide give 3-[(1R,3S)-3-(5-methyl-2-m-tolyloxazol-4-ylmethoxy)-cyclohexyloxy]-2-(4-tert-butylbenzyloxy)propanoic acid.

EXAMPLE 19

3-[(1R,3S)-3-(5-Methyl-2-m-tolyloxazol-4-ylmethoxy)cyclohexyloxy]-2-(2-trifluoromethylbenzyloxy)propanoic acid

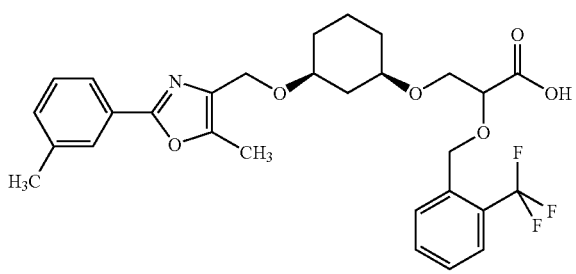

Analogously to Example 10, 1-(tert-butyldimethylsilanyloxy)-3-[(1R,3S)-3-(5-methyl-2-m-tolyloxazol-4-ylmethoxy)cyclohexyloxy]propan-2-ol and 2-trifluoro-methylbenzyl bromide give 3-[(1R,3S)-3-(5-methyl-2-m-tolyloxazol-4-ylmethoxy)-cyclohexyloxy]-2-(2-trifluoromethylbenzyloxy)propanoic acid.

EXAMPLE 20

3-[(1R,3S)-3-(5-Methyl-2-m-tolyloxazol-4-ylmethoxy)cyclohexyloxy]-2-(2-chlorothien-5-ylmethoxy)propionic acid

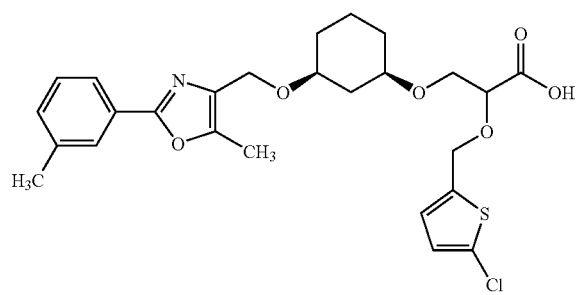

Analogously to Example 10, 1-(tert-butyldimethylsilanyloxy)-3-[(1R,3S)-3-(5-methyl-2-m-tolyloxazol-4-ylmethoxy)cyclohexyloxy]propan-2-ol and 2-chlorothien-5-ylmethyl chloride give 3-[(1R,3S)-3-(5-methyl-2-m-tolyloxazol-4-ylmethoxy)-cyclohexyloxy]-2-(2-chlorothien-5-ylmethoxy)propionic acid.

EXAMPLE 21

3-[(1R,3S)-3-(5-Methyl-2-m-tolyloxazol-4-ylmethoxy)cyclohexyloxy]-2-(2-butynyl-oxy)propionic acid

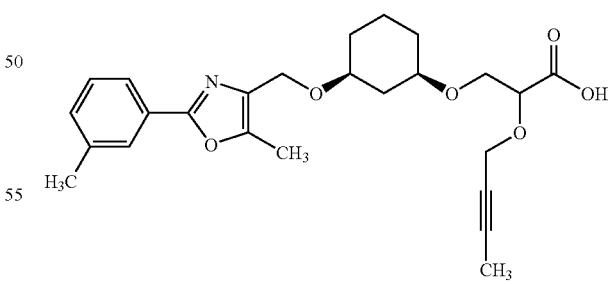

Analogously to Example 10, 1-(tert-butyldimethylsilanyloxy)-3-[(1R,3S)-3-(5-methyl-2-m-tolyloxazol4-ylmethoxy)cyclohexyloxy]propan-2-ol and 2-butynyl bromide give 3-[(1R,3S)-3-(5-methyl-2-m-tolyloxazol4-ylmethoxy)cyclohexyloxy]-2-(2-butynyloxy)propionic acid.

EXAMPLE 22

3-[(1R,3S)-3-(5-Methyl-2-m-tolyloxazol-4-ylmethoxy)cyclohexyloxy]-2-(2-propynyl-oxy)propionic acid

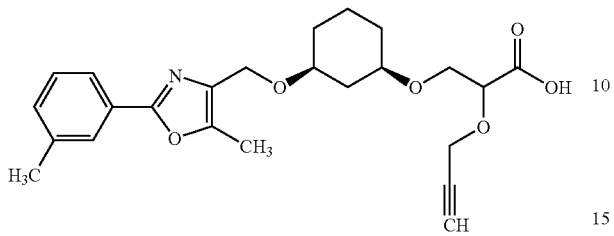

Analogously to Example 10, 1-(tert-butyidimethylsilanyloxy)-3-[(1R,3S)-3-(5-methyl-2-m-tolyloxazol4-ylmethoxy)cyclohexyloxy]propan-2-ol and 2-propynyl bromide give 3-[(1R,3S)-3-(5-methyl-2-m-tolyloxazol-4-ylmethoxy)cyclohexyloxy]-2-(2-propynyloxy)propionic acid.

EXAMPLE 23

3-[(1R,3S)-3-(5-Methyl-2-m-tolyloxazol4-ylmethoxy)cyclohexyloxy]-2-(2-pentynyl-oxy)propionic acid

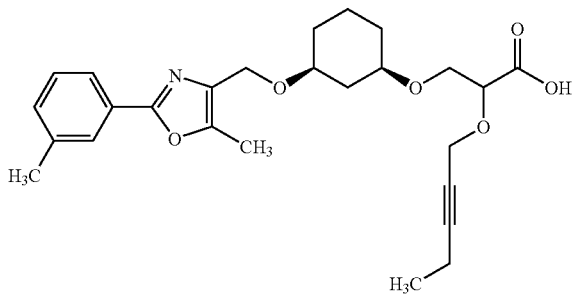

Analogously to Example 10, 1-(tert-butyldimethylsilanyloxy)-3-[(1R,3S)-3-(5-methyl-2-m-tolyloxazol-4-ylmethoxy)cyclohexyloxy]propan-2-ol and 2-pentynyl bromide give 3-[(1R,3S)-3-(5-methyl-2-m-tolyloxazol-4-ylmethoxy)cyclohexyloxy]-2-(2-pentynyloxy)propionic acid.

EXAMPLE 24

3-[(1R,3S)-3-(5-Methyl-2-m-tolyl-oxazol-4-ylmethoxy)cyclohexyloxy]-2-(2-propenyl-oxy)propionic acid

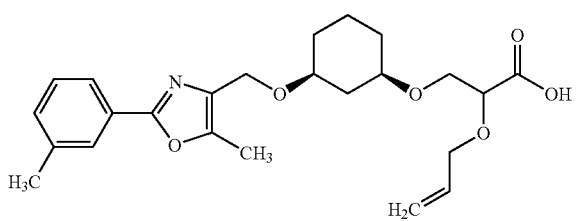

Analogously to Example 10, 1-(tert-butyidimethylsilanyloxy)-3-[(1R,3S)-3-(5-methyl-2-m-tolyloxazol-4-ylmethoxy)cyclohexyloxy]propan-2-ol and allyl bromide give 3-[(1R,3S)-3-(5-methyl-2-m-tolyloxazol-4-ylmethoxy)cyclohexyloxy]-2-(2-propenyloxy)propionic acid.

EXAMPLE 25

3-[(1R,3S)-3-(5-Methyl-2-m-tolyloxazol-4-ylmethoxy)cyclohexyloxy]-2-(3-phenyl-2-propenyloxy)propionic acid

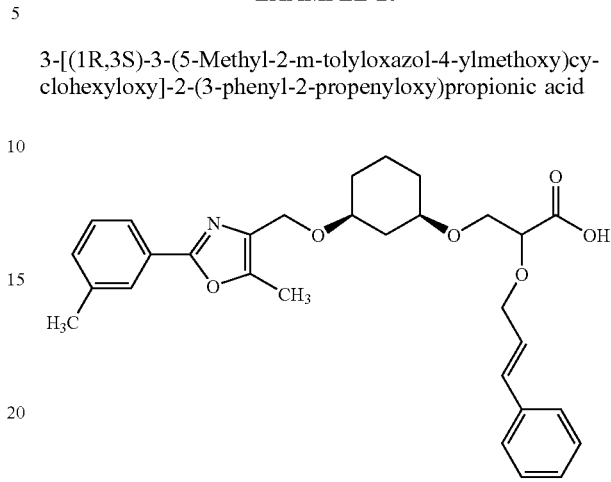

Analogously to Example 10, 1-(tert-butyldimethylsilanyloxy)-3-[(1R,3S)-3-(5-methyl-2-m-tolyloxazol-4-ylmethoxy)cyclohexyloxy]propan-2-ol and 3-phenyl-2-propenyl bromide give 3-[(1R,3S)-3-(5-methyl-2-m-toly-oxazol-4-ylmethoxy)cyclo-hexyloxy]-2-(3-phenyl-2-propenyloxy)propionic acid.

EXAMPLE 26

3-[(1R,3S)-3-(5-Methyl-2-m-tolyloxazol-4-ylmethoxy)cyclohexyloxy]-2-(2-methyl-2-propenyloxy)propionic acid

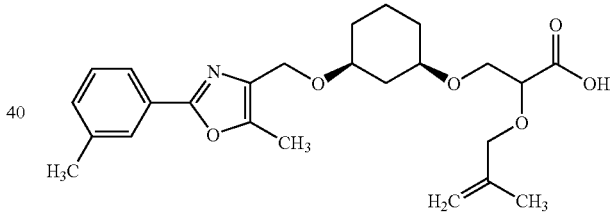

Analogously to Example 10, 1-(tert-butyldimethylsilanyloxy)-3-[(1R,3S)-3-(5-methyl-2-m-tolyloxazol-4-ylmethoxy)cyclohexyloxy]propan-2-ol and isobutenyl bromide give 3-[(1R,3S)-3-(5-methyl-2-m-tolyloxazol-4-ylmethoxy)cyclohexyloxy]-2-(2-methyl-2-propenoxy)propionic acid.

EXAMPLE 27

3-[(1R,3S)-3-(5-Methyl-2-m-tolyloxazol-4-ylmethoxy)cyclohexyloxy]-2-benzyloxy-propionic acid

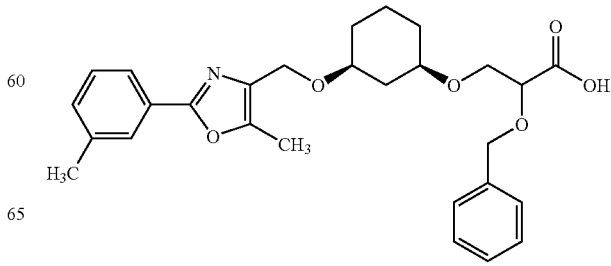

Analogously to Example 10, 1-(tert-butyidimethylsilanyloxy)-3-[(1R,3S)-3-(5-methyl-2-m-tolyloxazol-4-yl-methoxy)cyclohexyloxy]propan-2-ol and benzyl bromide give 3-[(1R,3S)-3-(5-methyl-2-m-tolyloxazol-4-ylmethoxy)cyclohexyloxy]-2-benzyloxypropionic acid.

EXAMPLE 28

Benzyl (1S,3R)-3-allyloxycyclohex-1-yl ether

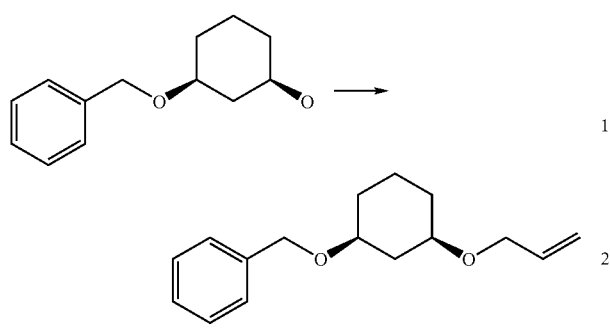

Under an atmosphere of argon, 12 g of sodium hydride (55-65%) are initially charged in 200 ml of abs. DMF, and the mixture is stirred at RT for 10 min. With ice-cooling, 54 g of benzyl (1S,3R)-3-hydroxycyclohex-1-yl ether in 70 ml of DMF are added dropwise. The mixture is stirred at RT for 90 min. With ice-cooling, 50 g of allyl bromide are slowly added dropwise. After the addition has ended, the mixture is stirred at 45° C. for 1 h. According to TLC, the reaction is complete. The reaction solution is quenched with 15 ml of iPrOH, diluted with water and sat. NaCl solution and extracted with MTBE. The combined organic phases are washed with water and NaCl solution, dried over MgSO4 and concentrated. This gives 60 g of benzyl (1S,3R)-3-allyloxycyclohex-1-yl ether as a light-beige oil. C16H22O2 (246.35), MS (ESI): 247 (M+H$^+$).

(1S,3R)-3-Allyloxycyclohex-1-yl benzoate

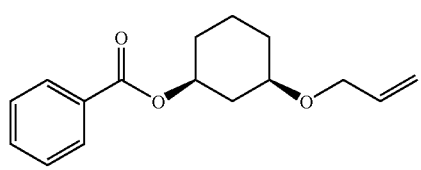

Analogously to benzyl (1S,3R)-3-allyloxycyclohex-1-yl ether, (1S,3R)-3-hydroxycyclohex-1-yl benzoate and allyl bromide give (1S,3R)-3-allyloxycyclohex-1-yl benzoate. C16H20O3 (260.37), MS (ESI): 261 (M+H$^+$).

Allyl (1R,3S)-3-trityloxymethylcyclohex-1-yl ether

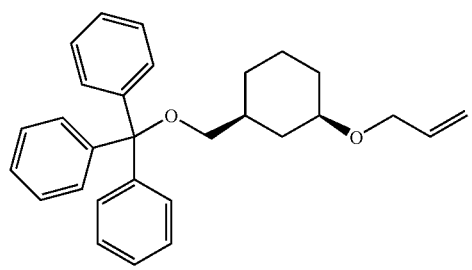

Analogously to benzyl (1S,3R)-3-allyloxycyclohex-1-yl ether, (1R,3S)-3-trityloxy-methylcyclohexanol and allyl bromide give allyl (1R,3S)-3-trityloxymethylcyclohex-1-yl ether.

(2R/2S)-3-[(1S,3R)-3-Benzyloxycyclohexyloxy]propane-1,2-diol

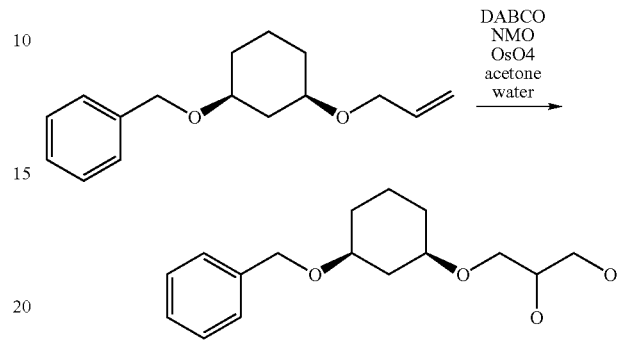

At 0° C., 6.8 g of DABCO, 42.8 g of NMO and 8.0 ml of an osmium tetroxide solution (2.5% in tert-butanol) are added successively to 60 g of benzyl (1S,3R)-3-allyloxycyclohex-1-yl ether in 200 ml of acetone/water (10:1). The solution is stirred at RT overnight. After 24 h, another 5 ml of osmium tetroxide solution are added, and the solution is stirred at RT overnight. The reaction is then complete. Sodium sulfite solution and water are added and the mixture is extracted with dichloromethane. The organic phase is dried over Na2SO4 and concentrated, giving 65 g of (2R/2S)-3-[(1S,3R)-3-benzyloxycyclohexyloxy]propane-1,2-diol as a brown oil. C16H24O4 (280.37), MS (ESI): 281 (M+H$^+$).

(2R/2S)-3-[(1R,3S)-1-Benzoyloxycyclohex-3-yloxy]propane-1,2-diol

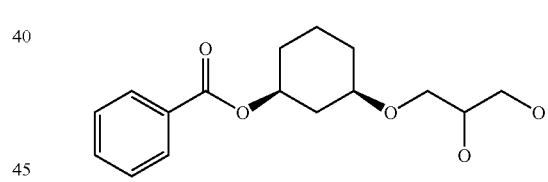

Analogously to (2R/2S)-3-[(1S,3R)-3-benzyloxycyclohexyloxy]propane-1,2-diol, (1S,3R)-3-hydoxycyclohex-1-yl benzoate, NMO, DABCO and osmium tetroxide give (2R/2S)-3-[(1R,3S)-1-benzoyloxycyclohex-3-yloxy]propane-1,2-diol.

C16H22O5 (294.35), MS (ESI): 295 (M+H$^+$).

(2R/2S)-3-[(1R,3S)-3-Trityloxymethylcyclohexyloxy]propane-1,2-diol

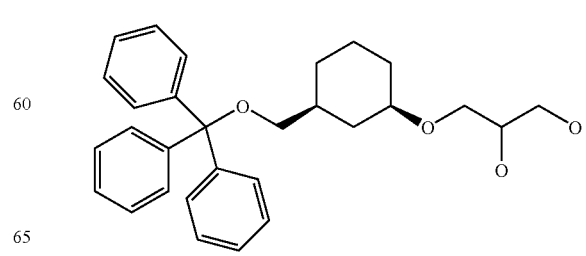

Analogously to (2R/2S)-3-[(1S,3R)-3-benzyloxycyclohexyloxy]propane-1,2-diol, allyl (1R,3S)-3-trityloxymethylcyclohex-1-yl ether, NMO, DABCO and osmium tetroxide give (2R/2S)-3-[(1R,3S)-3-trityloxymethylcyclohexyloxy]propane-1,2-diol.

(2R/2S)-3-[(1S,3R)-3-Benzyloxycyclohexyloxy]-2-hydroxypropyl tert-butyidiphenyl-silyl ether

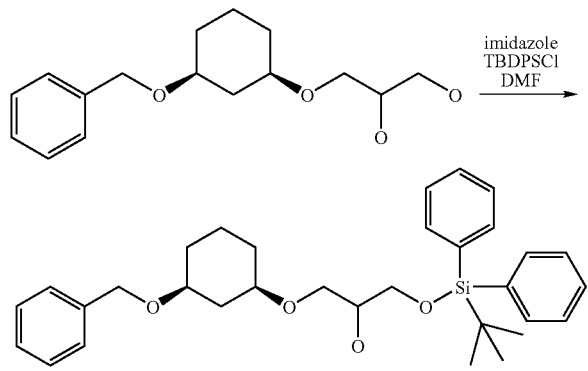

20 g of (2 R/2S)-3-[(1S ,3R)-3-benzyloxycyclohexyloxy] propane-1,2-diol are dissolved in 100 ml of DMF, and 12 g of imidazole and then 20.6 g of TBDPSCI are added and the mixture is stirred at RT. After 3 h, the reaction is complete. Dilution of the solution with water/sat. NaCl solution, extraction with MTBE and drying of the organic phase over MgSO4 and concentration give 35 g of (2R/2S)-3-[(1S,3R)-3-benzyloxycyclohexyloxy]-2-hydroxypropyl tert-butyldiphenylsilyl ether as a yellow oil. C32H42O4Si (518.78), MS (ESI): 519 (M+H⁺).

(2R/2S)-3-[(1R,3S)-1-Benzoyloxycyclohex-1-yloxy]-2-hydroxypropyl tert-butyldi-methylsilyl ether

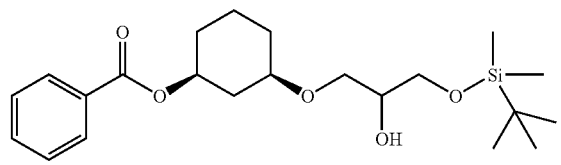

Analogously to (2R/2S)-3-[(1S,3R)-3-benzoyloxycyclohex-1-yloxy]-2-hydroxypropyl tert-butyldiphenylsilyl ether, (2R/2S)-3-[(1R,3S)-1-benzoyloxycyclohex-3-yloxy]-propane-1,2-diol, imidazole and TBDMSCI give (2R/2S)-3-[(1S,3R)-1-benzoyloxy-cyclohex-1-yloxy]-2-hydroxypropyl tert-butyldimethylsilyl ether. C22H36O5Si (408.62), MS (ESI): 409 (M+H⁺).

(2R/2S)-3-[(1R,3S)-3-Trityloxymethylcyclohexyloxy]-2-hydroxypropyl tert-butyidi-phenylsilyl ether

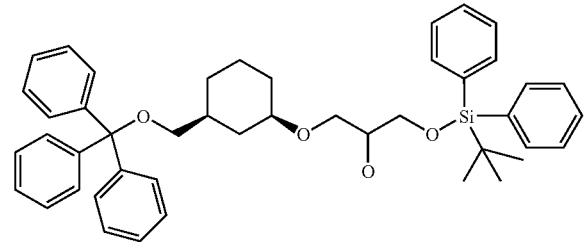

Analogously to (2 R/2S)-3-[(1S ,3R)-3-benzyloxycyclohexyloxy]-2-hydroxypropyl tert-butyldiphenylsilyl ether, (2R/2S)-3-[(1R,3S)-3-trityloxymethylcyclohexyloxy]-propane-1,2-diol, imidazole and TBDPSCI give (2R/2S)-3-[(1R,3S)-3-trityloxy-methylcyclohexyloxy]-2-hydroxypropyl tert-butyidiphenylsilyl ether.

(2R/2S)-3-[(1S,3R)-3-Benzyloxycyclohexyloxy]-2-methoxypropyl tert-butyldiphenyl-silyl ether

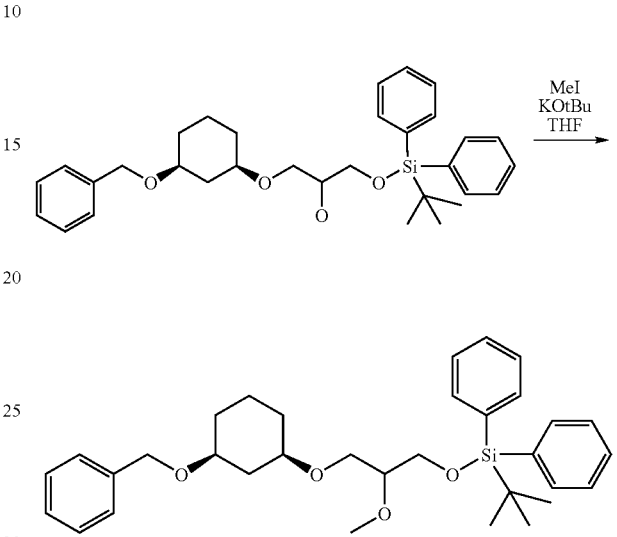

10 g of (2R/2S)-3-[(1S,3R)-3-benzyloxycyclohexyloxy]-2-hydroxypropyl tert-butyldi-phenylsilyl ether and 8.5 g of iodomethane are dissolved in 100 ml of THF. At RT, 3.3 g of KOtBu are added and the suspension is stirred at RT for 1 h. Sat. NH4Cl solution and water are then added, and the solution is extracted with MTBE. The combined organic phases are dried over MgSO4 and concentrated. The residue is chromatographed on silica gel (heptane/ethyl acetate 5:1→1:1), giving 7.2 g of (2R/2S)-3-[(1S,3R)-3-benzyloxycyclohexyloxy]-2-methoxypropyl tert-butyldiphenyl-silyl ether as a light-yellow oil.

(2R/2S)-3-[(1S,3R)-3-Benzyloxycyclohexyloxy]-2-ethoxypropyl tert-butyldiphenyl-silyl ether

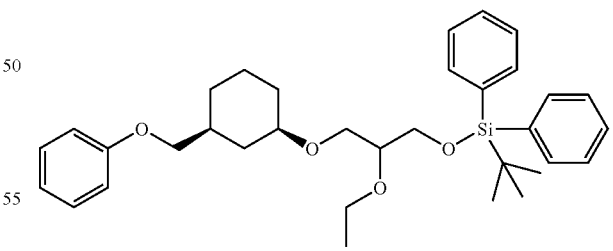

Analogously to (2 R/2S)-3-[(1S ,3R)-3-benzyloxycyclohexyloxy]-2-methoxypropyl tert-butyidiphenylsilyl ether, (2R/2S)-3-[(1S,3R)-3-benzyloxycyclohexyloxy]-2-hydroxypropyl tert-butyldiphenylsilyl ether and iodoethane give (2R/2S)-3-[(1S,3R)-3-benzyloxycyclohexyloxy]-2-ethoxypropyl tert-butyldiphenylsilyl ether.

(2R/2S)-3-[(1S,3R)-3-Benzyloxycyclohexyloxy]-2-allyloxypropyl tert-butyldiphenyl-silyl ether

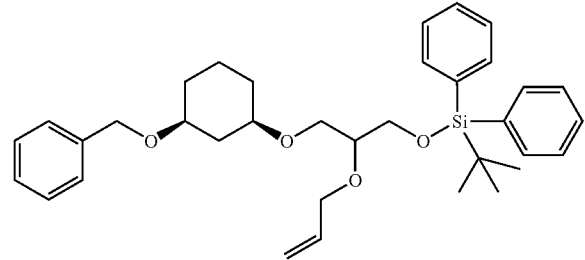

Analogously to (2R/2S)-3-[(1S,3R)-3-benzyloxycyclohexyloxy]-2-methoxypropyl tert-butyldiphenylsilyl ether, (2R/2S)-3-[(1S,3R)-3-benzyloxycyclohexyloxy]-2-hydroxypropyl tert-butyldiphenylsilyl ether and allyl bromide give (2R/2S)-3-[(1S,3R)-3-benzyloxycyclohexyloxy]-2-allyloxypropyl tert-butyldiphenylsilyl ether.

(2R/2S)-3-[(1S,3R)-3-Benzyloxycyclohexyloxy]-2-(2-methyl-2-propenyloxy)propyl tert-butyldiphenylsilyl ether

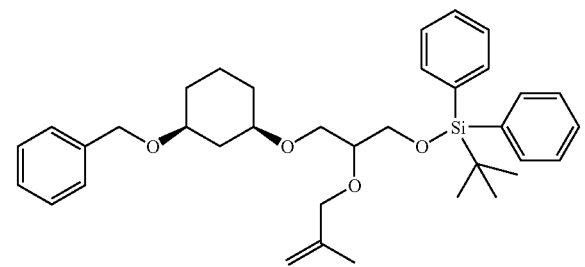

Analogously to (2R/2S)-3-[(1S ,3R)-3-benzyloxycyclohexyloxy]-2-methoxypropyl tert-butyldiphenylsilyl ether, (2R/2S)-3-[(1S,3R)-3-benzyloxycyclohexyloxy]-2-hydroxypropyl tert-butyldiphenylsilyl ether and isobutenyl bromide give (2R/2S)-3-[(1S,3R)-3-benzyloxycyclohexyloxy]-2-(2-methyl-2-propenyloxy)propyl tert-butyldi-phenylsilyl ether.

(2R/2S)-3-[(1R,3S)-3-Benzoyloxycyclohex-1-yloxy]-2-(4-trifluoromethylbenzyloxy)-propyl tert-butyidimethylsilyl ether

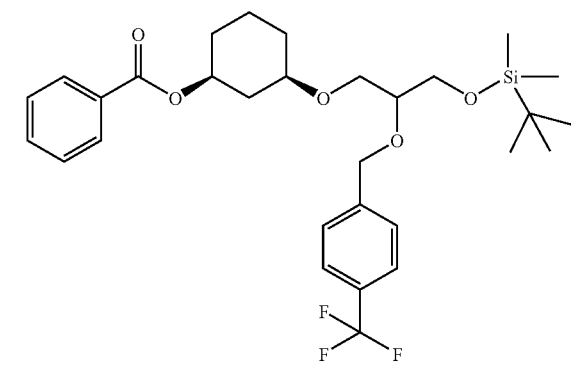

Analogously to (2R/2S)-3-[(1S,3R)-3-benzoyloxycyclohex-1-yloxy]-2-(4-trifluoro-methylbenzyloxy)propyl tert-butyldimethylsilyl ether, (2R/2S)-3-[(1R,3S)-1-benzoyloxycyclohex-3-yloxy]-2-hydroxypropyl tert-butyidiphenylsilyl ether and 4-trifluoromethylbenzyl bromide give (2R/2S)-3-[(1R,3S)-3-benzoyloxycyclohex-1-yloxy]-2-(4-trifluoromethylbenzyloxy)propyl tert-butyidimethylsilyl ether.

(2R/2S)-3-[(1R,3S)-3-Trityloxymethylcyclohexyloxy]-2-(4-trifluoromethylbenzyloxy)-propyl tert-butyldiphenylsilyl ether

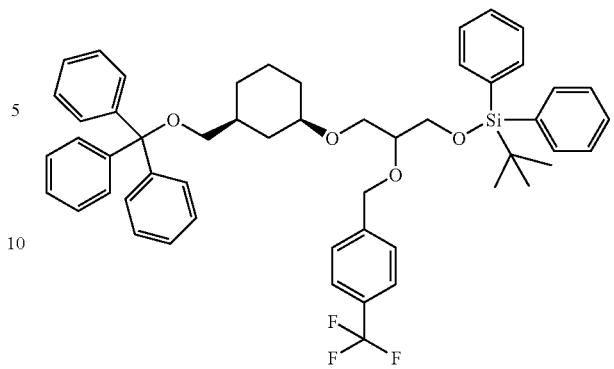

Analogously to (2R/2S)-3-[(1S,3R)-3-benzyloxycyclohexyloxy]-2-methoxypropyl tert-butyldiphenylsilyl ether, (2R/2S)-3-[(1R,3S)-3-trityloxymethylcyclohexyloxy]-2-hydroxypropyl tert-butyidiphenylsilyl ether and 4-trifluoromethylbenzyl bromide give (2R/2S)-3-[(1R,3S)-3-trityloxymethylcyclohexyloxy]-2-(4-trifluoromethylbenzyloxy)-propyl tert-butyldiphenylsilyl ether.

(2R/2S)-3-[(1S,3R)-3-Hydroxycyclohexyloxy]-2-methoxypropyl tert-butyldiphenyl-silyl ether

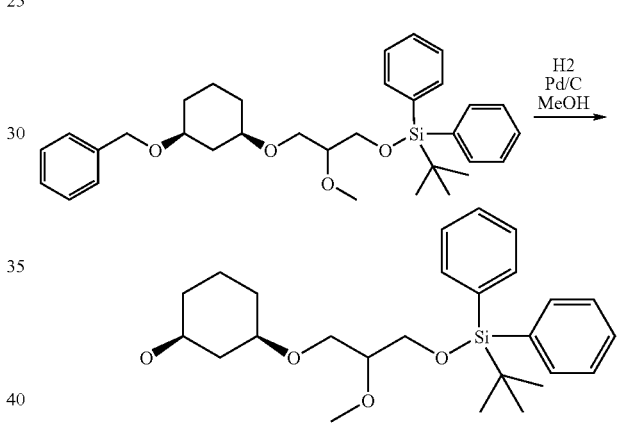

7.2 g of (2R/2S)-3-[(1S,3R)-3-benzyloxycyclohexyloxy]-2-methoxypropyl tert-butyl-diphenylsilyl ether are dissolved in 40 ml of methanol, 4 g of Pd/C (10%) are added and the mixture is hydrogenated at RT and a pressure of 5 bar for 15 h. The catalyst is filtered off, the residue is washed with dichloromethane and the filtrate is concentrated, giving 6.0 g of (2R/2S)-3-[(1S,3R)-3-hydroxycyclohexyloxy]-2-methoxypropyl tert-butyldiphenylsilyl ether as a colorless oil. C26H38O4Si (442.68), MS (ESI): 443 (M+H$^+$).

(2R/2S)-3-[(1S,3R)-3-Hydroxycyclohexyloxy]-2-ethoxypropyl tert-butyldiphenylsilyl ether

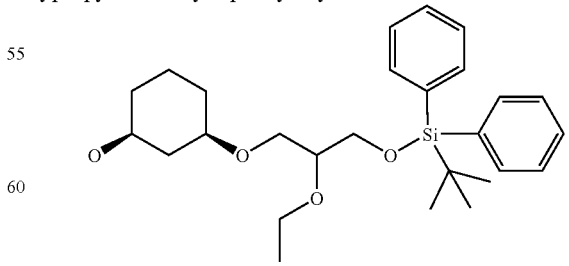

Analogously to (2R/2S)-3-[(1S,3R)-3-hydroxycyclohexyloxy]-2-methoxypropyl tert-butyldiphenylsilyl ether, (2R/2S)-3-[(1S,3R)-3-benzyloxycyclohexyloxy]-2-ethoxypropyl tert-butyldiphenylsilyl ether gives (2R/2S)-3-[(1S,-

3R)-3-hydroxycyclohexyl-oxy]-2-ethoxypropyl tert-butyldiphenylsilyl ether.

C27H40O4Si (456,70), MS (ESI): 457 (M+H$^+$).

(2R/2S)-3-[(1R,3S)-3-Hydroxymethylcyclohexyloxy]-2-(4-trifluoromethylbenzyloxy)-propyl tert-butyldiphenylsilyl ether

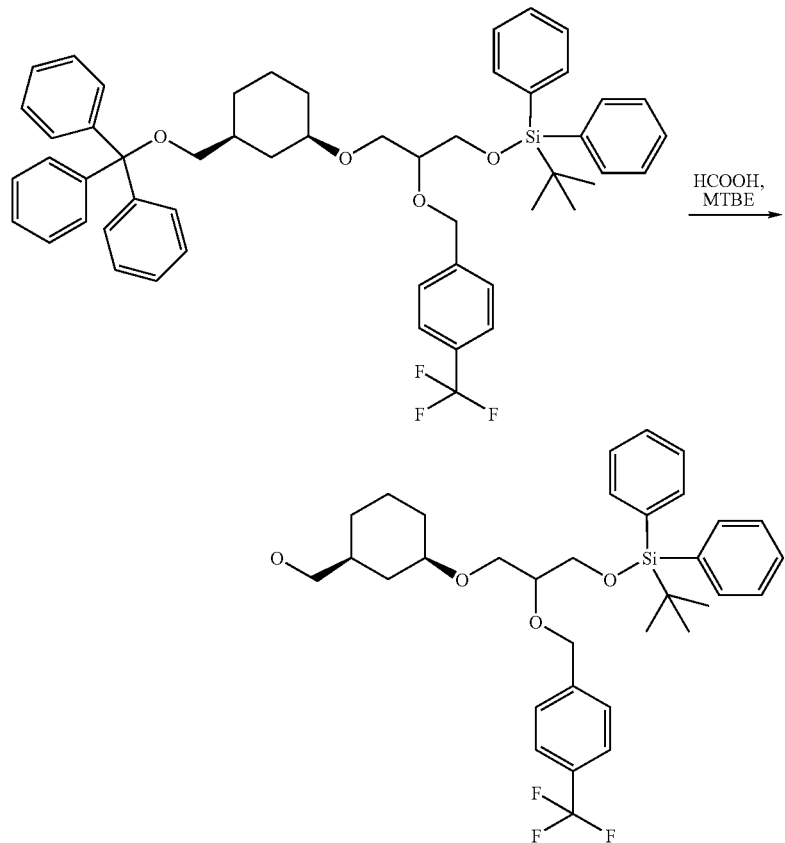

3.5 g of (2R/2S)-3-[(1R,3S)-3-trityloxymethylcyclohexyloxy]-2-(4-trifluoromethyl-benzyloxy) propyl tert-butyldiphenylsilyl ether are dissolved in 100 ml of MTBE, 58 g of formic acid are added and the mixture is stirred at RT. The solution is concentrated and the residue is chromatographed on silica gel, giving 170 mg of (2R/2S)-3-[(1R,3S)-3-hydroxymethylcyclohexyloxy]-2-(4-trifluoromethylbenzyloxy)-propyl tert-butyldiphenylsilyl ether as a colorless oil.

(2R/2S)-3-[(1S,3R)-3-Hydroxycyclohexyloxy]-2-propoxypropyl tert-butyldiphenyl-silyl ether Analogously to (2R/2S)-3-[(1S,3R)-3-hydroxycyclohexyloxy]-2-methoxypropyl tert-butyldiphenylsilyl ether, (2R/2S)-3-[(1S,3R)-3-benzyloxycyclohexyloxy]-2-propoxy-propyl tert-butyldiphenylsilyl ether gives (2R/2S)-3-[(1S,3R)-3-hydroxycyclohexyl-oxy]-2-propoxypropyl tert-butyldiphenylsilyl ether.

C28H42O4Si (470.73), MS (ESI): 471 (M+H$^+$).

(2R/2S)-3-[(1S,3R)-3-Hydroxycyclohexyloxy]-2-isobutoxypropyl tert-butyldiphenyl-silyl ether

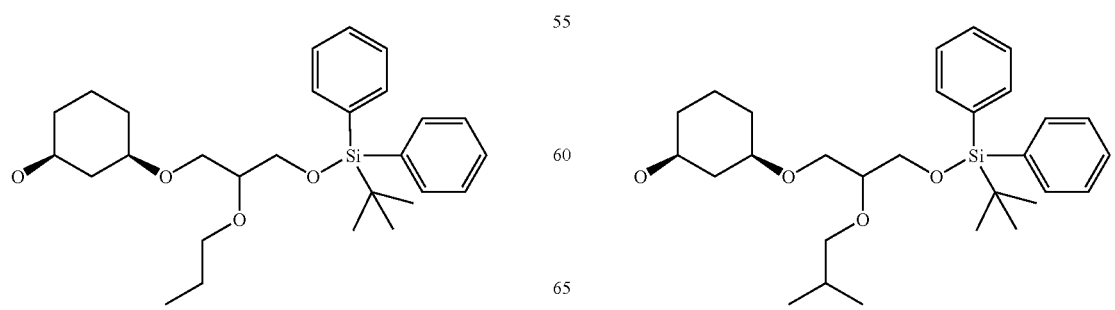

Analogously to (2R/2S)-3-[(1S,3R)-3-hydroxycyclohexyloxy]-2-methoxypropyl tert-butyldiphenylsilyl ether, (2R/2S)-3-[(1S,3R)-3-benzyloxycyclohexyloxy]-2-iso-butoxypropyl tert-butyldiphenylsilyl ether gives (2R/2S)-3-[(1S,3R)-3-hydroxycyclo-hexyloxy]-2-isobutoxypropyl tert-butyldiphenylsilyl ether.

C29H44O4Si (484.76), MS (ESI): 485 (M+H$^+$).

(2R/2S)-3-[(1R,3S)-1-Hydroxycyclohex-1-yloxy]-2-(4-trifluoromethylbenzyloxy) tert-butyldimethylsilyl ether

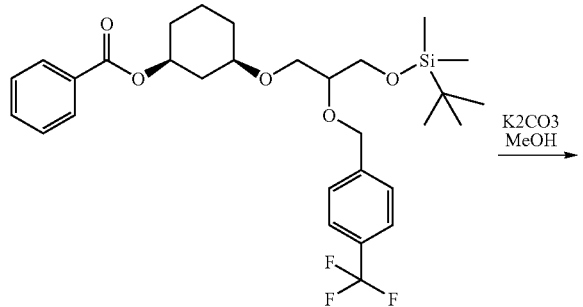

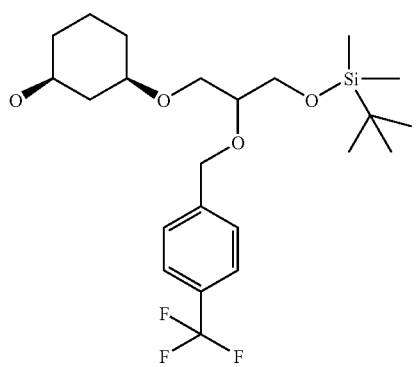

4.6 g of (2R/2S)-3-[(1S,3R)-1-benzoyloxycyclohex-3-yloxy]-2-(4-trifluoromethoxy-benzyloxy) tert-butyldimethylsilyl ether are dissolved in 20 ml of methanol, 2.2 g of K2CO3 are added and the mixture is stirred at RT for 72 h. The K2CO3 is filtered off, the residue is washed with methanol and the filtrate is concentrated, giving 0.85 g of (2R/2S)-3-[(1R,3S)-3-hydroxycyclohexyloxy]-2-(4-trifluoromethylbenzyl-oxy) tert-butyldimethylsilyl ether as a colorless oil. C23H37F3O4Si (462.63), MS (ESI): 463 (M+H$^+$).

2-Methoxy-3-[(1R,3S)-3-(5-methyl-2-phenyloxazol-4-ylmethoxy)cyclohexyloxy]-propanoic acid

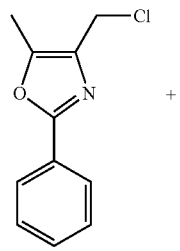 +

-continued

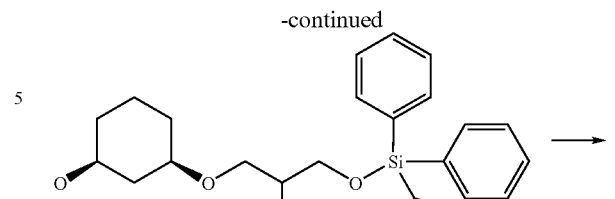

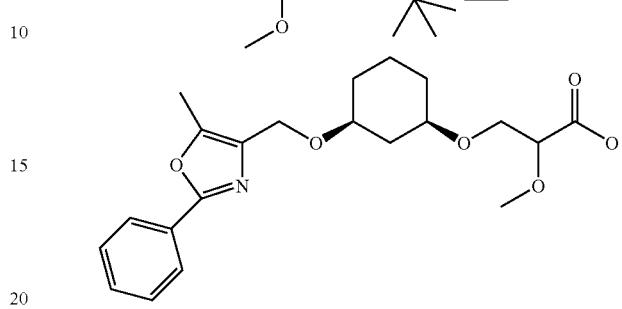

100 mg of (2R/2S)-3-[(1S,3R)-3-hydroxycyclohexyloxy]-2-methoxypropyl tert-butyl-diphenylsilyl ether are dissolved in 2 ml of THF, and 83 mg of 2-phenyl-5-methyloxazol-4-ylmethyl chloride and 51 mg of KOtBu are added successively.

The reaction mixture is shaken at RT overnight. 214 mg of TBAF are added, and the suspension is allowed to stand overnight. Water and MBTE are added and the organic phase is then separated off and concentrated. The residue is taken up in acetone, and 1 ml of 1.92 M Jones reagent are added. The reaction solution is shaken overnight. The solution is diluted with 3 ml of water and poured onto an extraction cartridge (kieselguhr, for 20 ml of aqueous phases). The cartridge is then eluted with ethyl acetate and the resulting solution is concentrated and purified by HPLC. This gives 5 mg of 2-methoxy-3-[(1R,3S)-3-(5-methyl-2-phenyl-oxazol-4-ylmethoxy)cyclohexyloxy]propionic acid as a yellow oil.

EXAMPLE 29

2-Methoxy-3-{(1R,3S)-3-[5-methyl-2-(3-trifluoromethylphenyl)oxazol-4-ylmethoxy]-cyclohexyloxy}propionic acid

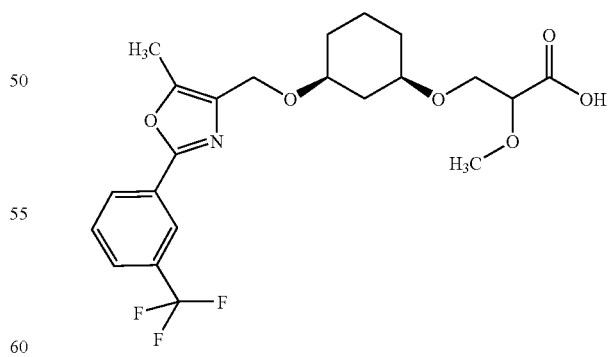

Analogously to Example 28, (2R/2S)-3-[(1S,3R)-3-hydroxycyclohexyloxy]-2-methoxypropyl tert-butyldiphenylsilyl ether and 5-methyl-2-(3-trifluoromethyl-phenyl)oxazol-4-ylmethyl iodide give 2-methoxy-3-{(1R,3S)-3-[5-methyl-2-(3-tri-fluoromethylphenyl)oxazol-4-ylmethoxy]cyclohexyloxy}propionic acid.

EXAMPLE 30
2-Methoxy-3-{(1R,3S)-3-[5-methyl-2-(3-trifluoromethoxyphenyl)oxazol4-yl-methoxy]cyclohexyloxy}propionic acid

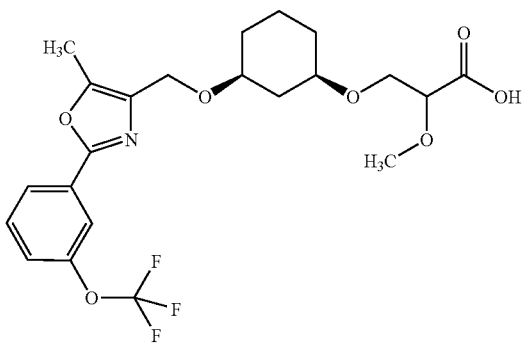

Analogously to Example 28, (2R/2S)-3-[(1S,3R)-3-hydroxycyclohexyloxy]-2-methoxypropyl tert-butyidiphenylsilyl ether and 5-methyl-2-(3-trifluoromethoxy-phenyl)oxazol-4-ylmethyl iodide give 2-methoxy-3-{(1R,3S)-3-[5-methyl-2-(3-trifluoromethoxyphenyl)oxazol4-ylmethoxy]cyclohexyloxy}propionic acid.

EXAMPLE 31
2-Methoxy-3-{(1R,3S)-3-[5-methyl-2-(4-trifluoromethylphenyl)oxazol-4-ylmethoxy]-cyclohexyloxy}propionic acid

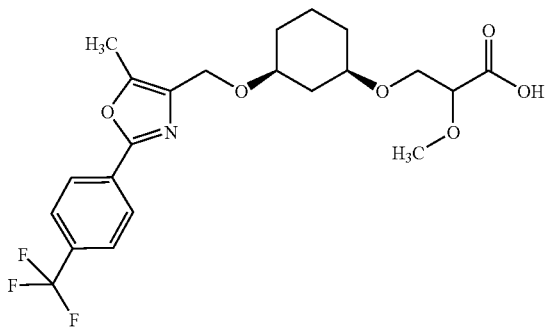

Analogously to Example 28, (2R/2S)-3-[(1S,3R)-3-hydroxycyclohexyloxy]-2-methoxypropyl tert-butyldiphenylsilyl ether and 5-methyl-2-(4-trifluoromethyl-phenyl)oxazol-4-ylmethyl iodide give 2-methoxy-3-{(1R,3S)-3-[5-methyl-2-(4-tri-fluoromethylphenyl)oxazol-4-ylmethoxy]cyclohexyloxy}propionic acid.

EXAMPLE 32
2-Methoxy-3-{(1R,3S)-3-[5-methyl-2-(4-methylphenyl)oxazol-4-ylmethoxy]cyclo-hexyloxy}propionic acid

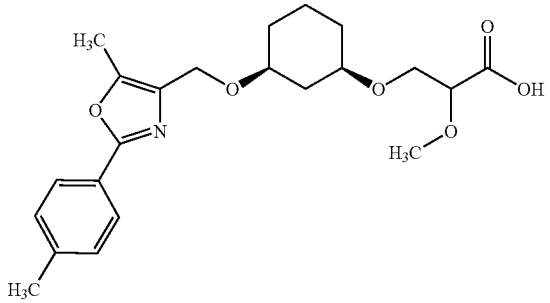

Analogously to Example 28, (2R/2S)-3-[(1S,3R)-3-hydroxycyclohexyloxy]-2-methoxypropyl tert-butyldiphenylsilyl ether and 5-methyl-2-(4-methylphenyl)oxazol-4-ylmethyl iodide give 2-methoxy-3-{(1R,3S)-3-[5-methyl-2-(4-methylphenyl)-oxazol-4-ylmethoxy]cyclohexyloxy}propionic acid

EXMPLE 33

2-Methoxy-3-{(1R,3S)-3-[5-methyl-2-(2,6-dimethylphenyl)oxazol-4-ylmethoxy]-cyclohexyloxy}propionic acid

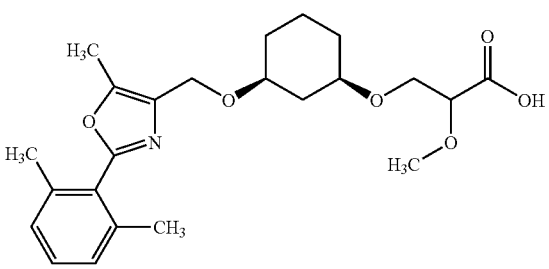

Analogously to Example 28, (2R/2S)-3-[(1S,3R)-3-hydroxycyclohexyloxy]-2-methoxypropyl tert-butyldiphenylsilyl ether and 5-methyl-2-(2,6-dimethylphenyl)-oxazol-4-ylmethyl iodide give 2-methoxy-3-{(1R,3S)-3-[5-methyl-2-(2,6-dimethyl-phenyl) oxazol-4-ylmethoxy] cyclohexyloxy}propionic acid.

EXAMPLE 34

2-Methoxy-3-{(1R,3S)-3-[5-methyl-2-(2-trifluoromethylphenyl)oxazol-4-ylmethoxy]-cyclohexyloxy}propionic acid

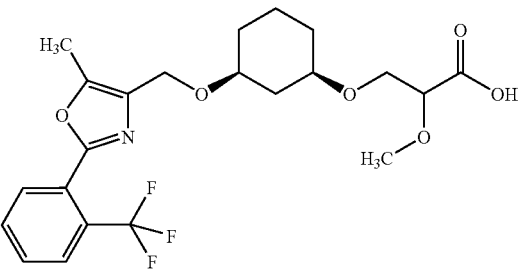

Analogously to Example 28, (2R/2S)-3-[(1S,3R)-3-hydroxycyclohexyloxy]-2-methoxypropyl tert-butyld iphenylsilyl ether and 5-methyl-2-(2-trifluoromethyl-phenyl)oxazol-4-ylmethyl iodide give 2-methoxy-3-{(1R,3S)-3-[5-methyl-2-(2-tri-fluoromethylphenyl)oxazol-4-ylmethoxy] cyclohexyloxy}propionic acid.

EXAMPLE 35

2-Methoxy-3-{(1R,3S)-3-[5-methyl-2-(3-naphthyl)oxazol-4-ylmethoxy]cyclohexyl-oxy}propionic acid

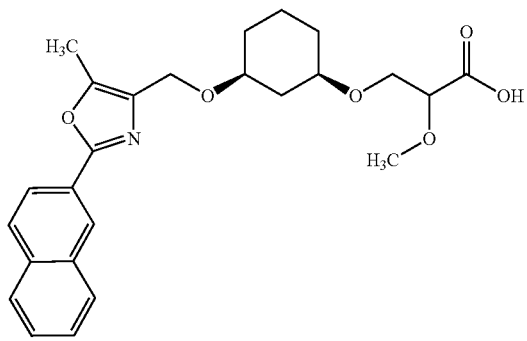

Analogously to Example 28, (2R/2S)-3-[(1S,3R)-3-hydroxycyclohexyloxy]-2-methoxypropyl tert-butyldiphenylsilyl ether and 5-methyl-2-(2-naphthyl)oxazol-4-yl-methyl iodide give 2-methoxy-3-{(1R,3S)-3-[5-methyl-2-(3-naphthyl)oxazol-4-yl-methoxy]cyclohexyloxy}propionic acid.

EXAMPLE 36

2-Methoxy-3-{(1R,3S)-3-[5-methyl-2-(2,4-dimethylphenyl)oxazol-4-ylmethoxy]-cyclohexyloxy}propionic acid

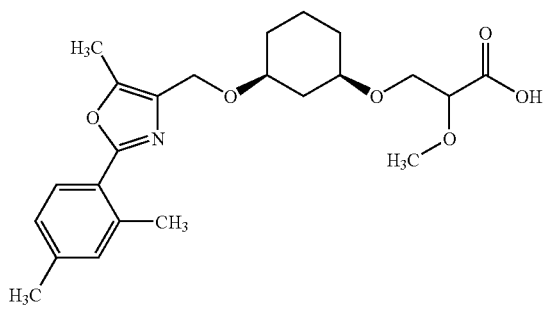

Analogously to Example 28, (2R/2S)-3-[(1S,3R)-3-hydroxycyclohexyloxy]-2-methoxypropyl tert-butyld iphenylsilyl ether and 5-methyl-2-(2,4-d imethylphenyl)-oxazol-4-ylmethyl iodide give 2-methoxy-3-{(1R,3S)-3-[5-methyl-2-(2,4-dimethyl-phenyl)oxazol-4-ylmethoxy]cyclohexyloxy}propionic acid.

EXAMPLE 37

2-Methoxy-3-{(1R,3S)-3-[5-methyl-2-(4-biphenyl)oxazol-4-ylmethoxy]-cyclohexyl-oxy}propionic acid

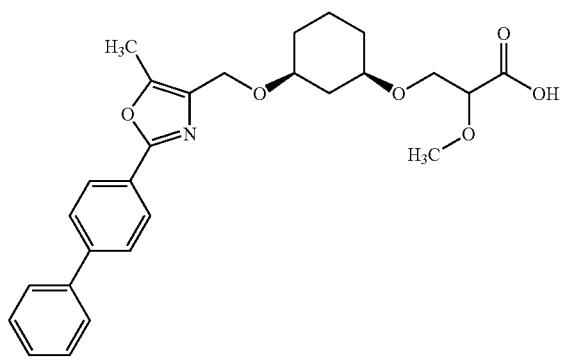

Analogously to Example 28, (2R/2S)-3-[(1S,3R)-3-hydroxycyclohexyloxy]-2-methoxypropyl tert-butyldiphenylsilyl ether and 5-methyl-2-(4-biphenyl)oxazol-4-yl-methyl iodide give 2-methoxy-3-{(1R,3S)-3-[5-methyl-2-(4-biphenyl)oxazol4-yl-methoxy]cyclohexyloxy}propionic acid.

EXAMPLE 38

2-Methoxy-3-{(1R,3S)-3-[5-ethyl-2-(3-methoxyphenyl)oxazol4-ylmethoxy]-cyclo-hexyloxy}propionic acid

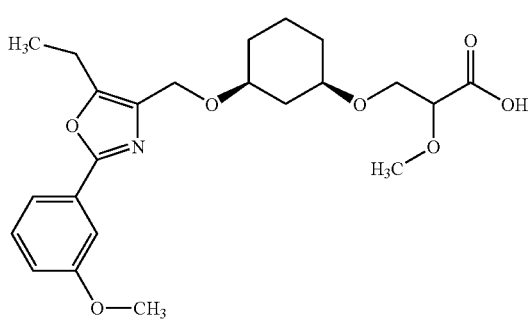

Analogously to Example 28, (2R/2S)-3-[(1S,3R)-3-hydroxycyclohexyloxy]-2-methoxypropyl tert-butyldiphenylsilyl ether and 5-ethyl-2-(3-methoxyphenyl)oxazol-4-ylmethyl iodide give 2-methoxy-3-{(1R,3S)-3-[5-ethyl-2-(3-methoxyphenyl)-oxazol-4-ylmethoxy] cyclohexyloxy}propionic acid.

EXAMPLE 39

2-Methoxy-3-{(1R,3S)-3-[5-ethyl-2-(4-methylphenyl)oxazol-4-ylmethoxy]cyclo-hexyloxy}propionic acid

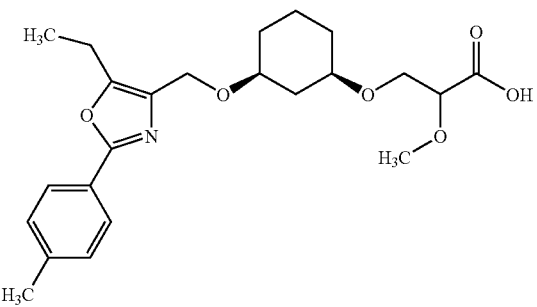

Analogously to Example 28, (2R/2S)-3-[(1S,3R)-3-hydroxycyclohexyloxy]-2-methoxypropyl tert-butyldiphenylsilyl ether and 5-ethyl-2-(4-methylphenyl)oxazol-4-ylmethyl iodide give 2-methoxy-3-{(1R,3S)-3-[5-ethyl-2-(4-methylphenyl)oxazol-4-ylmethoxy] cyclohexyloxy}propionic acid.

EXAMPLE 40

2-Methoxy-3-{(1R,3S)-3-[5-ethyl-2-(2-trifluoromethylphenyl)oxazol4-ylmethoxy ]-cyclohexyloxy}propionic acid

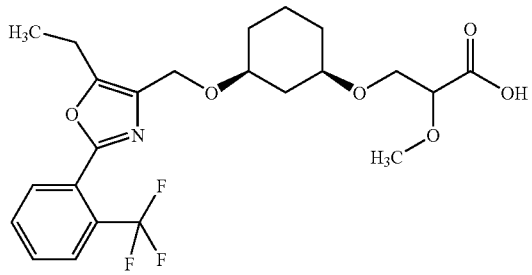

Analogously to Example 28, (2R/2S)-3-[(1S,3R)-3-hydroxycyclohexyloxy ]-2-methoxypropyl tert-butyldiphenylsilyl ether and 5-ethyl-2-(2-trifluoromethylphenyl)-oxazol 4-ylmethyl iodide give 2-methoxy-3-{(1R,3S)-3-[5-ethyl-2-(2-trifluoromethyl-phenyl) oxazol-4-ylmethoxy] cyclohexyloxy}propionic acid.

EXAMPLE 41

2-Methoxy-3-{(1R,3S)-3-[5-ethyl-2-(2,6-dimethylphenyl) oxazol4-ylmethoxy]cyclo-hexyloxy}propionic acid

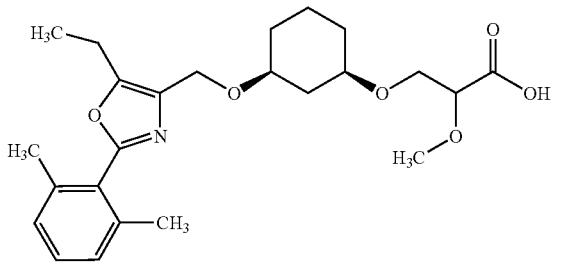

Analogously to Example 28, (2R/2S)-3-[(1S,3R)-3-hydroxycyclohexyloxy ]-2-methoxypropyl tert-butyldiphenylsilyl ether and 5-ethyl-2-(2,6-methylphenyl)oxazol-4-ylmethyl iodide give 2-methoxy-3-{(1R,3S)-3-[5-ethyl-2-(2,6-dimethylphenyl)-oxazol-4-ylmethoxy] cyclohexyloxy}propionic acid.

EXAMPLE 42

3-[(1R,3S)-3-(5-Methyl-2-phenyloxazol-4-ylmethoxy)cyclohexyloxy ]-2-propoxy-propionic acid

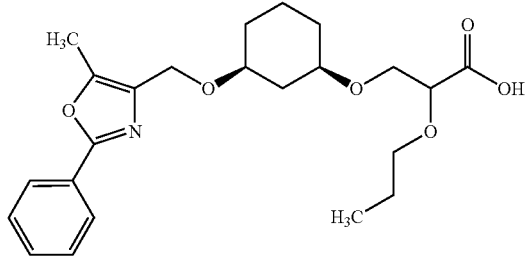

Analogously to Example 28, (2R/2S)-3-[(1S,3R)-3-hydroxycyclohexyloxy ]-2-propoxypropyl tert-butyldiphenylsilyl ether and 5-methyl-2-phenyloxazol-4-ylmethyl iodide give 3-[(1R,3S)-3-(5-methyl-2-phenyloxazol-4-ylmethoxy) cyclohexyloxy ]-2-propoxypropionic acid.

EXAMPLE 43

3-[(1R,3S)-3-(5-Methyl-2-(3-tolyl)oxazol-4-ylmethoxy)cyclohexyloxy]-2-propoxy-propionic acid

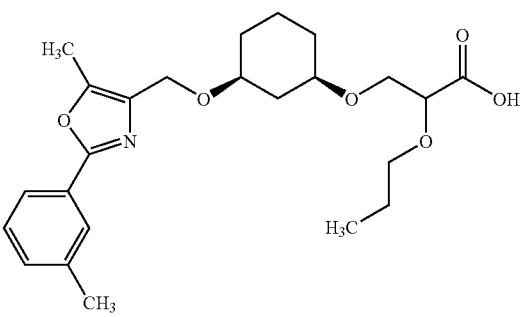

Analogously to Example 28, (2R/2S)-3-[(1S,3R)-3-hydroxycyclohexyloxy]-2-propoxypropyl tert-butyldiphenylsilyl ether and 5-methyl-2-(3-tolyl)oxazol-4-yl-methyl iodide give 3-[(1R,3S)-3-(5-methyl-2-(3-tolyl)oxazol-4-ylmethoxy)cyclo-hexyloxy]-2-propoxypropionic acid.

EXAMPLE 44

3-{(1R,3S)-3-[5-Methyl-2-(3-trifluoromethoxyphenyl)oxazol-4-ylmethoxy]cyclo-hexyloxy}-2-propoxypropionic acid

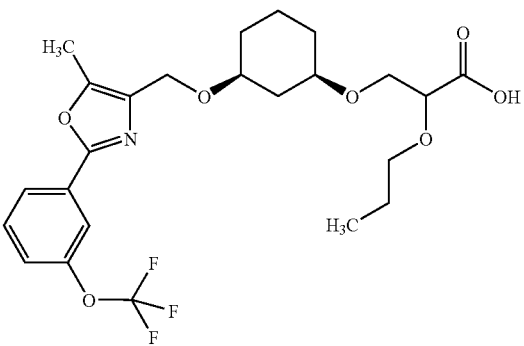

Analogously to Example 28, (2R/2S)-3-[(1S,3R)-3-hydroxycyclohexyloxy]-2-propoxypropyl tert-butyidiphenylsilyl ether and 2-(3-trifluoromethoxyphenyl)oxazol-4-ylmethyl iodide give 3-{(1R,3S)-3-[5-methyl-2-(3-trifluoromethoxyphenyl )oxazol-4-ylmethoxy] cyclohexyloxy}-2-propoxypropionic acid.

EXAMPLE 45

3-{(1R,3S)-3-[5-Methyl-2-(3-methoxyphenyl)oxazol-4-yl-methoxy]cyclohexyloxy}-2-propoxypropionic acid

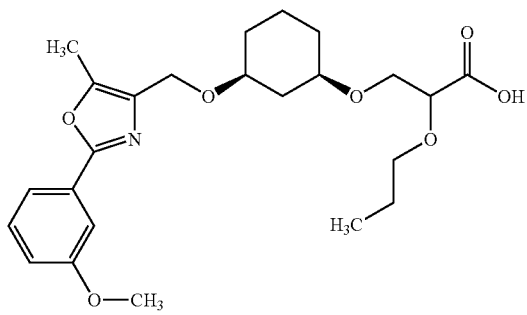

Analogously to Example 28, (2R/2S)-3-[(1S,3R)-3-hydroxycyclohexyloxy]-2-propoxypropyl tert-butyidiphenyl-silyl ether and 2-(3-methoxyphenyl)oxazol-4-ylmethyl iodide give 3-{(1R,3S)-3-[5-methyl-2-(3-methoxyphenyl)oxazol-4-yl-methoxy]cyclohexyloxy}-2-propoxypropionic acid.

EXAMPLE 46

3-{(1R,3S)-3-[5-Methyl-2-(4-trifluoromethylphenyl)oxazol-4-ylmethoxy]cyclohexyl-oxy}-2-propoxypropionic acid

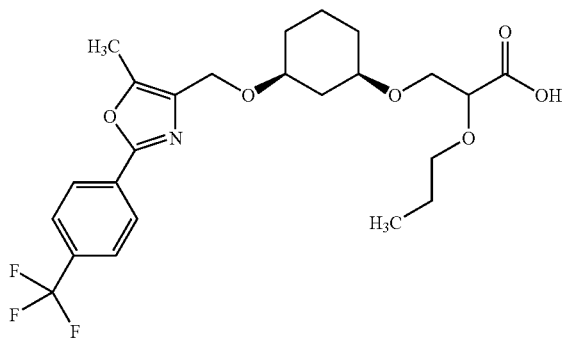

Analogously to Example 28, (2R/2S)-3-[(1S,3R)-3-hydroxycyclohexyloxy ]-2-propoxypropyl tert-butyidiphenyl-silyl ether and 2-(4-trifluoromethylphenyl)oxazol-4-ylmethyl iodide give 3-{(1R,3S)-3-[5-methyl-2-(4-trifluoromethylphenyl)oxazol-4-ylmethoxy]cyclohexyloxy}-2-propoxypropionic acid.

EXAMPLE 47

3-{(1R,3S)-3-[5-Methyl-2-(4-methylphenyl)oxazol-4-yl-methoxy]cyclohexyloxy}-2-propoxypropionic acid

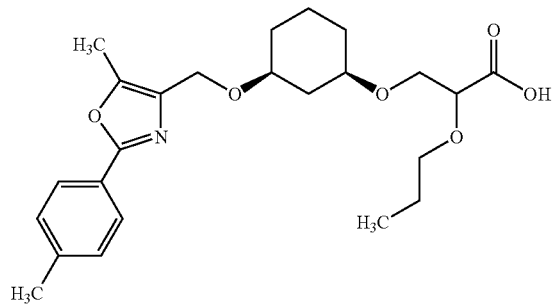

Analogously to Example 28, (2R/2S)-3-[(1S,3R)-3-hydroxycyclohexyloxy ]-2-propoxypropyl tert-butyldiphenyl-silyl ether and 2-(4-methylphenyl)oxazol-4-yl-methyl iodide give 3-{(1R,3S)-3-[5-methyl-2-(4-methylphenyl)oxazol4-ylmethoxy ]-cyclohexyloxy}-2-propoxypropionic acid.

EXAMPLE 48

3-{(1R,3S)-3-[5-Methyl-2-(4-trifluoromethoxyphenyl)oxazol-4-ylmethoxy ]cyclo-hexyloxy}-2-propoxypropionic acid

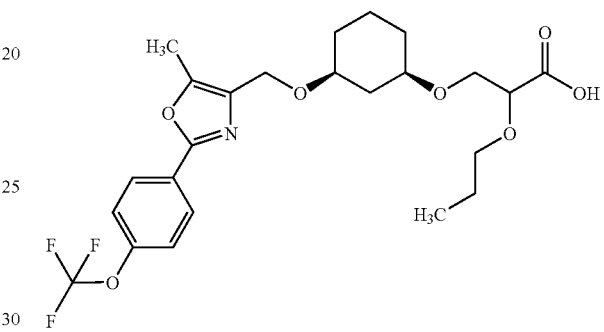

Analogously to Example 28, (2R/2S)-3-[(1S,3R)-3-hydroxycyclohexyloxy ]-2-propoxypropyl tert-butyidiphenyl-silyl ether and 2-(4-trifluoromethoxyphenyl)oxazol-4-ylm-ethyl iodide give 3-{(1R,3S)-3-[5-methyl-2-(4-trifluoromethoxyphenyl)oxazol-4-ylmethoxy]cyclohexyloxy}-2-propoxypropionic acid.

EXAMPLE 49

3-{(1R,3S)-3-[5-Methyl-2-(4-isopropylphenyl)oxazol-4-yl-methoxy]cyclohexyloxy }-2-propoxypropionic acid

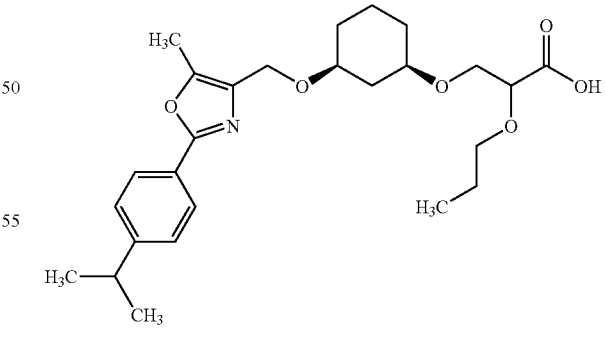

Analogously to Example 28, (2R/2S)-3-[(1S,3R)-3-hydroxycyclohexyloxy ]-2-propoxypropyl tert-butyidiphenyl-silyl ether and 2-(4-isopropylphenyl)oxazol-4-yl-methyl iodide give 3-{(1R,3S)-3-[5-methyl-2-(4-isopropylphenyl)oxazol-4-yl-methoxy]cyclohexyloxy}-2-propoxypropionic acid.

EXAMPLE 50

3-{(1R,3S)-3-[5-Methyl-2-(2-trifluoromethylphenyl)oxazol-4-ylmethoxy ]cyclohexyl-oxy}-2-propoxypropionic acid

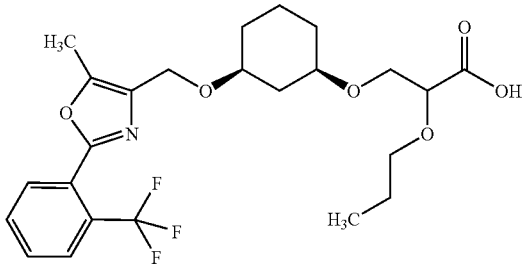

Analogously to Example 28, (2R/2S)-3-[(1S,3R)-3-hydroxycyclohexyloxy ]-2-propoxypropyl tert-butyldiphenylsilyl ether and 2-(2-trifluoromethylphenyl)oxazol-4-ylmethyl iodide give 3-{(1R,3S)-3-[5-methyl-2-(2-trifluoromethylphenyl)oxazol4-yl-methoxy ]cyclohexyloxy}-2-propoxypropionic acid.

EXAMPLE 51

3-{(1R,3S)-3-[5-Methyl-2-(2-naphthylphenyl)oxazol-4-ylmethoxy]cyclohexyloxy }-2-propoxypropionic acid

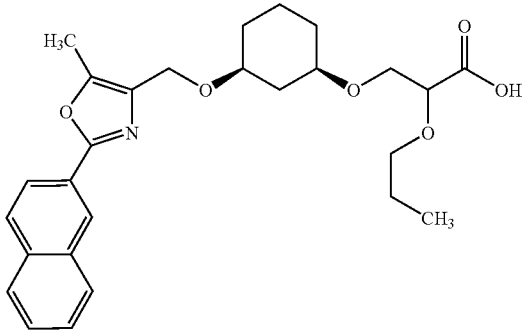

Analogously to Example 28, (2R/2S)-3-[(1S,3R)-3-hydroxycyclohexyloxy ]-2-propoxypropyl tert-butyldiphenylsilyl ether and 2-(2-naphthyl)oxazol-4-ylmethyl iodide give 3-{(1R,3S)-3-[5-methyl-2-(2-naphthylphenyl)oxazol-4-yl-methoxy ]cyclo-hexyloxy}-2-propoxypropionic acid.

EXAMPLE 52

3-{(1R,3S)-3-[5-Methyl-2-(3-trifluoromethylphenyl)oxazol-4-ylmethoxy ]cyclohexyl-oxy}-2-propoxypropionic acid

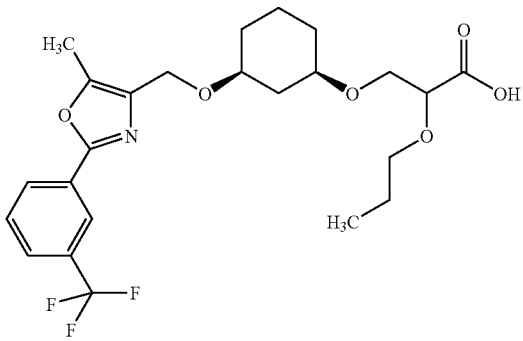

Analogously to Example 28, (2R/2S)-3-[(1S,3R)-3-hydroxycyclohexyloxy ]-2-propoxypropyl tert-butyldiphenylsilyl ether and 2-(3-trifluoromethylphenyl)oxazol4-ylmethyl iodide give 3-{(1R,3S)-3-[5-methyl-2-(3-trifluoromethylphenyl)oxazol4-yl-methoxy]cyclohexyloxy}-2-propoxypropionic acid.

EXAMPLE 53

3-{(1R,3S)-3-[5-Ethyl-2-(3-methoxyphenyl)oxazol-4-yl-methoxy]cyclohexyloxy}-2-propoxypropionic acid

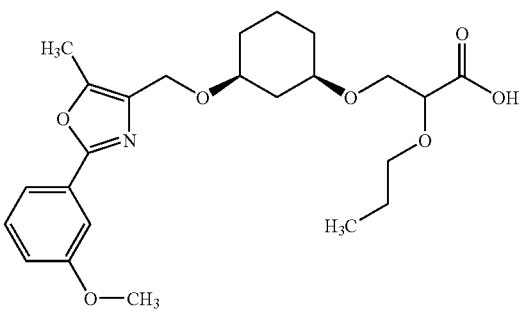

Analogously to Example 28, (2R/2S)-3-[(1S,3R)-3-hydroxycyclohexyloxy ]-2-propoxypropyl tert-butyidiphenylsilyl ether and 5-ethyl-2-(3-methoxyphenyl)oxazol-4-ylmethyl iodide give 3-{(1R,3S)-3-[5-ethyl-2-(3-methoxyphenyl)oxazol-4-yl-methoxy]cyclohexyloxy}-2-propoxypropionic acid.

EXAMPLE 54

3-{(1R,3S)-3-[5-Ethyl-2-(4-methylphenyl)oxazol-4-yl-methoxy]cyclohexyloxy }-2-propoxypropionic acid

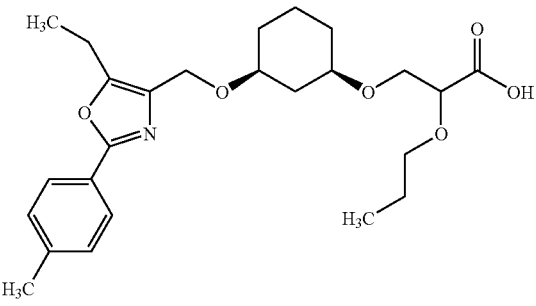

Analogously to Example 28, (2R/2S)-3-[(1S,3R)-3-hydroxycyclohexyloxy ]-2-propoxypropyl tert-butyidiphenylsilyl ether and 5-ethyl-2-(4-methylphenyl)oxazol-4-ylmethyl iodide give 3-{(1R,3S)-3-[5-ethyl-2-(4-methylphenyl)oxazol-4-ylmethoxy]-cyclohexyloxy}-2-propoxypropionic acid.

EXAMPLE 55

3-{(1R,3S)-3-[5-Ethyl-2-(2-trifluoromethylphenyl)oxazol-4-ylmethoxy]cyclohexyl-oxy}-2-propoxypropionic acid

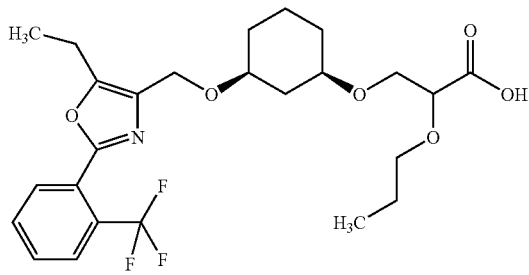

Analogously to Example 28, (2R/2S)-3-[(1S,3R)-3-hydroxycyclohexyloxy ]-2-propoxypropyl tert-butyldiphenylsilyl ether and 5-ethyl-2-(2-trifluoromethylphenyl)-oxazol-4-ylmethyl iodide give 3-{(1R,3S)-3-[5-ethyl-2-(2-trifluoromethylphenyl)-oxazol-4-ylmethoxy] cyclohexyloxy}-2-propoxypropionic acid.

EXAMPLE 56

3-{(1R,3S)-3-[5-Ethyl-2-(2,6-dimethylphenyl)oxazol-4-ylmethoxy]cyclohexyloxy }-2-propoxypropionic acid

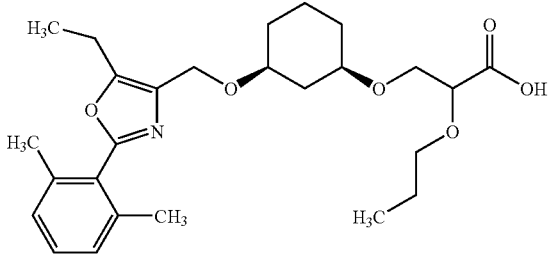

Analogously to Example 28, (2R/2S)-3-[(1S,3R)-3-hydroxycyclohexyloxy ]-2-propoxypropyl tert-butyldiphenylsilyl ether and 5-ethyl-2-(2,6-dimethylphenyl)-oxazol-4-ylmethyl iodide give 3-{(1R,3S)-3-[5-ethyl-2-(2,6-dimethylphenyl)oxazol-4-ylmethoxy]cyclohexyloxy}-2-propoxypropionic acid.

EXAMPLE 57

2-Ethoxy-3-{(1R,3S)-3-[5-methyl-2-(3-trifluoromethylphenyl)oxazol-4-ylmethoxy ]-cyclohexyloxy}propionic acid

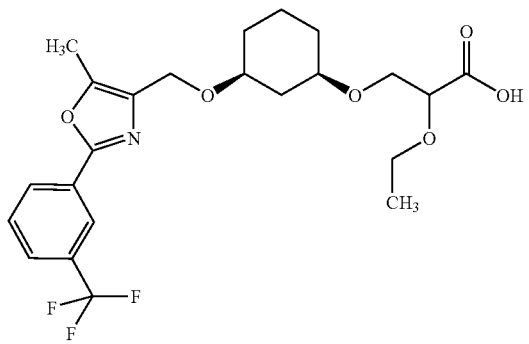

Analogously to Example 28, (2R/2S)-3-[(1S,3R)-3-benzyloxycyclohexyloxy ]-2-ethoxypropyl tert-butyldiphenylsilyl ether and 5-methyl-2-(3-trifluoromethylphenyl)-oxazol-4-ylmethyl iodide give 2-ethoxy-3-{(1R,3S)-3-[5-methyl-2-(3-trifluoro-methylphenyl)oxazol-4-ylmethoxy] cyclohexyloxy}propionic acid.

EXAMPLE 58

2-Ethoxy-3-{(1R,3S)-3-[5-methyl-2-(3-trifluoromethoxyphenyl)oxazol-4-ylmethoxy]-cyclohexyloxy}propionic acid

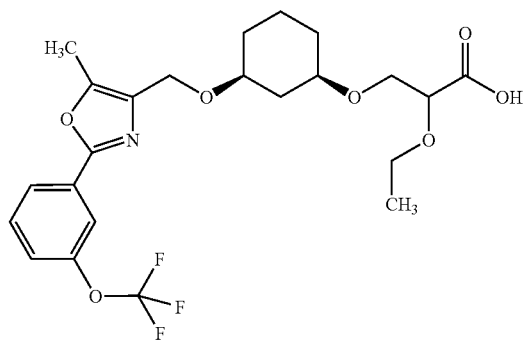

Analogously to Example 28, (2R/2S)-3-[(1S,3R)-3-benzyloxycyclohexyloxy ]-2-ethoxypropyl tert-butyidiphenylsilyl ether and 5-methyl-2-(3-trifluoromethoxy-phenyl)oxazol4-ylmethyl iodide give 2-ethoxy-3-{(1R,3S)-3-[5-methyl-2-(3-tri-fluoromethoxyphenyl)oxazol-4-ylmethoxy] cyclohexyloxy}propionic acid.

EXAMPLE 59

2-Ethoxy-3-{(1R,3S)-3-[5-methyl-2-(4-trifluoromethylphenyl)oxazol-4-ylmethoxy]-cyclohexyloxy}propionic acid

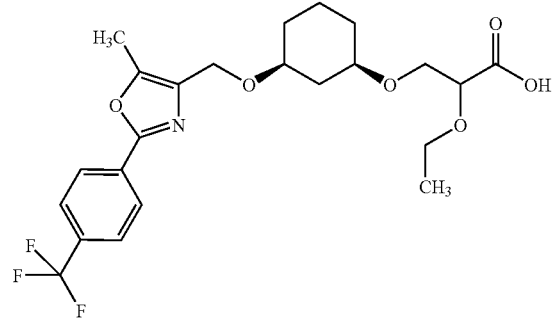

Analogously to Example 28, (2R/2S)-3-[(1S,3R)-3-benzyloxycyclohexyloxy ]-2-ethoxypropyl tert-butyldiphenylsilyl ether and 5-methyl-2-(4-trifluoromethylphenyl)-oxazol-4-ylmethyl iodide give 2-ethoxy-3-{(1R,3S)-3-[5-methyl-2-(4-trifluoro-methylphenyl)oxazol-4-ylmethoxy] cyclohexyloxy}propionic acid.

EXAMPLE 60

2-Ethoxy-3-{(1R,3S)-3-[5-methyl-2-(4-trifluoromethoxyphenyl)oxazol-4-ylmethoxy ]-cyclohexyloxy}propionic acid

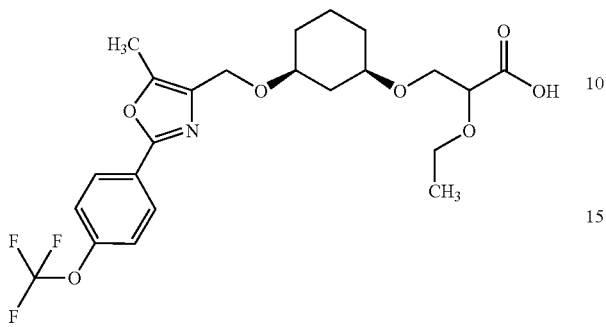

Analogously to Example 28, (2R/2S)-3-[(1S,3R)-3-benzyloxycyclohexyloxy ]-2-ethoxypropyl tert-butyidiphenylsilyl ether and 5-methyl-2-(4-trifluoromethoxy-phenyl)oxazol-4-ylmethyl iodide give 2-ethoxy-3-{(1R,3S)-3-[5-methyl-2-(4-tri-fluoromethoxyphenyl)oxazol-4-ylmethoxy] cyclohexyloxy}propionic acid.

EXAMPLE 61

2-Ethoxy-3-{(1R,3S)-3-[5-methyl-2-(4-isopropylphenyl)oxazol-4-ylmethoxy ]cyclo-hexyloxy}propionic acid

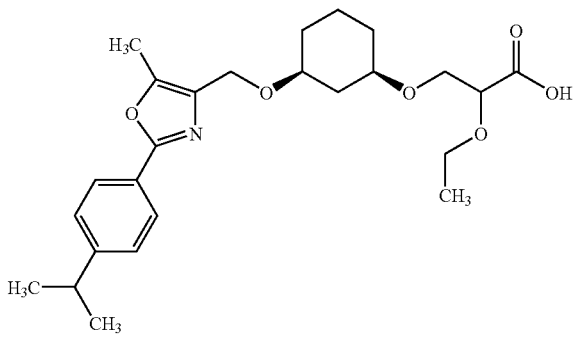

Analogously to Example 28, (2R/2S)-3-[(1S,3R)-3-benzyloxycyclohexyloxy ]-2-ethoxypropyl tert-butyldiphenylsilyl ether and 5-methyl-2-(4-isopropylphenyl)-oxazol-4-ylmethyl iodide give 2-ethoxy-3-{(1R,3S)-3-[5-methyl-2-(4-isopropyl-phenyl)oxazol-4-ylmethoxy] cyclohexyloxy}propionic acid.

EXAMPLE 62

2-Ethoxy-3-{(1R,3S)-3-[5-methyl-2-(2-trifluoromethylphenyl)oxazol4-ylmethoxy ]-cyclohexyloxy}propionic acid

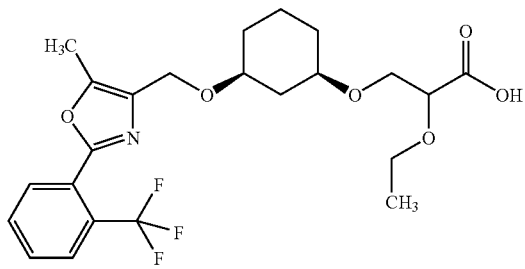

Analogously to Example 28, (2R/2S)-3-[(1S,3R)-3-benzyloxycyclohexyloxy ]-2-ethoxypropyl tert-butyldiphenylsilyl ether and 5-methyl-2-(2-trifluoromethylphenyl)-oxazol4-ylmethyl iodide give 2-ethoxy-3-{(1R,3S)-3-[5-methyl-2-(2-trifluoro-methylphenyl)oxazol-4-ylmethoxy ]cyclohexyloxy}propionic acid.

EXAMPLE 63

2-Ethoxy-3-{(1R,3S)-3-[5-methyl-2-(2,4-dimethylphenyl)oxazol4-ylmethoxy]cyclo-hexyloxy}propionic acid

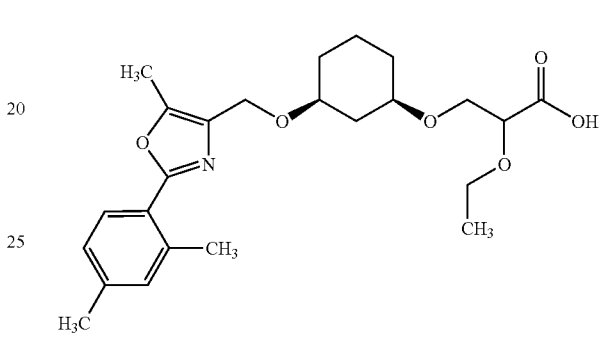

Analogously to Example 28, (2R/2S)-3-[(1S,3R)-3-benzyloxycyclohexyloxy ]-2-ethoxypropyl tert-butyldiphenylsilyl ether and 5-methyl-2-(2,4-dimethylphenyl)-oxazol4-ylmethyl iodide give 2-ethoxy-3-{(1R,3S)-3-[5-methyl-2-(2,4-dimethyl-phenyl)oxazol-4-ylmethoxy] cyclohexyloxy}propionic acid.

EXAMPLE 64

2-Ethoxy-3-{(1R,3S)-3-[5-methyl-2-(4-biphenyl)oxazol-4-ylmethoxy]cyclohexyl-oxy}propionic acid

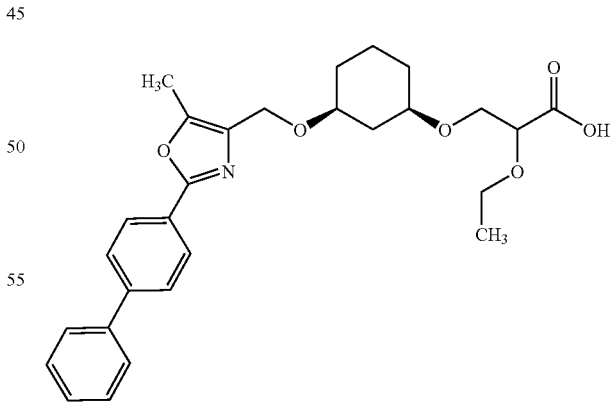

Analogously to Example 28, (2R/2S)-3-[(1S,3R)-3-benzyloxycyclohexyloxy ]-2-ethoxypropyl tert-butyldiphenylsilyl ether and 5-methyl-2-(4-biphenyl)oxazol-4-yl-methyl iodide give 2-ethoxy-3-{(1R,3S)-3-[5-methyl-2-(4-biphenyl)oxazol-4-yl-methoxy]cyclohexyloxy}propionic acid.

EXAMPLE 65

2-Ethoxy-3-[(1R,3S)-3-(5-ethyl-2-(2-tolyl)oxazol-4-yl-methoxy)cyclohexyloxy]-propionic acid

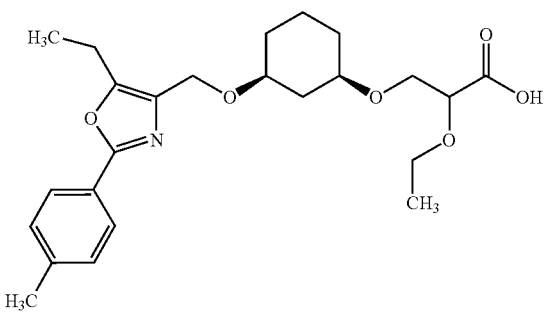

Analogously to Example 28, (2R/2S)-3-[(1S,3R)-3-ben-zyloxycyclohexyloxy ]-2-ethoxypropyl tert-butyldiphenyl-silyl ether and 5-methyl-2-(4-methylphenyl)oxazol-4-ylm-ethyl iodide give 2-ethoxy-3-[(1R,3S)-3-(5-ethyl-2-(2-tolyl)oxazol-4-ylmethoxy)-cyclohexyloxy]propionic acid.

EXAMPLE 68

2-Ethoxy-3-[(1R,3S)-3-(5-ethyl-2-(4-isopropylphenyl)ox-azol-4-ylmethoxy)cyclo-hexyloxy]propionic acid

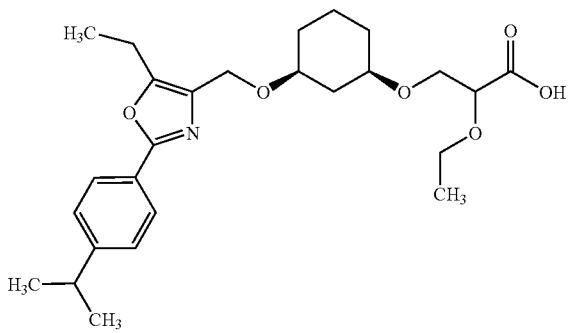

Analogously to Example 28, (2R/2S)-3-[(1S,3R)-3-ben-zyloxycyclohexyloxy ]-2-ethoxypropyl tert-butyldiphenyl-silyl ether and 5-methyl-2-(4-isopropylphenyl)-oxazol-4-yl-methyl iodide give 2-ethoxy-3-[(1R,3S)-3-(5-ethyl-2-(4-isopropyl-phenyl)oxazol-4-ylmethoxy)cyclohexyloxy] propionic acid.

EXAMPLE 67

2-Ethoxy-3-[(1R,3S)-3-(5-ethyl-2-(2-trifluoromethylphe-nyl)oxazol-4-ylmethoxy)-cyclohexyloxy]propionic acid

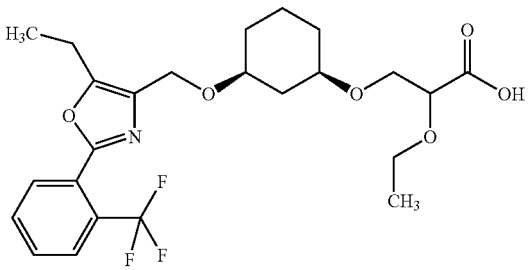

Analogously to Example 28, (2R/2S)-3-[(1S,3R)-3-ben-zyloxycyclohexyloxy ]-2-ethoxypropyl tert-butyldiphenyl-silyl ether and 5-methyl-2-(2-trifluoromethylphenyl)-ox-azol-4-ylmethyl iodide give 2-ethoxy-3-[(1R,3S)-3-(5-ethyl-2-(2-trifluoromethyl-phenyl)oxazol-4-ylmethoxy) cyclohexyloxy]propionic acid.

EXAMPLE 68

2-Ethoxy-3-[(1R,3S)-3-(5-ethyl-2-(2,4-dimethylphenyl)ox-azol4-ylmethoxy)cyclo-hexyloxy]propionic acid

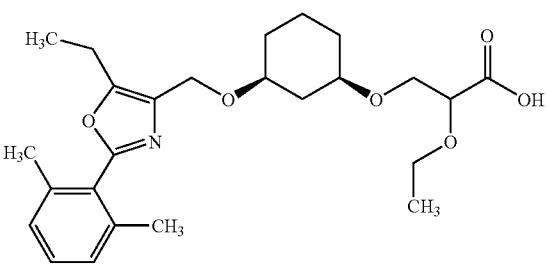

Analogously to Example 28, (2R/2S)-3-[(1S,3R)-3-ben-zyloxycyclohexyloxy ]-2-ethoxypropyl tert-butyldiphenyl-silyl ether and 5-methyl-2-(2,4-dimethylphenyl)-oxazol-4-ylmethyl iodide give 2-ethoxy-3-[(1R,3S)-3-(5-ethyl-2-(2,4-dimethyl-phenyl)oxazol-4-ylmethoxy)cyclohexyloxy] propionic acid.

EXAMPLE 68

3-{(1R,3S)-3-[5-Ethyl-2-(4-isopropylphenyl)oxazol-4-yl-methoxy]cyclohexyloxy}-2-propoxypropionic acid

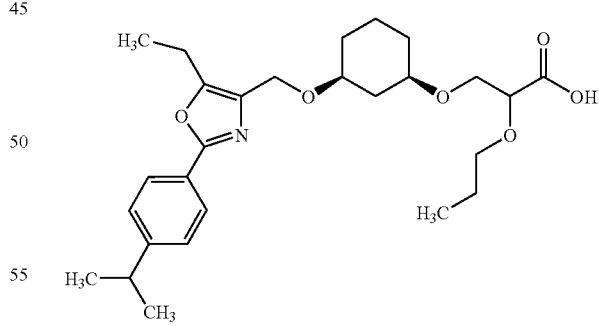

Analogously to Example 28, (2R/2S)-3-[(1S,3R)-3-hy-droxycyclohexyloxy ]-2-propoxypropyl tert-butyldiphenyl-silyl ether and 5-ethyl-2-(4-isopropylphenyl)oxazol-4-ylm-ethyl iodide give 3-{(1R,3S)-3-[5-ethyl-2-(4-isopropylphenyl)oxazol-4-yl-methoxy ]cyclohexyloxy}-2-propoxypropionic acid.

EXAMPLE 70

2-Ethoxy-3-{(1R,3S)-3-[5-methyl-2-phenyloxazol-4-yl-methoxy]cyclohexyloxy}-propionic acid

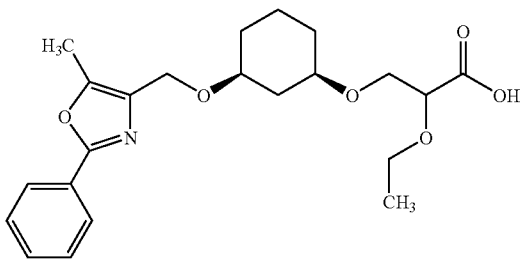

Analogously to Example 28, (2R/2S)-3-[(1S,3R)-3-benzyloxycyclohexyloxy ]-2-ethoxypropyl tert-butyldiphenylsilyl ether and 5-methyl-2-phenyloxazol-4-ylmethyl iodide give 2-ethoxy-3-{(1R,3S)-3-[5-methyl-2-phenyloxazol-4-ylmethoxy ]cyclo-hexyloxy}propionic acid.

EXAMPLE 71

2-Ethoxy-3-{(1R,3S)-3-[5-methyl-2-(3-methylphenyl)oxazol-4-ylmethoxy ]cyclo-hexyloxy}propionic acid

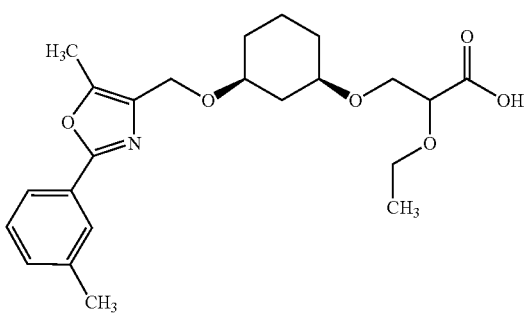

Analogously to Example 28, (2R/2S)-3-[(1S,3R)-3-benzyloxycyclohexyloxy ]-2-ethoxypropyl tert-butyldiphenylsilyl ether and 5-methyl-2-(3-methylphenyl)oxazol-4-ylmethyl iodide give 2-ethoxy-3-{(1R,3S)-3-[5-methyl-2-(3-methylphenyl)oxazol-4-ylmethoxy]cyclohexyloxy}propionic acid.

EXAMPLE 72

2-Ethoxy-3-{(1R,3S)-3-[5-methyl-2-(3-methoxyphenyl)oxazol-4-ylmethoxy]cyclo-hexyloxy}propionic acid

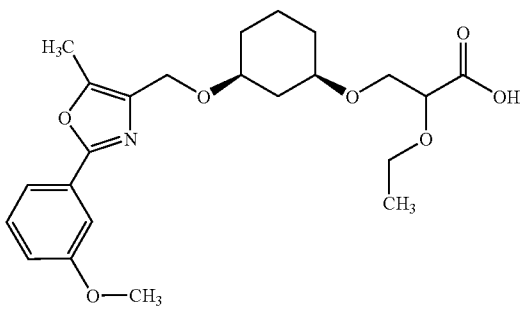

Analogously to Example 28, (2R/2S)-3-[(1S,3R)-3-benzyloxycyclohexyloxy ]-2-ethoxypropyl tert-butyldiphenylsilyl ether and 5-methyl-2-(3-methoxyphenyl)oxazol-4-ylmethyl iodide give 2-ethoxy-3-{(1R,3S)-3-[5-methyl-2-(3-methoxyphenyl)-oxazol4-ylmethoxy]cyclohexyloxy}propionic acid.

EXAMPLE 73

2-Ethoxy-3-{(1R,3S)-3-[5-methyl-2-(4-methylphenyl)oxazol-4-ylmethoxy]cyclo-hexyloxy}propionic acid

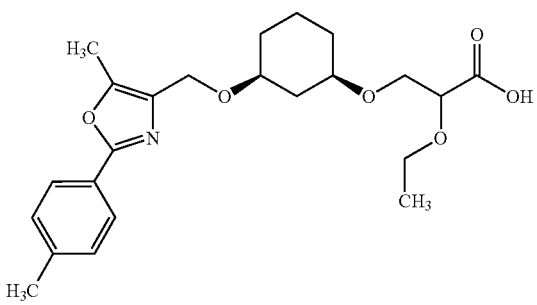

Analogously to Example 28, (2R/2S)-3-[(1S,3R)-3-benzyloxycyclohexyloxy ]-2-ethoxypropyl tert-butyidiphenylsilyl ether and 5-methyl-2-(4-methylphenyl)oxazol-4-ylmethyl iodide give 2-ethoxy-3-{(1R,3S)-3-[5-methyl-2-(4-methylphenyl)oxazol-4-ylmethoxy]cyclohexyloxy}propionic acid.

EXAMPLE 74

2-Ethoxy-3-{(1R,3S)-3-[5-methyl-2-(2-naphthyl)oxazol-4-ylmethoxy]cyclohexyloxy}-propionic acid

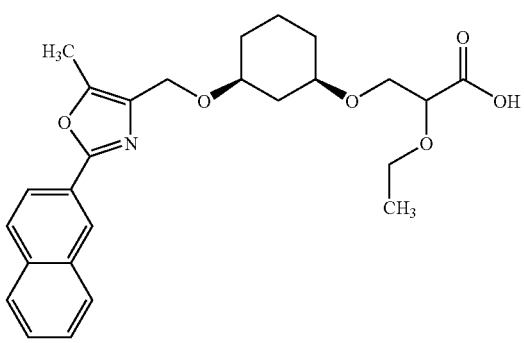

Analogously to Example 28, (2R/2S)-3-[(1S,3R)-3-benzyloxycyclohexyloxy ]-2-ethoxypropyl tert-butyidiphenylsilyl ether and 5-methyl-2-(2-naphthyl)oxazol-4-yl-methyl iodide give 2-ethoxy-3-{(1R,3S)-3-[5-methyl-2-(2-naphthyl)oxazol-4-yl-methoxy]cyclohexyloxy}propionic acid.

EXAMPLE 75
3-{(1R,3S)-3-[5-Ethyl-2-(3-methoxyphenyl)oxazol-4-yl-methoxy]cyclohexyloxy}-2-propoxypropionic acid

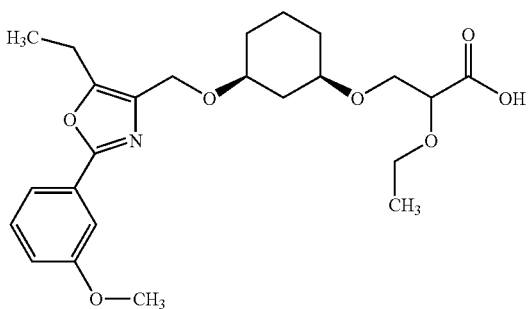

Analogously to Example 28, (2R/2S)-3-[(1S,3R)-3-hydroxycyclohexyloxy ]-2-propoxypropyl tert-butyldiphenylsilyl ether and 5-ethyl-2-(3-methoxyphenyl)oxazol-4-ylmethyl iodide give 3-{(1R,3S)-3-[5-ethyl-2-(3-methoxyphenyl)oxazol-4-yl-methoxy]cyclohexyloxy}-2-propoxypropionic acid.

EXAMPLE 76
(R)-3-[(1R,3S)-3-(5-Methyl-2-m-tolyloxazol4-ylmethoxy) cyclohexyloxy]-2-(4-tri-fluoromethylbenzyloxy)propionic acid chiral

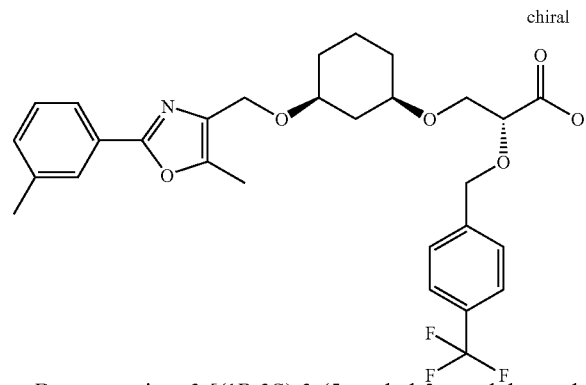

By separating 3-[(1R,3S)-3-(5-methyl-2-m-tolyloxazol-4-ylmethoxy)cyclohexyloxy ]-2-(4-trifluoromethylbenzyloxy)propanoic acid (Example 13) by chiral HPLC, in addition to enantiomerically pure (S)-3-[(1R,3S)-3-(5-methyl-2-m-tolyloxazol-4-yl-methoxy)cyclohexyloxy ]-2-(4-trifluoromethylbenzyloxy)propionic acid (Example 10), (R)-3-[(1R,3S)-3-(5-methyl-2-m-tolyloxazol-4-ylmethoxy) cyclohexyl-oxy ]-2-(4-trifluoromethylbenzyloxy)propionic acid is obtained.

EXAMPLE 77
(R)-3-[(1R,3S)-3-(5-Methyl-2-(3-trifluoromethylphenyl )oxazol4-yl methoxy)cyclo-hexyloxy]-2-(4-trifluoromethyl-benzyloxy)propionic acid

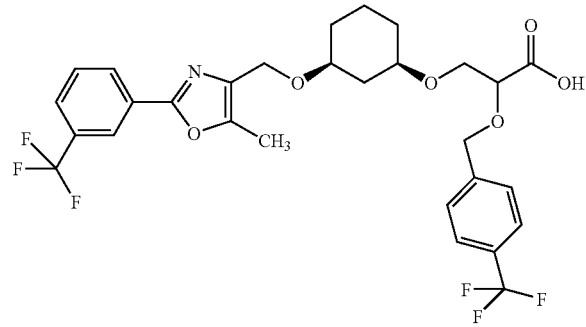

Analogously to Example 28, (2R/2S)-3-[(1R,3S)-1-hydroxycyclohex-1-yloxy]-2-(4-trifluoromethylbenzyloxy) tert-butyldimethylsilyl ether and 5-methyl-2-(3-trifluoromethylphenyl)oxazol4-ylmethyl iodide give (R)-3-[(1R,3S)-3-(5-methyl-2-(3-tri-fluoromethylphenyl)oxazol-4-yl-methoxy)cyclohexyloxy ]-2-(4-trifluoromethylbenzyl-oxy)propionic acid.

EXAMPLE 78
(R)-3-[(1R,3S)-3-(5-Methyl-2-(4-trifluoromethoxyphenyl)oxazol4-ylmethoxy)cyclo-hexyloxy]-2-(4-trifluoromethyl-benzyloxy)propionic acid

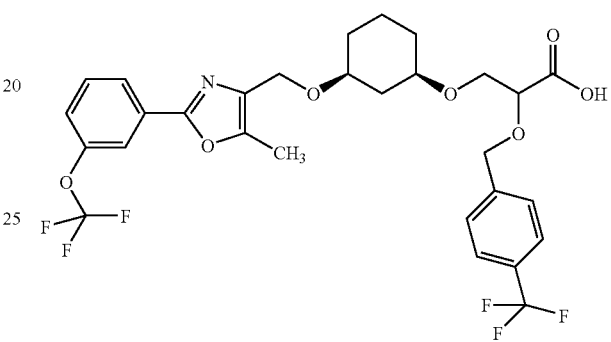

Analogously to Example 28, (2R/2S)-3-[(1R,3S)-1-hydroxycyclohex-1-yloxy]-2-(4-trifluoromethylbenzyloxy) tert-butyldimethylsilyl ether and 5-methyl-2-(3-trifluoromethoxyphenyl)oxazol-4-ylmethyl iodide give (R)-3-[(1R,3S)-3-(5-methyl-2-(4-tri-fluoromethoxyphenyl)oxazol-4-yl-methoxy)cyclohexyloxy]-2-(4-trifluoromethyl-benzyloxy) propionic acid.

EXAMPLE 79
(R)-3-[(1R,3S)-3-(5-Methyl-2-(4-isopropylphenyl)oxazol-4-ylmethoxy)cyclohexyl-oxy]-2-(4-trifluoromethylbenzyloxy)propionic acid

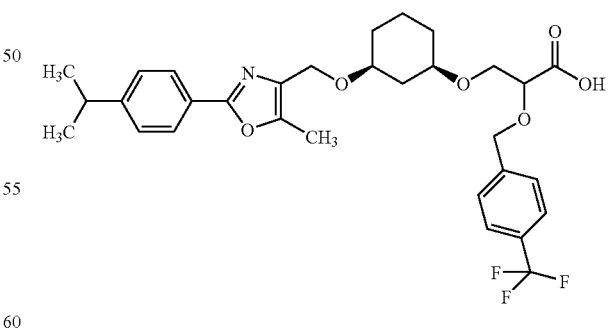

Analogously to Example 28, (2R/2S)-3-[(1R,3S)-1-hydroxycyclohex-1-yloxy]-2-(4-trifluoromethylbenzyloxy) tert-butyldimethylsilyl ether and 5-methyl-2-(4-isopropylphenyl)oxazol-4-ylmethyl iodide give (R)-3-[(1R,3S)-3-(5-methyl-2-(4-isopropyl-phenyl)oxazol-4-ylmethoxy)cyclo-hexyloxy ]-2-(4-trifluoromethylbenzyloxy)propionic acid.

EXAMPLE 80

(R)-3-[(1R,3S)-3-(5-Methyl-2-(2-naphthyl)oxazol-4-yl-methoxy)cyclohexyloxy]-2-(4-trifluoromethylbenzyloxy)propionic acid

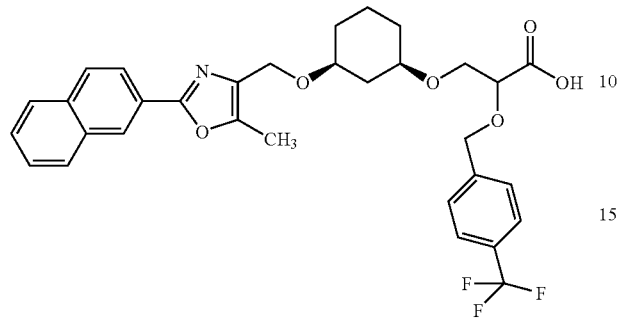

Analogously to Example 28, (2R/2S)-3-[(1R,3S)-1-hydroxycyclohex-1-yloxy]-2-(4-trifluoromethylbenzyloxy) tert-butyldimethylsilyl ether and 5-methyl-2-(2-naphthyl)-oxazol-4-ylmethyl iodide give (R)-3-[(1R,3S)-3-(5-methyl-2-(2-naphthyl)oxazol-4-ylmethoxy)cyclohexyloxy ]-2-(4-trifluoromethylbenzyloxy)propionic acid.

EXAMPLE 81

(R)-3-[(1R,3S)-3-(5-Methyl-2-(4-methylphenyl)oxazol-4-ylmethoxy)cyclohexyloxy]-2-(4-trifluoromethylbenzyloxy)propionic acid

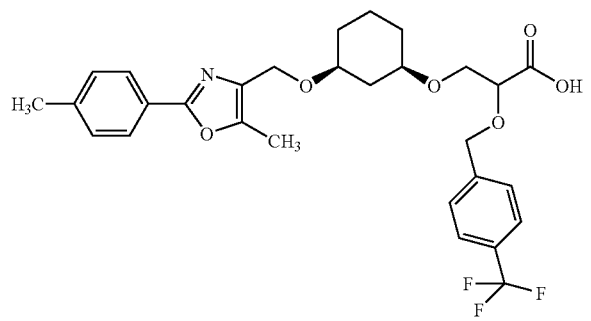

Analogously to Example 28, (2R/2S)-3-[(1R,3S)-1-hydroxycyclohex-1-yloxy]-2-(4-trifluoromethylbenzyloxy) tert-butyidimethylsilyl ether and 5-methyl-2-(4-methyl-phenyl)oxazol-4-yl methyl iodide give (R)-3-[(1R,3S)-3-(5-methyl-2-(4-methyl-phenyl)oxazol-4-ylmethoxy)cyclohexyloxy ]-2-(4-trifluoromethylbenzyloxy)propionic acid.

EXAMPLE 82

(R)-3-[(1R,3S)-3-(5-Methyl-2-(4-trifluoromethoxyphenyl)oxazol-4-ylmethoxy)cyclo-hexyloxy]-2-(4-trifluoromethyl-benzyloxy)propionic acid

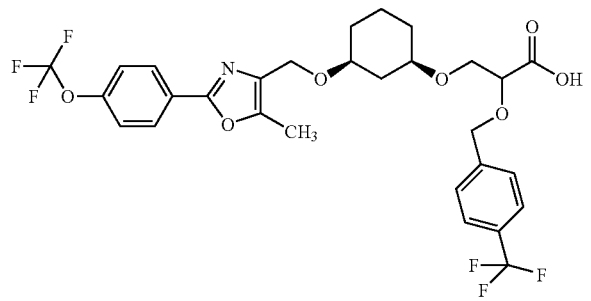

Analogously to Example 28, (2R/2S)-3-[(1R,3S)-1-hydroxycyclohex-1-yloxy]-2-(4-trifluoromethylbenzyloxy) tert-butyldimethylsilyl ether and 5-methyl-2-(4-trifluoromethoxyphenyl)oxazol4-ylmethyl iodide give (R)-3-[(1R,3S)-3-(5-methyl-2-(4-tri-fluoromethoxyphenyl)oxazol-4-yl-methoxy)cyclohexyloxy ]-2-(4-trifluoromethyl-benzyloxy)propionic acid.

EXAMPLE 83

(R)-3-[(1R,3S)-3-(5-Methyl-2-(3-trifluoromethylphenyl)oxazol-4-ylmethoxy)cyclo-hexyloxy]-2-(4-trifluoromethyl-benzyloxy)propionic acid

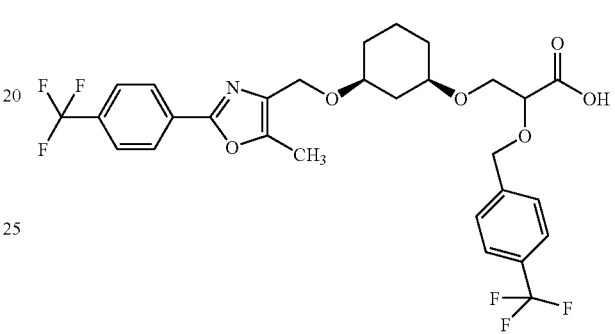

Analogously to Example 28, (2R/2S)-3-[(1R,3S)-1-hydroxycyclohex-1-yloxy]-2-(4-trifluoromethylbenzyloxy) tert-butyldimethylsilyl ether and 5-methyl-2-(3-trifluoromethylphenyl)oxazol4-ylmethyl iodide give (R)-3-[(1R,3S)-3-(5-methyl-2-(3-tri-fluoromethylphenyl)oxazol-4-yl-methoxy)cyclohexyloxy ]-2-(4-trifluoromethylbenzyl-oxy)propionic acid.

EXAMPLE 84

(R)-3-[(1R,3S)-3-(5-Methyl-2-(3-methoxyphenyl)oxazol-4-ylmethoxy)cyclohexyl-oxy]-2-(4-trifluoromethylbenzyloxy)propionic acid

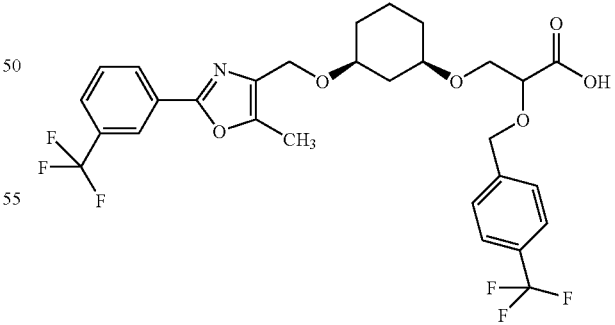

Analogously to Example 28, (2R/2S)-3-[(1R,3S)-1-hydroxycyclohex-1-yloxy]-2-(4-trifluoromethylbenzyloxy) tert-butyidimethylsilyl ether and 5-methyl-2-(3-methoxy-phenyl)oxazol-4-ylmethyl iodide give (R)-3-[(1R,3S)-3-(5-methyl-2-(3-methoxy-phenyl)oxazol-4-ylmethoxy)cyclo-hexyloxy]-2-(4-trifluoromethylbenzyloxy)propionic acid.

EXAMPLE 85

3-{(1R,3S)-3-[5-Methyl-2-(3-trifluoromethylphenyl)oxazol-4-ylmethoxy]cyclohexyl-oxy}-2-isobutoxypropionic acid

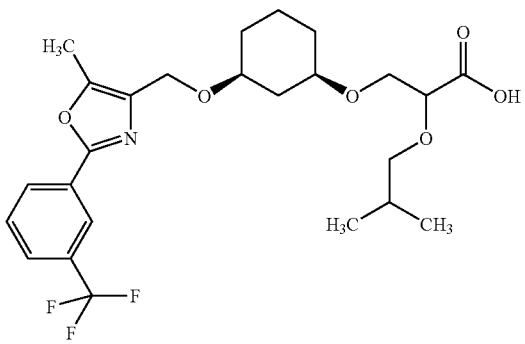

Analogously to Example 28, (2R/2S)-3-[(1S,3R)-3-hydroxycyclohexyloxy ]-2-iso-butoxypropyl tert-butyldiphenylsilyl ether and 2-(3-trifluoromethylphenyl)oxazol-4-ylmethyl iodide give 3-{(1R,3S)-3-[5-methyl-2-(3-trifluoromethylphenyl)oxazol-4-yl-methoxy ]cyclohexyloxy}-2-isobutoxypropionic acid.

EXAMPLE 86

3-{(1R,3S)-3-[5-Methyl-2-(3-methoxyphenyl)oxazol-4-yl-methoxy]cyclohexyloxy}-2-isobutoxypropionic acid

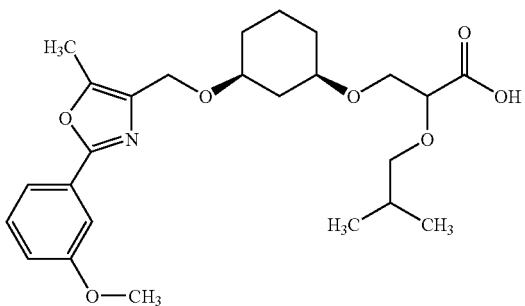

Analogously to Example 28, (2R/2S)-3-[(1S,3R)-3-hydroxycyclohexyloxy ]-2-iso-butoxypropyl tert-butyidiphenylsilyl ether and 2-(3-methoxyphenyl)oxazol-4-yl-methyl iodide give 3-{(1R,3S)-3-[5-methyl-2-(3-methoxyphenyl)oxazol-4-yl-methoxy ]cyclohexyloxy}-2-isobutoxypropionic acid.

EXAMPLE 87

3-{(1R,3S)-3-[5-Methyl-2-(4-methylphenyl)oxazol-4-ylmethoxy]cyclohexyloxy}-2-isobutoxypropionic acid

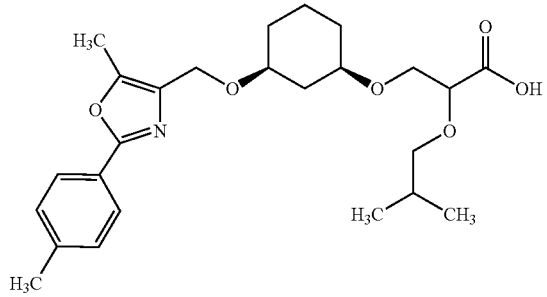

Analogously to Example 28, (2R/2S)-3-[(1S,3R)-3-hydroxycyclohexyloxy ]-2-iso-butoxypropyl tert-butyldiphenylsilyl ether and 2-(4-methylphenyl)oxazol-4-ylmethyl iodide give 3-{(1R,3S)-3-[5-methyl-2-(4-methylphenyl)oxazol-4-ylmethoxy ]cyclo-hexyloxy}-2-isobutoxypropionic acid.

EXAMPLE 88

3-{(1R,3S)-3-[5-Methyl-2-(4-isopropylphenyl)oxazol-4-yl-methoxy]cyclohexyloxy}-2-isobutoxypropionic acid

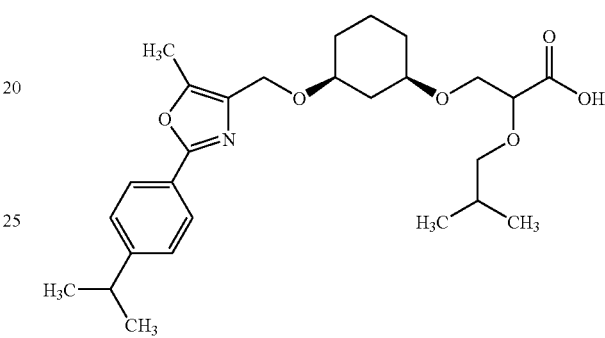

Analogously to Example 28, (2R/2S)-3-[(1S,3R)-3-hydroxycyclohexyloxy]-2-iso-butoxypropyl tert-butyldiphenylsilyl ether and 2-(4-isopropylphenyl)oxazol-4-yl-methyl iodide give 3-{(1R,3S)-3-[5-methyl-2-(4-isopropylphenyl)oxazol-4-yl-methoxy]cyclohexyloxy}-2-isobutoxypropionic acid.

EXAMPLE 89

(2R/2S)-3-[(1R,3S)-3-(5-Methyl-2-m-tolyloxazol-4-yl-methoxymethyl)cyclohexyloxy]-2-(4-trifluoromethylbenzyloxy)propionic acid

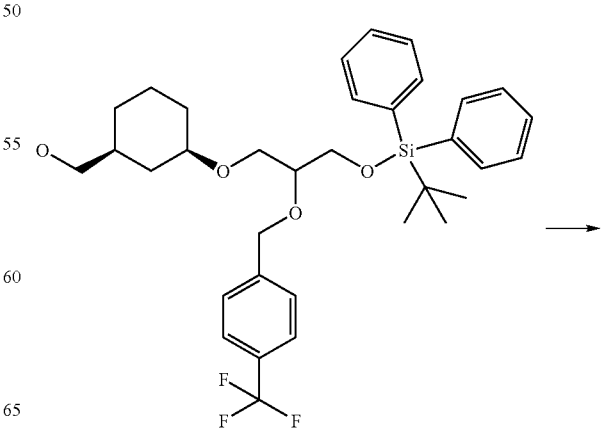

-continued

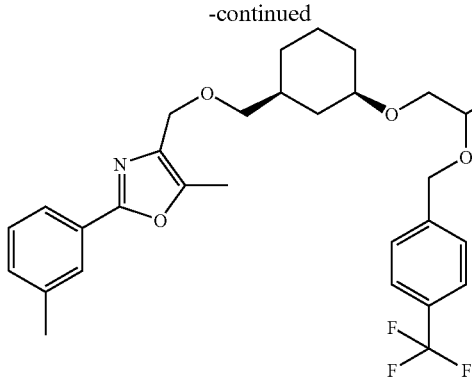

333 mg of (2R/2S)-3-[(1R,3S)-3-hydroxymethylcyclohexyloxy]-2-(4-trifluoro-methylbenzyloxy)propyl tert-butyldiphenylsilyl ether are dissolved in MTBE, 125 mg of potassium tert-butoxide and 347 mg of 5-methyl-2-(3-methylphenyl)-oxazol 4-ylmethyl iodide are added successively and the mixture is stirred at RT. After the reaction has gone to completion, water and MTBE are added and the organic phase is separated off, dried over MgSO4 and concentrated. The residue is chromatographed on silica gel (Flash-Master, heptane/ethyl acetate 1:0→1:1→0:1). The product-containing fractions are concentrated, the residue (420 mg) is dissolved in 10 ml of THF and 174 mg of TBAF are added. After 72 h of stirring, water and MTBE are added and the organic phase is separated off, washed with NaCl solution, dried over MgSO4 and concentrated. The residue is dissolved in 2 ml of acetone, 0.5 ml of 1.9M Jones reagent is added and the mixture is stirred at RT overnight. After addition of water and MTBE, the organic phase is separated off, dried over MgSO4 and concentrated. The residue is purified by HPLC, giving 200 mg of (2R/2S)-3-[(1R,3S)-3-(5-methyl-2-m-tolyloxazol-4-ylmethoxymethyl)-cyclohexyloxy ]-2-(4-trifluoromethylbenzyloxy)propionic acid. C30H34F3NO6 (561.6), MS (ESI): 562 (M+H+).

(S)-3-[(1R,3S)-3-(5-Methyl-2-m-tolyloxazol4-yl-methoxymethyl)cyclohexyloxy]-2-(4-trifluoromethylbenzyloxy)propionic acid

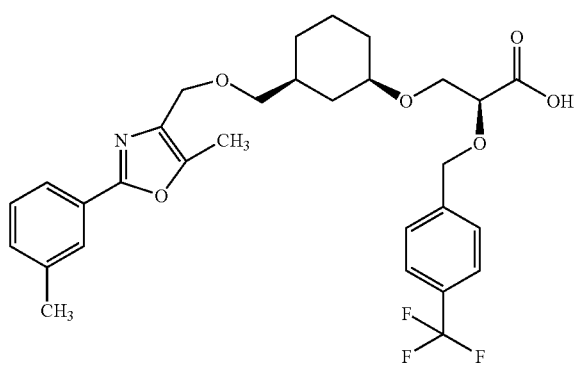

Separation of (2R/2S)-3-[(1R,3S)-3-(5-methyl-2-m-tolyloxazol-4-ylmethoxymethyl)-cyclohexyloxy ]-2-(4-trifluoromethylbenzyloxy)propionic acid by chiral HPLC gives (2S)-3-[(1R,3S)-3-(5-methyl-2-m-tolyloxazol4-yl-methoxymethyl)cyclohexyloxy ]-2-(4-trifluoromethylbenzyloxy)propionic acid. C30H34F3NO6 (561.6), MS (ESI): 562 (M+H+).

EXAMPLE 90

(R)-3-[(1R,3S)-3-(5-Methyl-2-m-tolyloxazol-4-yl-methoxymethyl)cyclohexyloxy]-2-(4-trifluoromethylbenzyloxy)propionic acid

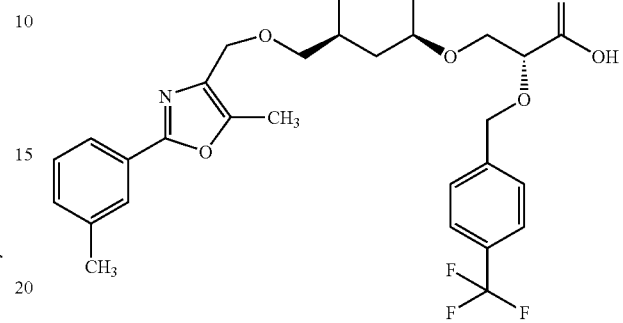

Separation of (2R/2S)-3-[(1R,3S)-3-(5-methyl-2-m-tolyloxazol-4-ylmethoxymethyl)-cyclohexyloxy ]-2-(4-trifluoromethylbenzyloxy)propionic acid by chiral HPLC gives (2R)-3-[(1R,3S)-3-(5-methyl-2-m-tolyloxazol-4-yl-methoxymethyl)cyclohexyloxy ]-2-(4-trifluoromethylbenzyloxy)propionic acid. C30H34F3NO6 (561.6), MS (ESI): 562 (M+H+).

EXAMPLE 91

2-[(1R,3S)-3-(5-Methyl-2-m-tolyloxazol4-ylmethoxy)cyclohexyloxymethyl]-3-(3-trifluoromethylphenyl)propionic acid

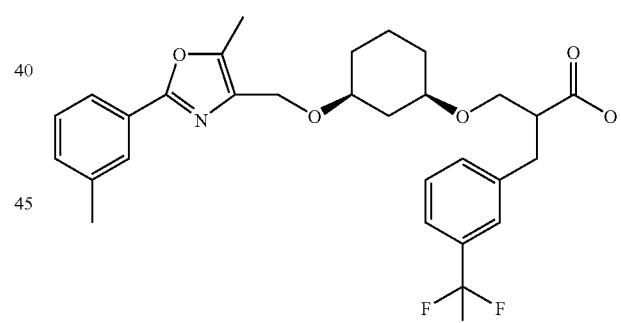

Analogously to Example 9, ethyl (1R,3S)-2-[3-(5-methyl-2-m-tolyloxazol-4-yl-methoxy)cyclohexyloxymethyl ]acrylate and 3-bromobenzotrifluoride give 2-[(1R,3S)-3-(5-methyl-2-m-tolyloxazol4-ylmethoxy)cyclohexyloxymethyl]-3-(3-trifluoromethylphenyl)propionic acid.

Characterization of the examples by mass spectroscopy:

| Example | Empirical formula | Mass of the monoisotope | Found by MS (ESI) as (M + H+) |
|---|---|---|---|
| 1 | C23H30FNO5 | 419.49 | 420 |
| 2 | C24H32FNO5 | 433.52 | 434 |
| 3 | C21H26FNO5 | 391.44 | 392 |
| 4 | C22H28FNO5 | 405.47 | 406 |

-continued

| Example | Empirical formula | Mass of the monoisotope | Found by MS (ESI) as (M + H$^+$) |
|---|---|---|---|
| 5 | C23H29NO5 | 399.49 | 400 |
| 6 | C31H40N2O5 | 520.67 | 521 |
| 7 | C30H38N2O5 | 506.65 | 507 |
| 8 | C23H31NO6 | 417.51 | 418 |
| 9 | C29H34FNO5 | 495.60 | 496 |
| 10 | C24H33NO6 | 431.53 | 432 |
| 11 | C29H32F3NO6 | 547.58 | 548 |
| 12 | C22H29NO6 | 403.48 | 404 |
| 13 | C29H32F3NO6 | 547.58 | 548 |
| 14 | C29H32F3NO6 | 547.58 | 548 |
| 15 | C29H35NO7 | 509.61 | 510 |
| 16 | C30H37NO6 | 507.63 | 508 |
| 17 | C29H35NO6 | 493.61 | 494 |
| 18 | C32H41NO6 | 535.69 | 536 |
| 19 | C29H32F3NO6 | 547.58 | 548 |
| 20 | C26H30ClNO6S | 520.05 | 521 |
| 21 | C25H31NO6 | 441.53 | 442 |
| 22 | C24H29NO6 | 427.50 | 428 |
| 23 | C26H33NO6 | 455.56 | 456 |
| 24 | C24H31NO6 | 429.52 | 430 |
| 25 | C30H35NO6 | 505.62 | 506 |
| 26 | C25H33NO6 | 443.55 | 444 |
| 27 | C28H33NO6 | 479.58 | 480 |
| 28 | C21H27NO6 | 389.45 | 390 |
| 29 | C22H26F3NO6 | 457.45 | 458 |
| 30 | C22H26F3NO7 | 473.45 | 474 |
| 31 | C22H26F3NO6 | 457.45 | 458 |
| 32 | C22H29NO6 | 403.48 | 404 |
| 33 | C23H31NO6 | 417.51 | 418 |
| 34 | C22H26F3NO6 | 457.45 | 458 |
| 35 | C25H29NO6 | 439.51 | 440 |
| 36 | C23H31NO6 | 417.51 | 418 |
| 37 | C27H31NO6 | 465.55 | 466 |
| 38 | C23H31NO7 | 433.51 | 434 |
| 39 | C23H31NO6 | 417.51 | 418 |
| 40 | C23H28F3NO6 | 471.48 | 472 |
| 41 | C24H33NO6 | 431.53 | 432 |
| 42 | C23H31NO6 | 417.51 | 418 |
| 43 | C24H33NO6 | 431.53 | 432 |
| 44 | C24H30F3NO7 | 501.50 | 502 |
| 45 | C24H33NO7 | 447.53 | 448 |
| 46 | C24H30F3NO6 | 485.51 | 486 |
| 47 | C24H33NO6 | 431.53 | 432 |
| 48 | C24H30F3NO7 | 501.50 | 502 |
| 49 | C26H37NO6 | 459.59 | 460 |
| 50 | C24H30F3NO6 | 485.51 | 486 |
| 51 | C27H33NO6 | 467.57 | 468 |
| 52 | C24H30F3NO6 | 485.51 | 486 |
| 53 | C25H35NO7 | 461.56 | 462 |
| 54 | C25H35NO6 | 445.56 | 446 |
| 55 | C25H32F3NO6 | 499.53 | 500 |
| 56 | C26H37NO6 | 459.59 | 460 |
| 57 | C23H28F3NO6 | 471.48 | 472 |
| 58 | C23H28F3NO7 | 487.48 | 488 |
| 59 | C23H28F3NO6 | 471.48 | 472 |
| 60 | C23H28F3NO7 | 487.48 | 488 |
| 61 | C25H35NO6 | 445.56 | 446 |
| 62 | C23H28F3NO6 | 471.48 | 472 |
| 63 | C24H33NO6 | 431.53 | 432 |
| 64 | C28H33NO6 | 479.58 | 480 |
| 65 | C24H33NO6 | 431.53 | 432 |
| 66 | C26H37NO6 | 459.59 | 460 |
| 67 | C24H30F3NO6 | 485.51 | 486 |
| 68 | C25H35NO6 | 445.56 | 446 |
| 69 | C27H39NO6 | 473.62 | 474 |
| 70 | C22H29NO6 | 403.48 | 404 |
| 71 | C23H31NO6 | 417.51 | 418 |
| 72 | C23H31NO7 | 433.51 | 434 |
| 73 | C23H31NO6 | 417.51 | 418 |
| 74 | C26H31NO6 | 453.54 | 454 |
| 75 | C24H33NO7 | 447.53 | 448 |
| 76 | C29H32F3NO6 | 547.58 | 548 |
| 77 | C29H29F6NO6 | 601.55 | 602 |
| 78 | C29H29F6NO7 | 617.55 | 618 |
| 79 | C31H36F3NO6 | 575.63 | 576 |
| 80 | C32H32F3NO6 | 583.61 | 584 |
| 81 | C29H32F3NO6 | 547.58 | 548 |
| 82 | C29H29F6NO7 | 617.55 | 618 |
| 83 | C29H29F6NO6 | 601.55 | 602 |
| 84 | C29H32F3NO7 | 563.58 | 564 |
| 85 | C25H32F3NO6 | 499.53 | 500 |
| 86 | C25H35NO7 | 461.56 | 462 |
| 87 | C25H35NO6 | 445.56 | 446 |
| 88 | C27H39NO6 | 473.62 | 474 |
| 89 | C30H34F3NO6 | 561.60 | 562 |
| 90 | C30H34F3NO6 | 561.60 | 562 |
| 91 | C29H32F3NO5 | 531.58 | 532 |

We claim:

1. A compound of the formula I

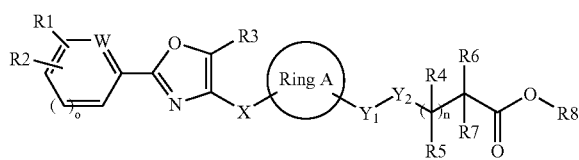

I wherein:

Ring A is (C3-C8)-cycloalkanediyl or (C3-C8)-cycloalkenediyl;

R1, R2 are each independently H, F, Cl, Br, $CF_3$, $OCF_3$, (C1-C6)-alkyl, $SCF_3$, $SF_5$, $OCF_2$—$CHF_2$, (C6-C10)-aryl, (C6-C10)-aryloxy, OH or $NO_2$; or R1 and R2, taken together with the atoms of the phenyl ring to which they are attached, form a fused, partially saturated or unsaturated, bicyclic (C6-C10)-aryl group;

R3 is H, (C1-C6)-alkyl, (C3-C8)-cycloalkyl, (C1-C3)-alkyl-(C3-C8)-cycloalkyl, phenyl, (C1-C3)-alkyl-phenyl or (C1-C3)-alkyl which is fully or partially substituted by F;

W is CH;

o is 1;

X is (C1-C6)-alkanediyl, wherein one or more carbon atoms of said (C1-C6)-alkanediyl group are optionally replaced by oxygen atoms;

Y1 is O;

Y2 is CR12R13;

n is 0,1 or2;

R4 is H, F or (C1-C6)-alkyl;

R5 is H, F or (C1-C6)-alkyl;

R6 is H or (C1-C6)-alkyl; or is F if n is not 0;

R7 is O-(C1-C6)-alkyl, wherein said O-(C1-C6)-alkyl group is optionally substituted by phenyl, wherein said phenyl group is optionally substituted by OH, NR10R11, O-(C1-C6)-alkyl, O-(C2-C6)-alkenyl, O-(C2-C6)-alkynyl, O-(C3-C8)-cycloalkyl, O-phenyl, O-(C5-C11)-heteroaryl or (C1-C6)-alkyl, wherein said (C1-C6)-alkyl substituent is optionally substituted by F (fully or partially) or O-(C1-C6)-alkyl, wherein said O-(C1-C6)-alkyl substituent is optionally substituted by F (fully or partially), Cl, Br, I, OH, NR10R11, CO-(C1-C6)-alkyl, CO-(C6-C10)-aryl, CO-(C1-C6)-alkyl-(C6-C10)-aryl, CO-(C5-C11)-heteroaryl, C(O)—O-(C1-C6)-alkyl, C(O)—O-(C1-C6)-alkyl-(C6-C10)-aryl, C(O)—O-(C6-C10)-aryl, C(O)—O-(C5-C11)-heteroaryl, $SO_2$-(C1-C6)-alkyl, $SO_2$-(C1-C6)-alkyl-(C6-C10)-aryl, $SO_2$-(C1-C6)-alkyl-$SO_2$-(C1-C6)-alkyl, $SO_2$-(C6-C10)-aryl, $SO_2$-(C5-C11)-heteroaryl;

R8 is H or (C1-C6)-alkyl;

R9 is H or (C1-C6)-alkyl which is optionally substituted by phenyl;

R10 is H or (C1-C6)-alkyl which is optionally substituted by phenyl;

R11 is H or (C1-C6)-alkyl which is optionally substituted by phenyl;

R12 is H or (C1-C6)-alkyl;

R13 is H or (C1-C6)-alkyl;

and pharmaceutically acceptable salts thereof.

2. The compound of claim 1 wherein:

Ring A is $(C_3-C_8)$-cycloalkanediyl or $(C_3-C_8)$-cycloalkenediyl

X is (C1-C6)-alkanediyl, wherein the C1 or C2 carbon atom (with respect to Ring A) in said (C1-C6)-alkanediyl group is optionally replaced by an oxygen atom;

and pharmaceutically acceptable salts thereof.

3. The compound of claim 2 wherein:

Ring A is cis-cyclohexane-1,3-diyl;

R1, R2 are each independently H, F, CF3, (C1-C6)-alkyl, O-(C1-C6)-alkyl or phenyl, or R1 and R2, taken together with the atoms of the phenyl ring to which they are attached, form naphthyl;

R3 is (C1-C6)-alky;

W is CH;

o is 1;

X is (CH2)O or CH2-O—CH2;

Y1 is O;

Y2 is CH2;

n is 0 or 1;

R4 is H;

R5 is H;

R6 is H;

R7 is O-(C1-C6)-alkyl, wherein said O-(C1-C6)-alkyl group is optionally substituted by phenyl, wherein said phenyl group is optionally substituted by (C1-C6)-alkyl, O-(C1-C6)-alkyl or CF3;

R8 is H;

R10 is (C1-C6)-alkyl;

R11 is (C1-C6)-alkyl substituted by phenyl;

and pharmaceutically acceptable salt thereof.

4. A pharmaceutical composition comprising a pharmaceutically acceptable carrier and one or more compounds of claim 1.

5. The pharmaceutical composition of claim 4 further comprising at least one additional active ingredient.

6. The pharmaceutical composition of claim 5 wherein said additional active ingredient is an antidiabetic.

7. A method of treating disorders of insulin resistance comprising administering to a patient in need thereof a therapeutically effective amount of a compound of claim 1.

8. A method of treating diabetes mellitus including the prevention of the squelae associated therewith comprising administering to a patient in need thereof a therapeutically effective amount of a compound of claim 1.

9. A method of treating disorders of insulin resistance comprising administering to a patient in need thereof a therapeutically effective amount of a compound of claim 1 in combination with at least one further active compound.

* * * * *

SEQUENCE LISTING

<160> NUMBER OF SEQ ID NOS: 2

<210> SEQ ID NO 1
<211> LENGTH: 19
<212> TYPE: DNA
<213> ORGANISM: Artificial
<220> FEATURE:
<223> OTHER INFORMATION: Binding Site of Yeast Transcription Factor GAL4

<400> SEQUENCE: 1
cggagtactg tcctccgag                                                19

<210> SEQ ID NO 2
<211> LENGTH: 19

```
<212> TYPE: DNA
<213> ORGANISM: Artificial
<220> FEATURE:
<223> OTHER INFORMATION: Binding Site of Yeast Transcription Factor GAL4

<400> SEQUENCE: 2
ctcggaggac agtactccg                                              19
```